United States Patent
Yu et al.

(10) Patent No.: US 10,358,494 B2
(45) Date of Patent: Jul. 23, 2019

(54) CS1-SPECIFIC CHIMERIC ANTIGEN RECEPTOR ENGINEERED IMMUNE EFFECTOR CELLS

(71) Applicant: OHIO STATE INNOVATION FOUNDATION, Columbus, OH (US)

(72) Inventors: Jianhua Yu, Columbus, OH (US); Craig Hofmeister, Columbus, OH (US); Jianhong Chu, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 14/888,877

(22) PCT Filed: May 2, 2014

(86) PCT No.: PCT/US2014/036684
§ 371 (c)(1),
(2) Date: Nov. 3, 2015

(87) PCT Pub. No.: WO2014/179759
PCT Pub. Date: Nov. 6, 2014

(65) Prior Publication Data
US 2016/0075784 A1 Mar. 17, 2016

Related U.S. Application Data

(60) Provisional application No. 61/876,492, filed on Sep. 11, 2013, provisional application No. 61/819,141, filed on May 3, 2013.

(51) Int. Cl.
| | |
|---|---|
| C07K 16/28 | (2006.01) |
| C07K 14/725 | (2006.01) |
| C07K 14/705 | (2006.01) |
| C07K 16/30 | (2006.01) |
| A61K 39/00 | (2006.01) |

(52) U.S. Cl.
CPC ...... *C07K 16/2803* (2013.01); *C07K 14/7051* (2013.01); *C07K 14/70521* (2013.01); *C07K 16/3061* (2013.01); *A61K 2039/505* (2013.01); *C07K 2317/622* (2013.01); *C07K 2317/73* (2013.01); *C07K 2319/00* (2013.01); *C07K 2319/02* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | | | |
|---|---|---|---|---|
| 7,709,610 B2 * | 5/2010 | Williams | ......... | C07K 14/70503 424/141.1 |
| 2004/0038339 A1 | 2/2004 | Kufer et al. | | |
| 2011/0044980 A1 | 2/2011 | Ghayur et al. | | |
| 2011/0150870 A1 | 6/2011 | Rader et al. | | |
| 2012/0064083 A1 | 3/2012 | Williams et al. | | |
| 2013/0121915 A1 | 5/2013 | Paas et al. | | |
| 2013/0280285 A1 * | 10/2013 | Schonfeld | .......... | C07K 14/7051 424/185.1 |
| 2014/0178950 A1 | 6/2014 | Franklin et al. | | |
| 2014/0242701 A1 * | 8/2014 | Shiku | ................. | C07K 14/7051 435/455 |
| 2014/0314667 A1 | 10/2014 | Hill et al. | | |
| 2015/0038684 A1 * | 2/2015 | Jensen | ............... | C07K 16/2803 530/391.9 |
| 2015/0307564 A1 | 10/2015 | Young et al. | | |

FOREIGN PATENT DOCUMENTS

| | | | |
|---|---|---|---|
| CN | 103224561 A | 7/2013 | |
| JP | 2012/121878 A1 | 6/2012 | |
| WO | 2010/051391 A1 | 5/2010 | |
| WO | 2012071411 A2 | 5/2012 | |
| WO | 2012079000 A1 | 6/2012 | |
| WO | WO-2013051718 A1 * | 4/2013 | ......... C07K 14/7051 |

OTHER PUBLICATIONS

Chu et al. (Clin. Cancer Res. Mar. 27, 2014 20:3989-4000).*
Rudikoff et al. (PNAS USA, 1982, 79: 1979-1983).*
Coleman et al. (Research in Immunology, 1994; 145(1): 33-36).*
Abaza et al. (Journal of Protein Chemistry, vol. 11, No. 5, 1992, pp. 433-444).*
Ibragimova and Wade (Biophysical Journal, Oct. 1999, vol. 77, pp. 2191-2198).*
Prazma and Tedder (Immunology Letters 2008, 115: 1-8).*
Siegel R., et al., Cancer J Clin, 2012, 62:10-29.
Palumbo A., et al., Leukemia 2009, 23: 449-456.
Podar, K., et al.; Leukemia 2009, 0.: 10-24.
Sadelain, M., et al., Nat Rev Cancer, 2003, 3: 35-45.
Hsi ED, et al., Clin Cancer Res, 2008, 14:2775-84.
Benson, DM Jr., et al., J Clin Oncol 2012, 30: 2013-5.
Tai, YT, et al., Blood 2009, 113:4309-18.
Tai, YT, et al., Blood 2008, 112:1329-37.
Imai C., et al., Leukemia 2004, 18:676-84.
Maher, J., et al., Nat. Biotechnol 2002, 20:70-5.
Woof, et al., Nat. Rev. Immunol., 4(2):89-99, 2004.
Chu, J. et al.(2013). CS1-specific chimeric antigen receptor (CAR)-engineered natural killer cells enhance in vitro and in vivo antitumor activity against human multiple myeloma. Leukemia, 28(4), 917-927.

(Continued)

*Primary Examiner* — Peter J Reddig
(74) *Attorney, Agent, or Firm* — Meunier Carlin & Curfman LLC

(57) ABSTRACT

Disclosed herein are chimeric antigen receptors (CAR) that can specifically recognize tumor-associated antigens (TAA) on multiple myeloma (MM) cells. Also disclosed are immune effector cells, such as T cells or Natural Killer (NK) cells, that are engineered to express these CARs. Therefore, also disclosed are methods of providing an anti-tumor immunity in a subject with MM that involves adoptive transfer of the disclosed immune effector cells engineered to express the disclosed CARs.

11 Claims, 28 Drawing Sheets

Specification includes a Sequence Listing.

(56) References Cited

OTHER PUBLICATIONS

Chu, J. et al. (2014). Genetic modification of T cells redirected toward CS1 enhances eradication of myeloma cells. Clinical Cancer Research, 20(15), 3989-4000.
Godfrey J., et al., Leuk Lymphoma 2012, 53:1666-1676.
Narni-Mancinelli E, et al., Int Immunol 2011 23:427-431.
Morgan RA, et al., Mol Ther 2010 18:843-851.
Porter, DL, et al., N Engl J Med 2011 365:725-733.
Fauriat C., et al., Leukemia 2006 20:732-733.
Rosenberg, et al., New Eng. J of Med., 319:1676, 1988.
Yu, J., et al., Immunity 2006, 24:575-90.
Becknell, B., et al., J Immunol Methods, 2005, 296:115-23.
Yu, J., et al., Blood 2010, 115:274-81.
He, S., et al., Blood 2013, 121:4663-71.
Koehler, H., et al., Cancer Res 2007, 67:2265-73.
Sanchez, C., et al., Prostate Cancer Prostatic Dis, 2013, 16:123-31.
Chinnasamy, D., et al., J Clin Invest, 2010, 120:3953-68.
Mitsiades, CS., et al., Cancer Cell 2004, 5:221-30.
Runnels, JM, et al., J Biomed Opt, 2011, 16:011006.
Olson, JA, et al., Blood 2010, 115:4293-4301.
Ruggeri, L., et al., Science, 2002, 295:2097-2100.
Martin-Fontecha, A., et al., Nat Immunol, 2004, 5:1260-1265.
Tu, SP, et al., Cancer Res, 2011, 71:4247-4259.
Ma, J. et al., Cell Mol Life Sci, 2003, 60:2334-2346.
Phillips, JH, et al., J Exp Med 1984 159:993-1008.
Spits, H., et al., Immunity 2007 26:11-16.
Francisco, JA, et al., Cancer Res, 2000, 60:3225-3231.
International Search Report and Written Opinion of the U.S. International Searching Authority from application No. PCT/US2014/036684 dated Sep. 23, 2014, 11 pages.
Burns et al. "A High Molecular Weight Melanoma-Associated Antigen-Specific Chimeric 1-4, 13-16 Antigen Receptor Redirects Lymphocytes to Target Human Melanomas," Cancer Research, Apr. 15, 2010 (Apr. 15, 2010), vol. 70, pp. 3027-3031.
Jena, B., Dotti, G., & Cooper, L. J. (2010). Redirecting T-cell specificity by introducing a tumor-specific chimeric antigen receptor. Blood, 116(7), 1035-1044.
Jakubowiak, et al., Phae I trial of anti-CS1 monoclonal antibody elotuzumab in combination with bortezombi in the treatment of relapsed/refractory multiple myeloma, J Clin Oncol, 2012, 30(16):1960-5; Abstract, p. 1963, col. 2.
Schuster, et al., A phase II, multicenter trial of rindopepimut (CDX-110) in newly diagnosed glioblasomas: the ACT III study. Neuro Oncol. Epub Jan. 13, 2015, 17(6):854-61; Abstract.
International Search Report and Written Opinion, issued in International Application No. PCT/US2016/18955, dated Aug. 5, 2016.
Attianese, Greta Maria Paola Giordano et al. "A New Chimeric Antigen Receptor (CAR) Targeting the CD23 Antigen Expressed by Chronic Lymphocytic Leukemia (B-CLL) Cells." Blood 116.21 (2010): 2446-2446.
Casucci, Monica et al. "Dual Transgenesis of T Cells with a Novel CD44v6-Specific Chimeric Antigen Receptor and a Suicide Gene for Safe and Effective Targeting of Chemoresistance in Hematopoietic Tumors." Blood 118.21 (2011): 3125-3125.
Chu, Yaya et al. "Genetically Engineered Natural Killer (NK) Cell Immunotherapy for Poor Risk B-Cell (CD20+) Leukemia and Lymphoma." Blood 118.21 (2011): 1003-1003.
Extended European Search Report and Written Opinion, Application No. 14791494.9, dated Nov. 28, 2016, 12 pages.
Lonial, Sagar et al. "Elotuzumab in combination with lenalidomide and low-dose dexamethasone in relapsed or refractory multiple myeloma." Journal of Clinical Oncology 30.16 (2012): 1953-1959.
Topp, M. S. et al. "T-cells from multiple myeloma patients can be rendered to lyse CD138 (+) multiple myeloma cells by expression of a chimeric immunoreceptor targeting the myeloma-specific antigen HM 1.24." Blood. vol. 102. No. 11. 1900 M Street. NW Suite 200, Washington, DC 20036 USA: Amer Soc Hematology, 2003.
Office Action received in co-pending U.S. Appl. No. 15/597,436, dated Aug. 25, 2017.
International Preliminary Report on Patentability issued in application No. PCT/US2016/018955, dated Aug. 31, 2017.
Chu, Yaya & Ayello, Janet & Hochberg, Jessica & Murphy, James & Stier, Andrew & S. Cairo, Mitchell. (2012). Genetically engineered natural killer (NK) cell immunotherapy for poor risk B-cell (CD20+) leukemia and lymphoma (L/L). Cancer Research. 72. 3511-3511.
State Intellectual Property Office of China. English Translation of Office Action issued in Chinese Application No. 201480030178.9 on Jun. 4, 2018. 10 pages.
Almagro, Juan C., and Johan Fransson. "Humanization of antibodies." Front Biosci 13.1 (2008): 1619-1633.
Communication pursuant to Article 94(3) EPC issued by the European Patent Office in Application No. 14791494.9, dated Jan. 24, 2018.
Caruana, I. et al., From monoclonal antibodies to chimeric antigen receptors for the treatment of human malignancies, Semin Oncol, 2014, vol. 41, No. 5, 661-666.
Japanese Patent Office. Office Action issued in Application No. 2016-512083. dated Feb. 20, 2018. 3 pages (English Translation).
U.S. Patent and Trademark Office. Office Action issued in U.S. Appl. No. 15/597,436, dated Apr. 20, 2018.
Extended Search Report and Written Opinion. European Patent Office. European Application No. 16753226.6, dated Sep. 4, 2018. 9 pages.
Vyas, Maulik, et al. "Natural ligands and antibody-based fusion proteins: harnessing the immune system against cancer." Trends in molecular medicine 20.2 (2014): 72-82.
Office Action issued by the U.S. Patent and Trademark Office in U.S. Appl. No. 15/597,436 dated Oct. 5, 2018. 15 pages.
English Translation of Office Action issued by the Japanese Patent Office in Japanese Application No. P-2016-512083 on Dec. 18, 2018. 3 pages.
Notice of Allowance issued by the U.S. Patent and Trademark Office in U.S. Appl. No. 15/597,436 dated Jan. 22, 2019. 16 pages.
Siegel, Rebecca L., Kimberly D. Miller, and Ahmedin Jemal. "Cancer statistics, 2016." CA: a cancer journal for clinicians 66.1 (2018): 7-30.
Lonial, Sagar, et al., "Elotuzumab Therapy for Relapsed or Refractory Multiple Myeloma", The New England Journal of Medicine, Aug. 13, 2015, pp. 621-631.
Zonder, Jeffrey A. et al., "A phase 1, multicenter, open-label, dose escalation study of elotuzumab in patients with advanced multiple myeloma", Blood Journal, Jul. 19, 2012, vol. 120, No. 3, pp. 552-559.
Gormley, Nicole J. et al., "FDA Drug Approval: Elotuzumab in Combination with Lenalidomide and Dexamethasone for the Treatment of Relapsed or Refractory Multiple Myeloma", clincancerres.aacrjournals.org; Mar. 1, 2017, DOI: 10.1158/1078-0432.CCR-16-2870.
Hammer, Ohad, "CD19 as an attractive target for antibody-based therapy", mAbs 4:5, 571-577; Sep./Oct. 2012; © 2012 Landes Bioscience.
Communication pursuant to Rule 71(3). Issued by the European Patent Office in Application No. 14791494.9 on Feb. 6, 2019. 4 pages.
Gleason MK, Ross JA, Warlick ED, et al. CD16xCD33 bispecific killer cell engager (BiKE) activates NK cells against primary MDS and MDSC CD33+ targets. Blood. 2014;123(19):3016-3026.
Sentman, "A novel NKG2D-specific BiTE cancer immunotherapy", Dartmouth College, Hanover, NH, United States, accessed on-line Feb. 22, 2016, abstract.
Stamova S, Cartellieri M, Feldmann A, et al. Simultaneous engagement of the activatory receptors NKG2D and CD3 for retargeting of effector cells to CD33-positive malignant cells. Leukemia. 2011;25(6):1053-1056.
Wiernik A, Foley B, Zhang B, et al. Targeting natural killer cells to acute myeloid leukemia in vitro with a CD16 33 bispecific killer cell engager and ADAM17 inhibition. Clin Cancer Res. 2013;19(14):3844-3855.
Zhang T, Sentman CL. Cancer immunotherapy using a bispecific NK receptor fusion protein that engages both T cells and tumor cells. Cancer Res. 2011;71(6):2066-2076.

(56) References Cited

OTHER PUBLICATIONS

Wolf, et al., "BiTEs: bispecific antibody constructs with unique anti-tumor activity", Drug Discovery Today 10(18), 2005, 1237-1244.

* cited by examiner

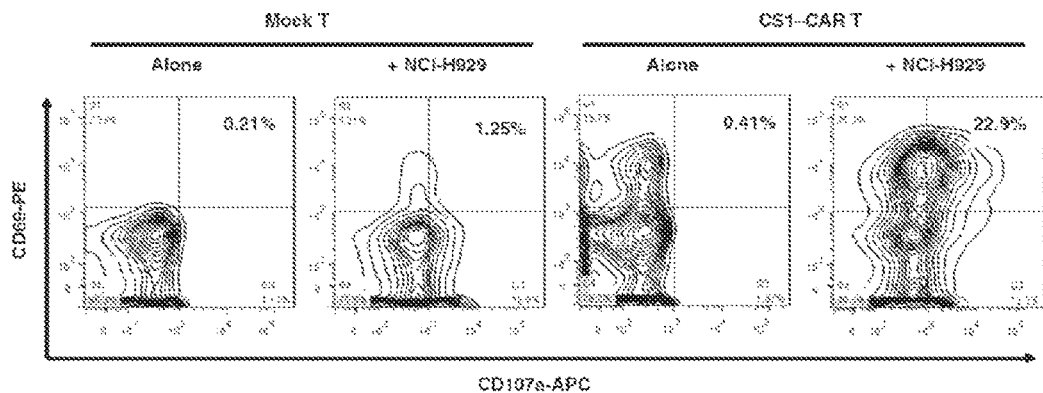
*Figure 3B*
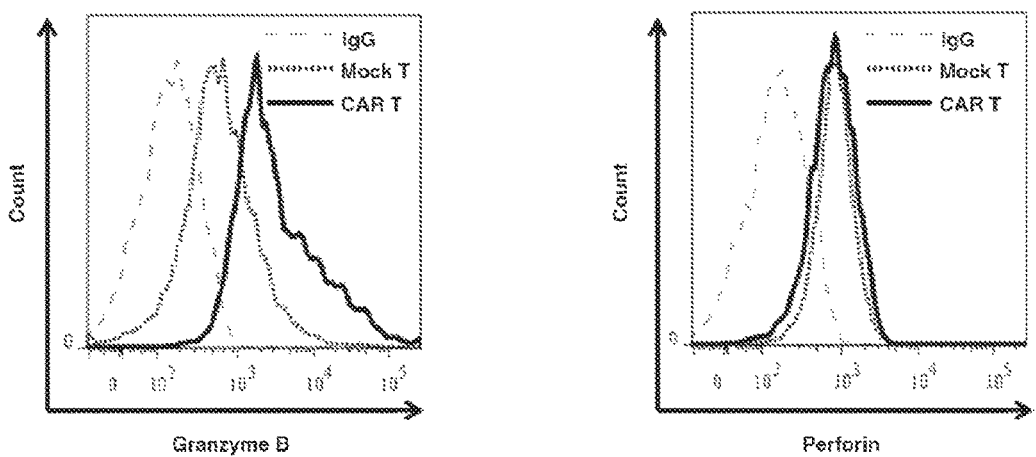
*Figure 3C*  *Figure 3D*

SEQUENCE LISTING

<160> NUMBER OF SEQ ID NOS: 29

<210> SEQ ID NO 1
<211> LENGTH: 18
<212> TYPE: PRT
<213> ORGANISM: Artificial Sequence
<220> FEATURE:
<223> OTHER INFORMATION: Synthetic Construct

<400> SEQUENCE: 1

Met Gly Trp Ser Ser Ile Ile Leu Phe Leu Val Ala Thr Ala Thr Gly
1               5                   10                  15

Val His

<210> SEQ ID NO 2
<211> LENGTH: 54
<212> TYPE: DNA
<213> ORGANISM: Artificial Sequence
<220> FEATURE:
<223> OTHER INFORMATION: Synthetic Construct

<400> SEQUENCE: 2
atgggatgga gctctatcat cctcttcttg gtagcaacag ctacaggtgt ccac        54

<210> SEQ ID NO 3
<211> LENGTH: 21
<212> TYPE: PRT
<213> ORGANISM: Artificial Sequence
<220> FEATURE:
<223> OTHER INFORMATION: Synthetic Construct

<400> SEQUENCE: 3

Met Ala Leu Pro Val Thr Ala Leu Leu Leu Pro Leu Ala Leu Leu Leu
1               5                   10                  15

His Ala Ala Arg Pro
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic Construct

<400> SEQUENCE: 4

Met Glu Thr Asp Thr Leu Leu Leu Trp Val Leu Leu Leu Trp Val Pro
1               5                   10                  15

Gly Ser Thr Gly
            20

<210> SEQ ID NO 5
<211> LENGTH: 16
<212> TYPE: PRT
<213> ORGANISM: Artificial Sequence
<220> FEATURE:
<223> OTHER INFORMATION: Synthetic Construct

<400> SEQUENCE: 5

Leu Glu Pro Lys Ser Cys Asp Lys Thr His Thr Cys Pro Pro Cys Pro
1               5                   10                  15

<210> SEQ ID NO 6
<211> LENGTH: 48
<212> TYPE: DNA
<213> ORGANISM: Artificial Sequence
<220> FEATURE:
<223> OTHER INFORMATION: Synthetic Construct

<400> SEQUENCE: 6
ctcgagccca aatcttgtga caaaactcac acatgcccac cgtgcccg              48

<210> SEQ ID NO 7
<211> LENGTH: 24
<212> TYPE: PRT
<213> ORGANISM: Artificial Sequence
<220> FEATURE:
<223> OTHER INFORMATION: Synthetic Construct

<400> SEQUENCE: 7

Ile Tyr Ile Trp Ala Pro Leu Ala Gly Thr Cys Gly Val Leu Leu
1               5                   10                  15

Ser Leu Val Ile Thr Leu Tyr Cys
            20

<210> SEQ ID NO 8
<211> LENGTH: 27
<212> TYPE: PRT
<213> ORGANISM: Artificial Sequence
<220> FEATURE:
<223> OTHER INFORMATION: Synthetic Construct

<400> SEQUENCE: 8

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 9
<211> LENGTH: 27
<212> TYPE: PRT
<213> ORGANISM: Artificial Sequence
<220> FEATURE:
<223> OTHER INFORMATION: Synthetic Construct

<400> SEQUENCE: 9

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 10
<211> LENGTH: 81
<212> TYPE: DNA
<213> ORGANISM: Artificial Sequence
<220> FEATURE:
<223> OTHER INFORMATION: Synthetic Construct

<400> SEQUENCE: 10
ttttgggtgc tggtggtggt tggtggagtc ctggcttgct atagcttgct agtaacagtg    60
gcctttatta ttttctgggt g                                              81

<210> SEQ ID NO 11
<211> LENGTH: 42
<212> TYPE: PRT
<213> ORGANISM: Artificial Sequence
<220> FEATURE:
<223> OTHER INFORMATION: Synthetic Construct

<400> SEQUENCE: 11

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
                35                  40

<210> SEQ ID NO 12
<211> LENGTH: 41
<212> TYPE: PRT
<213> ORGANISM: Artificial Sequence
<220> FEATURE:
<223> OTHER INFORMATION: Synthetic Construct

<400> SEQUENCE: 12

Arg Ser Lys Arg Ser Arg Leu Leu His Ser Asp Tyr Met Asn Met Thr
1               5                   10                  15
Pro Arg Arg Pro Gly Pro Thr Arg Lys His Tyr Gln Pro Tyr Ala Pro
            20                  25                  30
Pro Arg Asp Phe Ala Ala Tyr Arg Ser
        35                  40

<210> SEQ ID NO 13
<211> LENGTH: 123
<212> TYPE: DNA
<213> ORGANISM: Artificial Sequence
<220> FEATURE:
<223> OTHER INFORMATION: Synthetic Construct

<400> SEQUENCE: 13
aggagtaaga ggagcaggct cctgcacagt gactacatga acatgactcc ccgccgcccc     60
gggcccaccc gcaagcatta ccagccctat gccccaccac gcgacttcgc agcctatcgc    120
tcc                                                                  123

<210> SEQ ID NO 14
<211> LENGTH: 112
<212> TYPE: PRT
<213> ORGANISM: Artificial Sequence
<220> FEATURE:
<223> OTHER INFORMATION: Synthetic Construct

<400> SEQUENCE: 14

Arg Val Lys Phe Ser Arg Ser Ala Asp Ala Pro Ala Tyr Gln Gln Gly
1               5                   10                  15
Gln Asn Gln Leu Tyr Asn Glu Leu Asn Leu Gly Arg Arg Glu Glu Tyr
            20                  25                  30
Asp Val Leu Asp Lys Arg Arg Gly Arg Asp Pro Glu Met Gly Gly Lys
        35                  40                  45
Pro Arg Arg Lys Asn Pro Gln Glu Gly Leu Tyr Asn Glu Leu Gln Lys
    50                  55                  60
Asp Lys Met Ala Glu Ala Tyr Ser Glu Ile Gly Met Lys Gly Glu Arg
65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
            100                 105                 110

<210> SEQ ID NO 15
<211> LENGTH: 339
<212> TYPE: DNA
<213> ORGANISM: Artificial Sequence
<220> FEATURE:
<223> OTHER INFORMATION: Synthetic Construct

<400> SEQUENCE: 15
agagtgaagt tcagcaggag cgcagacgcc cccgcgtacc agcagggcca gaaccagctc     60
tataacgagc tcaatctagg acgaagagag gagtacgatg ttttggacaa gagacgtggc    120
cgggaccctg agatgggggg aaagccgaga aggaagaacc ctcaggaagg cctgtacaat    180
gaactgcaga agataagat ggcggaggcc tacagtgaga ttgggatgaa aggcgagcgc    240
cggaggggca agggcacga tggcctttac cagggtctca gtacagccac caaggacacc    300
tacgacgccc ttcacatgca ggccctgccc cctcgctaa                         339

<210> SEQ ID NO 16
<211> LENGTH: 15
<212> TYPE: DNA
<213> ORGANISM: Artificial Sequence
<220> FEATURE:
<223> OTHER INFORMATION: Synthetic Construct

<400> SEQUENCE: 16
ggggsggggs ggggs                                                    15

<210> SEQ ID NO 17
<211> LENGTH: 242
<212> TYPE: PRT
<213> ORGANISM: Artificial Sequence
<220> FEATURE:
<223> OTHER INFORMATION: Synthetic Construct

<400> SEQUENCE: 17

Ser Gln Val Gln Leu Gln Gln Pro Gly Ala Glu Leu Val Arg Pro Gly
1               5                   10                  15

Ala Ser Val Lys Leu Ser Cys Lys Ala Ser Gly Tyr Ser Phe Thr Thr
            20                  25                  30

Tyr Trp Met Asn Trp Val Lys Gln Arg Pro Gly Gln Gly Leu Glu Trp
        35                  40                  45

Ile Gly Met Ile His Pro Ser Asp Ser Glu Thr Arg Leu Asn Gln Lys
    50                  55                  60

Phe Lys Asp Lys Ala Thr Leu Thr Val Asp Lys Ser Ser Ser Thr Ala
65                  70                  75                  80

Tyr Met Gln Leu Ser Ser Pro Thr Ser Glu Asp Ser Ala Val Tyr Tyr
                85                  90                  95

Cys Ala Arg Ser Thr Met Ile Ala Thr Arg Ala Met Asp Tyr Trp Gly
            100                 105                 110

Gln Gly Thr Ser Val Thr Val Ser Gly Gly Gly Gly Ser Gly Gly Gly
        115                 120                 125

Gly Ser Gly Gly Gly Gly Ser Asp Ile Val Met Thr Gln Ser Gln Lys
    130                 135                 140

Ser Met Ser Thr Ser Val Gly Asp Arg Val Ser Ile Thr Cys Lys Ala
145                 150                 155                 160

Ser Gln Asp Val Ile Thr Gly Val Ala Trp Tyr Gln Gln Lys Pro Gly
                165                 170                 175

Gln Ser Pro Lys Leu Leu Ile Tyr Ser Ala Ser Tyr Arg Tyr Thr Gly
            180                 185                 190

Val Pro Asp Arg Phe Thr Gly Ser Gly Ser Gly Thr Asp Phe Thr Phe
        195                 200                 205

Thr Ile Ser Asn Val Gln Ala Glu Asp Leu Ala Val Tyr Tyr Cys Gln
    210                 215                 220

Gln His Tyr Ser Thr Pro Leu Thr Phe Gly Ala Gly Thr Lys Leu Glu
225                 230                 235                 240

Leu Lys

<210> SEQ ID NO 18
<211> LENGTH: 726
<212> TYPE: DNA
<213> ORGANISM: Artificial Sequence
<220> FEATURE:

<223> OTHER INFORMATION: Synthetic Construct

<400> SEQUENCE: 18

```
tcccaggtcc aactgcagca gcctggggct gagctggtga ggcctggagc ttcagtgaag     60
ctgtcctgca aggcttcggg gtactccttc accacctact ggatgaactg ggtgaagcag    120
aggcctggac aaggccttga gtggattggc atgattcatc cttccgatag tgaaactagg    180
ttaaatcaga agttcaagga caaggccaca ttgactgtag acaaatcctc cagcacagcc    240
tacatgcaac tcagcagccc gacatctgag gactctgcgg tctattactg tgcaagatct    300
actatgattg cgacgagggc tatggactac tggggtcaag aacctcagt caccgtctcc     360
ggcggtggcg ttctggtgg cggtggctcc ggcggtggcg ttctgacat tgtgatgacc      420
cagtctcaga atccatgtc cacatcagta ggagacaggg tcagcatcac ctgcaaggcc     480
agtcaggatg ttattactgg tgtagcctgg tatcaacaga accagggca atctcctaaa    540
ttactgattt actcggcatc ctaccggtac actggagtcc ctgatcgctt cactggcagt    600
ggatctggga cggatttcac tttcaccatc agcaatgtgc aggctgaaga cctggcagtt    660
tattactgtc agcaacatta tagtactcct ctcactttcg gtgctgggac caagctggag    720
ctgaaa                                                              726
```

<210> SEQ ID NO 19
<211> LENGTH: 107
<212> TYPE: PRT
<213> ORGANISM: Artificial Sequence
<220> FEATURE:
<223> OTHER INFORMATION: Synthetic Construct

<400> SEQUENCE: 19

```
Asp Ile Val Met Thr Gln Ser Gln Lys Ser Met Ser Thr Ser Val Gly
  1               5                  10                  15

Asp Arg Val Ser Ile Thr Cys Lys Ala Ser Gln Asp Val Ile Thr Gly
             20                  25                  30

Val Ala Trp Tyr Gln Gln Lys Pro Gly Gln Ser Pro Lys Leu Leu Ile
         35                  40                  45

Tyr Ser Ala Ser Tyr Arg Tyr Thr Gly Val Pro Asp Arg Phe Thr Gly
     50                  55                  60

Ser Gly Ser Gly Thr Asp Phe Thr Phe Thr Ile Ser Asn Val Gln Ala
 65                  70                  75                  80

Glu Asp Leu Ala Val Tyr Tyr Cys Gln Gln His Tyr Ser Thr Pro Leu
                 85                  90                  95

Thr Phe Gly Ala Gly Thr Lys Leu Glu Leu Lys
            100                 105
```

<210> SEQ ID NO 20
<211> LENGTH: 119
<212> TYPE: PRT
<213> ORGANISM: Artificial Sequence
<220> FEATURE:
<223> OTHER INFORMATION: Synthetic Construct

<400> SEQUENCE: 20

```
Glu Val Lys Leu Leu Glu Ser Gly Gly Gly Leu Val Gln Pro Gly Gly
  1               5                  10                  15

Ser Leu Lys Leu Ser Cys Ala Ala Ser Gly Phe Asp Phe Ser Arg Tyr
             20                  25                  30

Trp Met Ser Trp Val Arg Gln Ala Pro Gly Lys Gly Leu Glu Trp Ile
         35                  40                  45
```

```
Gly Glu Ile Asn Pro Asp Ser Ser Thr Ile Asn Tyr Thr Pro Ser Leu
        50                  55                  60

Lys Asp Lys Phe Ile Ile Ser Arg Asp Asn Ala Lys Asn Thr Leu Tyr
 65                  70                  75                  80

Leu Gln Met Ser Lys Val Arg Ser Glu Asp Thr Ala Leu Tyr Tyr Cys
                85                  90                  95

Ala Arg Pro Asp Gly Asn Tyr Trp Tyr Phe Asp Val Trp Gly Ala Gly
                100                 105                 110

Thr Thr Val Thr Val Ser Ser
            115

<210> SEQ ID NO 21
<211> LENGTH: 107
<212> TYPE: PRT
<213> ORGANISM: Artificial Sequence
<220> FEATURE:
<223> OTHER INFORMATION: Synthetic Construct

<400> SEQUENCE: 21

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Gly Ile Ala
                20                  25                  30

Val Ala Trp Tyr Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
                100                 105

<210> SEQ ID NO 22
<211> LENGTH: 121
<212> TYPE: PRT
<213> ORGANISM: Artificial Sequence
<220> FEATURE:
<223> OTHER INFORMATION: Synthetic Construct

<400> SEQUENCE: 22

Gln Val Gln Leu Gln Gln Ser Gly Ala Glu Leu Ala Arg Pro Gly Ala
 1               5                  10                  15

Ser Val Lys Leu Ser Cys Lys Ala Ser Gly Tyr Thr Phe Thr Ser Tyr
                20                  25                  30

Trp Met Gln Trp Val Lys Gln Arg Pro Gly Gln Gly Leu Glu Trp Ile
            35                  40                  45

Gly Ala Ile Tyr Pro Gly Asp Gly Asp Thr Arg Tyr Thr Gln Lys Phe
 50                  55                  60

Lys Gly Lys Ala Thr Leu Thr Ala Asp Lys Ser Ser Ser Thr Ala Tyr
 65                  70                  75                  80

Met Gln Leu Ser Ser Leu Ala Ser Glu Asp Ser Ala Val Tyr Tyr Cys
                85                  90                  95

Ala Arg Gly Lys Val Tyr Tyr Gly Ser Asn Pro Phe Ala Tyr Trp Gly
                100                 105                 110

Gln Gly Thr Leu Val Thr Val Ser Ala
```

<210> SEQ ID NO 23
<211> LENGTH: 107
<212> TYPE: PRT
<213> ORGANISM: Artificial Sequence
<220> FEATURE:
<223> OTHER INFORMATION: Synthetic Construct

<400> SEQUENCE: 23

```
Asp Ile Gln Met Thr Gln Ser Ser Ser Tyr Leu Ser Val Ser Leu Gly
1               5                   10                  15
Gly Arg Val Thr Ile Thr Cys Lys Ala Ser Asp His Ile Asn Asn Trp
            20                  25                  30
Leu Ala Trp Tyr Gln Gln Lys Pro Gly Asn Ala Pro Arg Leu Leu Ile
        35                  40                  45
Ser Gly Ala Thr Ser Leu Glu Thr Gly Val Pro Ser Arg Phe Ser Gly
    50                  55                  60
Ser Gly Ser Gly Lys Asp Tyr Thr Leu Ser Ile Thr Ser Leu Gln Thr
65                  70                  75                  80
Glu Asp Val Ala Thr Tyr Tyr Cys Gln Gln Tyr Trp Ser Thr Pro Trp
                85                  90                  95
Thr Phe Gly Gly Gly Thr Lys Leu Glu Ile Lys
            100                 105
```

<210> SEQ ID NO 24
<211> LENGTH: 120
<212> TYPE: PRT
<213> ORGANISM: Artificial Sequence
<220> FEATURE:
<223> OTHER INFORMATION: Synthetic Construct

<400> SEQUENCE: 24

```
Gln Val Gln Leu Gln Gln Ser Gly Pro Glu Leu Val Lys Pro Gly Ala
1               5                   10                  15
Ser Val Lys Ile Ser Cys Lys Ala Ser Gly Tyr Ala Phe Ser Ser Ser
            20                  25                  30
Trp Met Asn Trp Val Lys Gln Arg Pro Gly Gln Gly Leu Glu Trp Ile
        35                  40                  45
Gly Arg Ile Tyr Pro Gly Asp Gly Asp Thr Lys Tyr Asn Gly Lys Phe
    50                  55                  60
Lys Gly Lys Ala Thr Leu Thr Ala Asp Lys Ser Ser Ser Thr Ala Tyr
65                  70                  75                  80
Met Gln Leu Ser Ser Leu Thr Ser Val Asp Ser Ala Val Tyr Phe Cys
                85                  90                  95
Ala Arg Ser Thr Met Ile Ala Thr Gly Ala Met Asp Tyr Trp Gly Gln
            100                 105                 110
Gly Thr Ser Val Thr Val Ser Ser
        115                 120
```

<210> SEQ ID NO 25
<211> LENGTH: 107
<212> TYPE: PRT
<213> ORGANISM: Artificial Sequence
<220> FEATURE:
<223> OTHER INFORMATION: Synthetic Construct

<400> SEQUENCE: 25

```
Glu Thr Thr Val Thr Gln Ser Pro Ala Ser Leu Ser Met Ala Ile Gly
1               5                   10                  15
```

Glu Lys Val Thr Ile Arg Cys Ile Thr Ser Thr Asp Ile Asp Asp
            20                  25                  30

Met Asn Trp Tyr Gln Gln Lys Pro Gly Glu Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Leu
                85                  90                  95

Thr Phe Gly Gly Gly Thr Lys Leu Glu Ile Lys
            100                 105

<210> SEQ ID NO 26
<211> LENGTH: 119
<212> TYPE: PRT
<213> ORGANISM: Artificial Sequence
<220> FEATURE:
<223> OTHER INFORMATION: Synthetic Construct

<400> SEQUENCE: 26

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Lys Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Ser Thr Met Ile Ala Thr Gly Ala Met Asp Tyr Trp Gly Gln
            100                 105                 110

Gly Thr Ser Val Thr Val Ser
        115

<210> SEQ ID NO 27
<211> LENGTH: 108
<212> TYPE: PRT
<213> ORGANISM: Artificial Sequence
<220> FEATURE:
<223> OTHER INFORMATION: Synthetic Construct

<400> SEQUENCE: 27

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Pro

```
                    85                  90                  95
Tyr Thr Phe Gly Gly Gly Thr Lys Leu Glu Ile Lys
                100                 105

<210> SEQ ID NO 28
<211> LENGTH: 459
<212> TYPE: PRT
<213> ORGANISM: Artificial Sequence
<220> FEATURE:
<223> OTHER INFORMATION: Synthetic Construct

<400> SEQUENCE: 28

Met Gly Trp Ser Ser Ile Ile Leu Phe Leu Val Ala Thr Ala Thr Gly
1               5                   10                  15

Val His Ser Gln Val Gln Leu Gln Gln Pro Gly Ala Glu Leu Val Arg
                20                  25                  30

Pro Gly Ala Ser Val Lys Leu Ser Cys Lys Ala Ser Gly Tyr Ser Phe
            35                  40                  45

Thr Thr Tyr Trp Met Asn Trp Val Lys Gln Arg Pro Gly Gln Gly Leu
        50                  55                  60

Glu Trp Ile Gly Met Ile His Pro Ser Asp Ser Glu Thr Arg Leu Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Ala Arg Ser Thr Met Ile Ala Thr Arg Ala Met Asp Tyr
        115                 120                 125

Trp Gly Gln Gly Thr Ser Val Thr Val Ser Gly Gly Gly Ser Gly
    130                 135                 140

Gly Gly Gly Ser Gly Gly Gly Ser Asp Ile Val Met Thr Gln Ser
145                 150                 155                 160

Gln Lys Ser Met Ser Thr Ser Val Gly Asp Arg Val Ser Ile Thr Cys
                165                 170                 175

Lys Ala Ser Gln Asp Val Ile Thr Gly Val Ala Trp Tyr Gln Gln Lys
            180                 185                 190

Pro Gly Gln Ser Pro Lys Leu Leu Ile Tyr Ser Ala Ser Tyr Arg Tyr
        195                 200                 205

Thr Gly Val Pro Asp Arg Phe Thr Gly Ser Gly Ser Gly Thr Asp Phe
    210                 215                 220

Thr Phe Thr Ile Ser Asn Val Gln Ala Glu Asp Leu Ala Val Tyr Tyr
225                 230                 235                 240

Cys Gln Gln His Tyr Ser Thr Pro Leu Thr Phe Gly Ala Gly Thr Lys
                245                 250                 255

Leu Glu Leu Lys Leu Glu Pro Lys Ser Cys Asp Lys Thr His Thr Cys
            260                 265                 270

Pro Pro Cys Pro Asp Pro Lys Phe Trp Val Leu Val Val Val Gly Gly
        275                 280                 285

Val Leu Ala Cys Tyr Ser Leu Leu Val Thr Val Ala Phe Ile Ile Phe
    290                 295                 300

Trp Val Arg Ser Lys Arg Ser Arg Leu Leu His Ser Asp Tyr Met Asn
305                 310                 315                 320

Met Thr Pro Arg Arg Pro Gly Pro Thr Arg Lys His Tyr Gln Pro Tyr
                325                 330                 335

Ala Pro Pro Arg Asp Phe Ala Ala Tyr Arg Ser Arg Val Lys Phe Ser
```

```
                    340                 345                 350
Arg Ser Ala Asp Ala Pro Ala Tyr Gln Gln Gly Gln Asn Gln Leu Tyr
            355                 360                 365

Asn Glu Leu Asn Leu Gly Arg Arg Glu Glu Tyr Asp Val Leu Asp Lys
        370                 375                 380

Arg Arg Gly Arg Asp Pro Glu Met Gly Gly Lys Pro Arg Arg Lys Asn
385                 390                 395                 400

Pro Gln Glu Gly Leu Tyr Asn Glu Leu Gln Lys Asp Lys Met Ala Glu
                405                 410                 415

Ala Tyr Ser Glu Ile Gly Met Lys Gly Glu Arg Arg Arg Gly Lys Gly
            420                 425                 430

His Asp Gly Leu Tyr Gln Gly Leu Ser Thr Ala Thr Lys Asp Thr Tyr
        435                 440                 445

Asp Ala Leu His Met Gln Ala Leu Pro Pro Arg
    450                 455

<210> SEQ ID NO 29
<211> LENGTH: 1380
<212> TYPE: DNA
<213> ORGANISM: Artificial Sequence
<220> FEATURE:
<223> OTHER INFORMATION: Synthetic Construct

<400> SEQUENCE: 29
atgggatgga gctctatcat cctcttcttg gtagcaacag ctacaggtgt ccactcccag     60
gtccaactgc agcagcctgg ggctgagctg gtgaggcctg gagcttcagt gaagctgtcc    120
tgcaaggctt cggggtactc cttcaccacc tactggatga actgggtgaa gcagaggcct    180
ggacaaggcc ttgagtggat tggcatgatt catccttccg atagtgaaac taggttaaat    240
cagaagttca aggacaaggc cacattgact gtagacaaat cctccagcac agcctacatg    300
caactcagca gcccgacatc tgaggactct gcggtctatt actgtgcaag atctactatg    360
attgcgacga gggctatgga ctactggggt caaggaacct cagtcaccgt ctccggcggt    420
ggcggttctg gtggcggtgg ctccggcggt ggcggttctg acattgtgat gacccagtct    480
cagaaatcca tgtccacatc agtaggagac agggtcagca tcacctgcaa ggccagtcag    540
gatgttatta ctggtgtagc ctggtatcaa cagaaaccag gcaatctcc taaattactg    600 atttactcgg catcctaccg gtacactgga gtccctgatc gcttcactgg cagtggatct    660
gggacggatt tcactttcac catcagcaat gtgcaggctg aagacctggc agtttattac    720
tgtcagcaac attatagtac tcctctcact ttcggtgctg ggaccaagct ggagctgaaa    780
ctcgagccca atcttgtga caaaactcac acatgcccac cgtgcccgga tcccaaattt    840
tgggtgctgg tggtgttgg tggagtcctg gcttgctata gcttgctagt aacagtggcc    900
tttattattt tctgggtgag gagtaagagg agcaggctcc tgcacagtga ctacatgaac    960
atgactcccc gccgccccgg gcccacccgc aagcattacc agccctatgc cccaccacgc   1020
gacttcgcag cctatcgctc cagagtgaag ttcagcagga gcgcagacgc cccgcgtac   1080 cagcagggcc agaaccagct ctataacgag ctcaatctag acgaagaga ggagtacgat   1140 gtttggaca agagacgtgg ccgggaccct gagatggggg gaaagccgag aaggaagaac   1200
cctcaggaag gcctgtacaa tgaactgcag aaagataaga tggcggaggc ctacagtgag   1260
attgggatga aggcgagcg ccggagggc aaggggcacg atggccttta ccagggtctc   1320
agtacagcca ccaaggacac ctacgacgcc cttcacatgc aggccctgcc ccctcgctaa   1380
```

CS1-SPECIFIC CHIMERIC ANTIGEN RECEPTOR ENGINEERED IMMUNE EFFECTOR CELLS

CROSS-REFERENCE TO RELATED APPLICATIONS

This application claims benefit of U.S. Provisional Application No. 61/819,141, filed May 3, 2013, and U.S. Provisional Application No. 61/876,492, filed Sep. 11, 2013, which are hereby incorporated herein by reference in their entirety.

REFERENCE TO SEQUENCE LISTING

The Sequence Listing submitted Nov. 3, 2015, as a text file named "10336-088US1 2015_11_03 Sequence_Listing_ST25.txt," created on Nov. 3, 2015, and having a size of 25,185 bytes is hereby incorporated by reference pursuant to 37 C.F.R. § 1.52(e)(5).

BACKGROUND

Multiple myeloma (MM) is a B-cell malignancy characterized by the aberrant clonal expansion of plasma cells (PCs) within the bone marrow, with an estimated 21,700 new cases and 10,710 deaths from MM identified in the United States in 2012 (Siegel R, et al. Cancer J Clin 2012 62:10-29). In 2013, it has been estimated that 22,350 individuals will be newly diagnosed with MM in the United States and 10,710 people will die from it, accounting for 20% of the deaths from all hematologic malignancies. Despite the use of proteasome inhibitors and immune-modulating drugs, which have improved overall survival (Palumbo A, et al. Leukemia 2009 23:449-456), MM remains an incurable malignancy (Podar K, et al. Leukemia 2009 23:10-24) for which novel therapeutic approaches are urgently needed.

SUMMARY

Disclosed herein are chimeric antigen receptor (CAR) polypeptides that can be used with adoptive cell transfer to target and kill multiple myeloma (MM) cells. The cell surface glycoprotein CS1 is highly and ubiquitously expressed on the surface of myeloma cells while being expressed at very low levels in the majority of immune effector cells. Therefore, the disclosed CAR polypeptides contain in an ectodomain an anti-CS1 binding agent that can bind CS1-expressing MM cells. As with other CARs, the disclosed polypeptides can also contain a transmembrane domain and an endodomain capable of activating an immune effector cell. For example, the endodomain can contain an intracellular signaling domain and optionally a co-stimulatory signaling region.

The anti-CS1 binding agent is in some embodiments an antibody fragment or an antigen-binding fragment that specifically binds CS1. For example, the antigen binding domain can be a Fab or a single-chain variable fragment (scFv) of an antibody that specifically binds CS1. The anti-CS1 binding agent is in some embodiments an aptamer that specifically binds CS1. For example, the anti-CS1 binding agent can be a peptide aptamer selected from a random sequence pool based on its ability to bind CS1. The anti-CS1 binding agent can also be a natural ligand of CS1, or a variant and/or fragment thereof capable of binding CS1.

In some embodiments, the intracellular signaling domain is a CD3 zeta (CD3ζ) signaling domain, and the costimulatory signaling region comprises the cytoplasmic domain of CD28, 4-1BB, or a combination thereof. In some cases, the costimulatory signaling region contains 1, 2, 3, or 4 cytoplasmic domains of one or more intracellular signaling and/or costimulatory molecules.

Also disclosed are isolated nucleic acid sequences encoding the disclosed CAR polypeptides, vectors comprising these isolated nucleic acids, and cells containing these vectors. For example, the cell can be an immune effector cell selected from the group consisting of a T cell, a Natural Killer (NK) cell, a cytotoxic T lymphocyte (CTL), and a regulatory T cell. In some embodiments, the cell exhibits an anti-tumor immunity when the antigen binding domain of the CAR binds to CS1.

Also disclosed is a method of providing an anti-tumor immunity in a subject with multiple myeloma (MM) that involves administering to the subject an effective amount of an immune effector cell genetically modified with a disclosed CS1-specific CAR.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a schematic diagram of a Pinco-CS1-CAR retroviral construct containing a scFv against CS1 linked to CD28 and CD3ζ endodomains. LTR, long terminal repeat; SP, signal peptide; VH, variable H chain; L, linker; VL, variable L chain. In FIG. 1B, PBMC (peripheral blood mononuclear cells) were activated with CD3 and CD28 beads and transduced with the Pinco-CS1-CAR or Pinco construct. GFP-positive cells were sorted, and cell lysates were subjected to immunoblot analysis under reducing conditions with anti-human CD3ζ primary antibody. In FIG. 1C, mock1- or CS1-CAR1-transduced T cells from healthy donors were stained with biotin-labeled goat anti-mouse Fab-specific or isotype-matched control antibody, followed by streptavidin and CD3 antibody staining.

FIG. 2A shows flow cytometric analysis of CS1 expression on the surface of myeloma cell lines. The four myeloma cell lines indicated were stained with PE-conjugated anti-CS1 mAb antibody (solid line) or isotype-matched control antibody (dotted line). FIGS. 2B and 2C are bar graphs showing IFN-γ (FIG. 2B, ng/ml) and IL-2 (FIG. 2C, pg/ml) secretion in mock- or CS1-CAR-transduced healthy donor T cells ($2\times10^5$) that were cultured alone (no target) or stimulated with an equal number of myeloma cells expressing different levels of CS1 for 24 hours.

FIGS. 3A to 3D show CS1-redirected T cells preferentially eradicate myeloma cells obviously expressing CS1 protein. In FIG. 3A, $^{51}$Cr-labeled NCI-H929, IM9, MM.1S, and RPMI-8226 myeloma cells ($5\times10^3$) were cocultured with mock- or CS1-CAR-transduced T cells at the indicated E/T ratios for 4 hours, and target lysis ($^{51}$Cr release) was measured. In FIG. 3B, expression of the degranulation marker CD107a and the T-cell activation marker CD69 on mock- or CS1-CAR transduced T cells were evaluated by flow cytometry following 4 hours co-culture with NCI-H929 cells. Compared with mock-transduced T cells, CS1-CAR-transduced T cells displayed superior degranulation and higher T-cell activation in response to CS1-expressing NCI-H929 cells. In FIG. 3C, Mock- and CS1-CAR-transduced T cells were permeabilized for intracellular staining with mAb specific for granzyme B and perforin, and analyzed by flow cytometry.

FIG. 4A shows flow cytometric staining for CS1 protein or IgG isotype control (dotted line) on the surface of RPMI-8226 cells overexpressing CS1 (RPMI-8226-CS1, solid heavy line) or an empty vector control (RPMI-8226-PCDH, solid light line). FIG. 4B is a graph showing cytotoxicity of mock- or CS1-CAR-transduced T cells against RPMI-8226-CS1 and RPMI-8226-PCDH cells. RPMI-8226-CS1 and RPMI-8226-PCDH cells were incubated with mock- or CS1-CAR-transduced T cells at indicated E/T ratios for 4 hours, and specific lysis was determined using a standard $^{51}$Cr release assay. FIGS. 4C and 4D are bar graphs showing IFN-γ (FIG. 4C, pg/ml) and IL-2 (FIG. 4D, pg/ml) secretion in mock- or CS1-CAR-transduced T cells ($1\times10^5$) cultured alone or stimulated with an equal number of either RPMI-8226-CS1 or RPMI-8226-PCDH cells.

FIG. 5A shows flow cytometric results of PBMCs from patients with MM that were activated with anti-CD3 and anti-CD28 beads, transduced with the Pinco-CS1-CAR or Pinco construct (mock), and stained with anti-mouse Fab and anti-humanCD3 antibodies. Results from 1 of 4 patients with similar data are shown. FIG. 5B shows flow cytometric staining for CS1 protein in CD138$^+$ myeloma cells freshly isolated from patients with MM. Results from 3 of 10 patients with similar data are shown. FIG. 5C is a series of graphs showing specific lysis ($^{51}$Cr release assay) of the CD138$^+$ myeloma cells in (B) co-cultured with the autologous mock- or CS1-CAR-transduced T cells in (A) at indicated E/T ratios for 4 hours. FIG. 5D is a bar graph showing IFN-γ secretion (pg/ml) by the cells treated as in (C) except that the E/T ratio was 1:1 and the incubation time was extended to 24 hours.

FIG. 6A is a series of dorsal and ventral bioluminescence images of five representative mice bearing MM.1S tumors from each indicated group. NSG mice were intravenously inoculated with $8\times10^6$ MM.1S cells expressing luciferase (day 0). On days 7 and 14 after inoculation, each mouse received PBS (placebo control group), $10\times10^6$ mock T cells (mock control group) or CS1-CAR T cells (CAR treatment group). FIG. 6B shows Kaplan-Meier survival curves of MM.1S bearing mice treated with PBS, mock T cells, or CS1-CART cells.

FIG. 7A shows that 293T parental cells were negative for CS1 expression. 293T cells were stained with PE-conjugated anti-CS1 mAb antibody (solid line) or isotype-matched control Ab (dotted line) and analyzed by flow cytometry. FIG. 7B shows flow cytometric staining for CS1 protein on the surface of 293T cells overexpressing CS1 (293T-CS1, dark solid heavy line) or an empty vector (293T-PCDH, gray solid heavy line). 293 T cells expressing CS1 stained with IgG isotype (dotted line) served as non-specific binding control. FIG. 7C shows cytotoxicity of mock- or CS1-CAR-transduced T cells against 293T-CS1 and 293T-PCDH cells. 293T-CS1 and 293T-PCDH cells were incubated with mock- or CS1-CAR-transduced T cells at indicated E/T ratios for 4 h, and specific lysis was determined using a standard $^{51}$Cr release assay. FIGS. 7D and 7E are a bar graph showing IFN-γ secretion (FIG. 7D, pg/ml) or IL-2 secretion (FIG. 7E, pg/ml) by Mock- or CS1-CAR-transduced T cells cultured alone or stimulated with either 293T-CS1 or 293T-PCDH cells.

In FIG. 8A, Mock- or CS1-CAR-transduced T cells were cultured alone or stimulated with NCI-H929 and MM.1S cells for 12 h, then surface expression of CD3 and CD8, as well as intracellular IFN-γ, were evaluated by flow cytometry. The plots were gated on CD3+ lymphocytes. One representative experiment out of three with similar results is shown. In FIG. 8B, Mock- or CS1-CAR-transduced T cells were cultured alone or stimulated with NCI-H929 and MM.1S cells for 4 h, and expression of CD3, CD8 and the degranulation marker CD107a were evaluated by flow cytometry. The plots were gated on live CD3$^+$ lymphocytes. One representative experiment out of three with similar results is shown.

FIG. 9A show dorsal and ventral bioluminescence images of five representative mice bearing IM9 tumors from each indicated group. NSG mice were i.v. inoculated with $5\times10^5$ IM9 cells expressing luciferase (day 0). On day 7 and day 21 after inoculation, each mouse received PBS (placebo control group), $10\times10^6$ mock T cells (mock control group) or CS1-CART cells (CAR treatment group). The white crosses "+" represent mice that died of MM disease in the PBS-treated group at the time of imaging. FIG. 9B are Kaplan-Meier survival curves of IM9-bearing mice treated with PBS, mock T cells or CS1-CAR T cells.

FIG. 10A shows the percentage of human T cells (CD45$^+$/CD3$^+$) in the BM of representative mice. In FIG. 10B, the gated human T cells (CD45$^+$/CD3$^+$) were stained with IgG (left panel) or anti-Fab Ab (right panel) to verify CAR expression. In FIG. 10C, the gated human T cells (CD45$^+$/CD3$^+$) were stained with IgG (left panel) or anti-Brdu Ab, and the percentage of Brdu-incorporated T cells are displayed.

FIGS. 11A to 11C shows CS1-CAR T cells displayed low levels of reactivity against primary NK and T cells. $^{51}$Cr-labeled human primary NK and T cells ($5\times10^3$) were co-cultured with mock- or CS1-CAR-transduced T cells at the indicated Effector/Target (E/T) ratios for 4 h, and target lysis ($^{51}$Cr release) of NK cells (FIG. 11A) and T cells (FIG. 11B) was measured. FIG. 11C is a bar graph showing IFN-γ secretion by Mock- or CS1-CAR-transduced T cells cultured alone or stimulated with either primary NK cells, T cells or myeloma cells for 24 h.

FIG. 13A is a schematic representation of the CS1-CAR lentiviral construct. FIG. 13B shows Western blotting analysis of CS1-CAR expression using a CD3ζ-specific Ab. Data shown are representative of three experiments with similar results. FIG. 13C shows expression of chimeric CS1 scFv on the surface of FACS-sorted NK-92 and NKL cells transduced with the CS1-CAR construct or empty vector (EV) analyzed by flow cytometry after cells were stained with an anti-myc antibody or an IgG1 isotype control. Data shown are representative of three experiments with similar results.

FIG. 14A shows determination of CS1 expression on the surface of L363, IM9 and U266 MM cell lines by flow cytometry after cells were stained with anti-CS1 mAb or isotype-matched control antibody. FIGS. 14B to 13D show cytotoxic activity of mock-transduced or CS1-CAR-transduced NK-92 or NKL cells against IM9 (FIG. 14B), L363 (FIG. 14C) and U266 (FIG. 13D) cells using a standard $^{51}$Cr release assay. NK-92-EV and NKL-EV indicate empty vector (EV) control-transduced NK-92 and NKL cells, respectively. NK-92-CS1-CAR and NKL-CS1-CAR indicate transduction of NK-92 and NKL cells, respectively, with a CS1-CAR construct. * and ** indicate P<0.05 and P<0.01, respectively.

FIGS. 15A to 15C are bar graphs showing IFN-γ secretion by Mock-transduced or CS1-CAR transduced NK-92 or NKL effector cells co-cultured with an equal number of IM9 (FIG. 15A), L363 (FIG. 15B) or U266 (FIG. 15C) myeloma cells for 24 h. NK-92-EV and NKL-EV indicate empty vector (EV) control-transduced NK-92 and NKL cells, respectively. NK-92-CS1-CAR and NKL-CS1-CAR indicate transduction of NK-92 and NKL cells, respectively, with a CS1-CAR construct.

FIGS. 16A to 16C show enhanced target recognition of NK-92-CS1-CAR cells depends on expression of CS1 on MM cells. FIG. 16A shows flow cytometric staining for a CS1 protein or an IgG control (dotted line) on the surface of U266 cells overexpressing CS1 (U266-CS1, solid heavy line) or an empty vector control (U266-Vector, solid light line). FIG. 16B shows cytotoxicity of mock- or CS1-CAR-transduced NK-92 cells (NK-92-EV and NK-92-CS1-CAR, respectively) against U266-Vector and U266-CS1 cells. U266-Vector or U266-CS1 cells were incubated with NK-92-CS1-CAR or NK-92-EV cells at different Effector/Target (E/T) ratios for 4 h. Specific lysis was determined using a standard $^{51}$Cr release assay. * indicates P<0.05. (c) NK-92-CS1-CAR or NK-92-EV cells were co-cultured with an equal number of U266-Vector or U266-CS1 myeloma cells for 24 h. Supernatants were then harvested for measurement of IFN-γ secretion using ELISA.

In FIG. 17A, Mock- or CS1-CAR-transduced NK-92 cells (NK-92-EV and NK-92-CS1-CAR, respectively) were either cultured alone, or cultured with IM9 MM cells for 4 h. Surface expression of NKp30, NKp46, NKG2C, NKG2D, CD69 and HLA-DR was assessed by flow cytometry following staining with the corresponding mAbs, and the mean fluorescence intensity (MFI) was recorded. * indicates P<0.05. In FIG. 17B, NK-92-EV and NK-92-CS1-CAR cells were permeabilized for intracellular staining with mAb specific for perforin or granzyme B, and analyzed by flow cytometry. The dashed line represents staining the NK-92-EV control cells with control IgG antibody, solid heavy line denotes staining NK-92-CS1-CAR cells with either Perforin or Granzyme B antibody, and the solid light line indicates staining the NK-92-EV control cells with either Perforin or Granzyme B antibody. FIG. 17C shows MFI for histograms shown in FIG. 17B. * indicates P<0.05.

FIG. 18A shows flow cytometric staining for CS1 protein or IgG isotype control, demonstrating that CD138$^+$ primary myeloma cells highly express CS1. The open and filled histograms represent staining with isotype-matched control antibodies and anti-CS1 antibodies, respectively. Data shown are representative of two out of six patient samples with similar results. FIG. 18B shows cytotoxic activity of mock- or CS1-CAR-transduced NK-92 cells (NK-92-EV and NK-92-CS1-CAR, respectively) against CD138$^+$ primary myeloma cells from three of six patients with similar results using a standard $^{51}$Cr release assay. E/T indicates the effector cell/target cell ratio. * indicates P<0.05. FIG. 18C shows IFN-γ secretion by CD138$^+$ primary myeloma cells co-cultured with NK-92-EV or NK-92-CS1-CAR cells at an E/T ratio of 5:1 for 24 h. Data shown are representative of one out of three patient samples with similar results.

FIG. 19A (left) is an image showing massive infiltration of human IM9 cells, detected by Hematoxylin-Eosin (H&E) staining, in the lumbar vertebrae bone lesions of one representative mouse displaying hind leg paralyses after i.v. injected with IM9 cells. FIG. 19A (right) shows immunohistochemical staining of mouse lumbar vertebrae bone lesions with anti-human CD138 mAb. FIG. 19B shows dorsal bioluminescence imaging of mice bearing IM9 tumors. NSG mice were inoculated with 5×10$^5$ luciferase-expressing IM9 cells via a tail vein injection (day 0). Seven days after inoculation, mice were treated with mock-transduced NK-92 cells (NK-92-EV), CS1-CAR transduced NK-92 cells (NK-92-CS1-CAR) or phosphate-buffered saline (a negative control). FIG. 19C is a bar graph showing quantification summary of units of photons per second per mouse from FIG. 19B. * indicates P<0.05; ** denotes P<0.01. FIG. 19D shows Kaplan-Meier survival curves of IM9-bearing mice treated with NK-92-CS1-CAR cells compared with the mice treated with NK-92-EV cells. * indicates P<0.05.

DETAILED DESCRIPTION

Figure 1A:
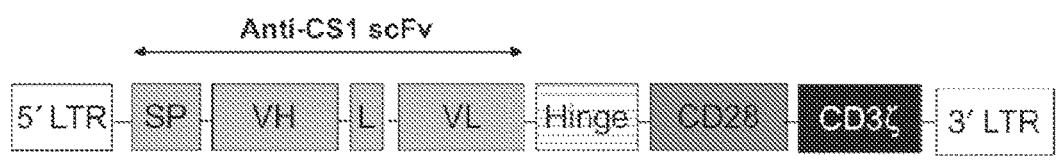
FIGS. 1A to 1C show the generation of a CS1-specific CAR and its expression in CAR-transduced T cells.

Disclosed herein are chimeric antigen receptors (CAR) that can specifically recognize tumor-associated antigens (TAA) on Multiple myeloma (MM) cells. Also disclosed are immune effector cells, such as T cells or Natural Killer (NK) cells, that are engineered to express these CARs. Therefore, also disclosed are methods for providing an anti-tumor immunity in a subject with MM that involves adoptive transfer of the disclosed immune effector cells engineered to express the disclosed CS1-specific CARs.

CS1-Specific Chimeric Antigen Receptors (CAR)

CARs generally incorporate an antigen recognition domain from the single-chain variable fragments (scFv) of a monoclonal antibody (mAb) with transmembrane signaling motifs involved in lymphocyte activation (Sadelain M, et al. Nat Rev Cancer 2003 3:35-45). The cell surface glycoprotein CS1 is highly and ubiquitously expressed on the surface of myeloma cells (Hsi E D, et al. Clin Cancer Res 2008 14:2775-84). CS1 is expressed at very low levels in the majority of immune effector cells, including natural killer (NK) cells, some subsets of T cells, and normal B cells, and is almost undetectable on myeloid cells (Hsi E D, et al. Clin Cancer Res 2008 14:2775-84). Notably, CS1 is negligibly expressed in human hematopoietic stem cells (Hsi E D, et al. Clin Cancer Res 2008 14:2775-84), which can be used for stem cell transplantation to treat hematologic malignancies, including MM. The functions of CS1 in MM remain incompletely understood, and it has been documented that CS1 may play a role in myeloma cell adhesion, clonogenic growth, and tumorigenicity (Benson D M Jr, et al. J Clin Oncol 2012 30:2013-5; Tai Y T, et al. Blood 2009 113:4309-18). Targeting CS1 with the humanized mAb elotuzumab has been demonstrated to be safe in the clinic (Benson D M Jr, et al. J Clin Oncol 2012 30:2013-5; Tai Y T, et al. Blood 2009 113:4309-18). Preclinical studies show that this antibody inhibits myeloma cell adhesion to bone marrow stromal cells, induces NK cell-mediated antibody-dependent cellular cytotoxicity, and eradicates the xenograft tumors initiated by human myeloma cells in immunodeficient mice (Benson D M Jr, et al. J Clin Oncol 2012 30:2013-5; Tai Y T, et al. Blood 2009 113:4309-18; Tai Y T, et al. Blood 2008 112:1329-37). Therefore, disclosed herein is a CS1-specific chimeric antigen receptor (CAR) that can be that can be expressed in immune effector cells to enhance antitumor activity against human multiple myeloma.

The disclosed CAR is generally made up of three domains: an ectodomain, a transmembrane domain, and an endodomain. The ectodomain comprises the CS1-binding region and is responsible for antigen recognition. It also generally contains a signal peptide (SP) so that the CAR can be glycosylated and anchored in the cell membrane of the immune effector cell. The transmembrane domain (TD), is as its name suggests, connects the ectodomain to the endodomain and resides within the cell membrane when expressed by a cell. The endodomain is the business end of the CAR that transmits an activation signal to the immune effector cell after antigen recognition. For example, the endodomain can contain an intracellular signaling domain (ISD) and optionally a co-stimulatory signaling region (CSR).

In some embodiments, the disclosed CAR is defined by the formula:

SP-CS1-HG-TM-CSR-ISD; or

SP-CS1-HG-TM-ISD-CSR wherein "SP" represents a signal peptide,
wherein "CS1" represents a CS1-binding region,
wherein "HG" represents an optional hinge domain,
wherein "TM" represents a transmembrane domain,
wherein "CSR" represents a co-stimulatory signaling region,
wherein "ISD" represents an intracellular signaling domain, and
wherein "-" represents a bivalent linker.

The antigen recognition domain of the disclosed CAR is usually an scFv. There are however many alternatives. An antigen recognition domain from native T-cell receptor (TCR) alpha and beta single chains have been described, as have simple ectodomains (e.g. CD4 ectodomain to recognize HIV infected cells) and more exotic recognition components such as a linked cytokine (which leads to recognition of cells bearing the cytokine receptor). In fact almost anything that binds a given target with high affinity can be used as an antigen recognition region.

The endodomain is the business end of the CAR that after antigen recognition (i.e., CS1) transmits a signal to the immune effector cell, activating at least one of the normal effector functions of the immune effector cell. Effector function of a T cell, for example, may be cytolytic activity or helper activity including the secretion of cytokines. Therefore, the endodomain may comprise the "intracellular signaling domain" of a T cell receptor (TCR) and optional co-receptors. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal.

Cytoplasmic signaling sequences that regulate primary activation of the TCR complex that act in a stimulatory manner may contain signaling motifs which are known as immunoreceptor tyrosine-based activation motifs (ITAMs). Examples of ITAM containing cytoplasmic signaling sequences include those derived from TCR zeta, FcR gamma, FcR beta, CD3 gamma, CD3 delta, CD3 epsilon, CD5, CD22, CD79a, CD79b, and CD66d. However, in preferred embodiments, the intracellular signaling domain is derived from CD3 zeta (CD3ζ).

T-cell surface glycoprotein CD3 zeta (CD3ζ) chain, also known as T-cell receptor T3 zeta chain or CD247 (Cluster of Differentiation 247), is a protein that in humans is encoded by the CD247 gene.

First-generation CARs typically had the intracellular domain from the CD3ζ chain, which is the primary transmitter of signals from endogenous TCRs. Second-generation CARs add intracellular signaling domains from various costimulatory protein receptors (e.g., CD28, 41BB, ICOS) to the endodomain of the CAR to provide additional signals to the T cell. Preclinical studies have indicated that the second generation of CAR designs improves the antitumor activity of T cells. More recent, third-generation CARs combine multiple signaling domains to further augment potency. T cells grafted with these CARs have demonstrated improved expansion, activation, persistence, and tumor-eradicating efficiency independent of costimulatory receptor/ligand interaction (Imai C, et al. Leukemia 2004 18:676-84; Maher J, et al. Nat Biotechnol 2002 20:70-5).

For example, the endodomain of the CAR can be designed to comprise the CD3ζ signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, ICOS, lymphocyte function-associated antigen-1 (LFA-1), CD2, CD7, LIGHT, NKG2C, B7-H3, and a ligand that specifically binds with CD83, and the like. Thus, while the CAR is exemplified primarily with CD28 as the co-stimulatory signaling element, other costimulatory elements can be used alone or in combination with other co-stimulatory signaling elements.

In some embodiments, the CAR comprises a hinge sequence. A hinge sequence is a short sequence of amino acids that facilitates antibody flexibility (see, e.g., Woof et al., Nat. Rev. Immunol., 4(2): 89-99 (2004)). The hinge sequence may be positioned between the antigen recognition moiety (e.g., an anti-CS1 scFv) and the transmembrane domain. The hinge sequence can be any suitable sequence derived or obtained from any suitable molecule. In some embodiments, for example, the hinge sequence is derived from a CD8a molecule or a CD28 molecule.

The transmembrane domain may be derived either from a natural or from a synthetic source. Where the source is natural, the domain may be derived from any membrane-bound or transmembrane protein. For example, the transmembrane region may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, or CD154. Alternatively the transmembrane domain may be synthetic, in which case it will comprise predominantly hydrophobic residues such as leucine and valine. In some cases, a triplet of phenylalanine, tryptophan and valine will be found at each end of a synthetic transmembrane domain. A short oligo- or polypeptide linker, such as between 2 and 10 amino acids in length, may form the linkage between the transmembrane domain and the endoplasmic domain of the CAR.

The bivalent linker can be any molecule suitable to link a compound or nucleic acid to a polynucleotide sequence. Methods and compositions for conjugating biomolecules, such as polynucleotides, are disclosed in G. T. Hermanon, Bioconjugate Techniques ($2^{nd}$ ed.), Academic Press (2008), which is incorporated by reference in its entirety for the teaching of these techniques. In some cases, the bivalent linker comprises one or more amino acids. However, it can also comprise a peptide bond directly linking the disclosed domains.

In some embodiments, the disclosed CS1-specific CAR comprises one or more of the SP, CS1, HG, TM, CSR, ISD, and/or linker components set forth in Table 1, or variants thereof having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to the sequences set forth in Table 1.

TABLE 1

Exemplary sequences for the different CAR CS1 components

| Functional domains | SEQ ID # | Amino Acid Sequence/ Nucleic Acid Sequence |
|---|---|---|
| SP | SEQ ID NO: 1 | MGWSSIILFLVATATGVH |
|  | SEQ ID NO: 2 | ATGGGATGGAGCTCTATCATCCTCTTCTTGGTAGCAA CAGCTACAGGTGTCCAC |
| CD8α SP | SEQ ID NO: 3 | MALPVTALLLPLALLLHAARP |
| Alternative SP | SEQ ID NO: 4 | METDTLLLWVLLLWVPGSTG |
| Hinge domain | SEQ ID NO: 5 | LEPKSCDKTHTCPPCP |
|  | SEQ ID NO: 6 | CTCGAGCCCAAATCTTGTGACAAAACTCACACATGC CCACCGTGCCCG |
| CD8α TM | SEQ ID NO: 7 | IYIWAPLAGTCGVLLLSLVITLYC |
| 41BB TM | SEQ ID NO: 8 | IISFFLALTSTALLFLLFFLTLRFSVV |
| CD28 TM | SEQ ID NO: 9 | FWVLVVVGGVLACYSLLVTVAFIIFWV |
|  | SEQ ID NO: 10 | TTTTGGGTGCTGGTGGTGGTTGGTGGAGTCCTGGCTT GCTATAGCTTGCTAGTAACAGTGGCCTTTATTATTTT CTGGGTG |
| 41BB CSR | SEQ ID NO: 11 | KRGRKKLLYIFKQPFMRPVQTTQEEDGCSCRFPEEEEG GCEL |
| CD28 CSR | SEQ ID NO: 12 | RSKRSRLLHSDYMNMTPRRPGPTRKHYQPYAPPRDFA AYRS |
|  | SEQ ID NO: 13 | AGGAGTAAGAGGAGCAGGCTCCTGCACAGTGACTAC ATGAACATGACTCCCCGCCGCCCCGGGCCCACCCGC AAGCATTACCAGCCCTATGCCCCACCACGCGACTTC GCAGCCTATCGCTCC |
| CD3ζ ISD | SEQ ID NO: 14 | RVKFSRSADAPAYQQGQNQLYNELNLGRREEYDVLDK RRGRDPEMGGKPRRKNPQEGLYNELQKDKMAEAYSEI GMKGERRRGKGHDGLYQGLSTATKDTYDALHMQALP PR |
|  | SEQ ID NO: 15 | AGAGTGAAGTTCAGCAGGAGCGCAGACGCCCCCGCG TACCAGCAGGGCCAGAACCAGCTCTATAACGAGCTC AATCTAGGACGAAGAGAGGAGTACGATGTTTTGGAC |

TABLE 1-continued

Exemplary sequences for the different CAR CS1 components

| Functional domains | SEQ ID # | Amino Acid Sequence/ Nucleic Acid Sequence |
|---|---|---|
| | | AAGAGACGTGGCCGGGACCCTGAGATGGGGGGAAA GCCGAGAAGGAAGAACCCTCAGGAAGGCCTGTACA ATGAACTGCAGAAAGATAAGATGGCGGAGGCCTACA GTGAGATTGGGATGAAAGGCGAGCGCCGGAGGGGC AAGGGGCACGATGGCCTTTACCAGGGTCTCAGTACA GCCACCAAGGACACCTACGACGCCCTTCACATGCAG GCCCTGCCCCCTCGCTAA |
| Linker | SEQ ID NO: 16 | GGGGSGGGGSGGGGS |
| Luc90 CS1 ScFv | SEQ ID NO: 17 | SQVQLQQPGAELVRPGASVKLSCKASGYSFTTYWMN WVKQRPGQGLEWIGMIHPSDSETRLNQKFKDKATLTV DKSSSTAYMQLSSPTSEDSAVYYCARSTMIATRAMDY WGQGTSVTVSGGGGSGGGGSGGGGSDIVMTQSQKSM STSVGDRVSITCKASQDVITGVAWYQQKPGQSPKLLIY SASYRYTGVPDRFTGSGSGTDFTFTISNVQAEDLAVYY CQQHYSTPLTFGAGTKLELK |
| | SEQ ID NO: 18 | TCCCAGGTCCAACTGCAGCAGCCTGGGGCTGAGCTG GTGAGGCCTGGAGCTTCAGTGAAGCTGTCCTGCAAG GCTTCGGGGTACTCCTTCACCACCTACTGGATGAACT GGGTGAAGCAGAGGCCTGGACAAGGCCTTGAGTGGA TTGGCATGATTCATCCTTCCGATAGTGAAACTAGGTT AAATCAGAAGTTCAAGGACAAGGCCACATTGACTGT AGACAAATCCTCCAGCACAGCCTACATGCAACTCAG CAGCCCCGACATCTGAGGACTCTGCGGTCTATTACTGT GCAAGATCTACTATGATTGCGACGAGGGCTATGGAC TACTGGGGTCAAGGAACCTCAGTCACCGTCTCCGGC GGTGGCGGTTCTGGTGGCGGTGGCTCCGGCGGTGGC GGTTCTGACATTGTGATGACCCAGTCTCAGAAATCCA TGTCCACATCAGTAGGAGACAGGGTCAGCATCACCT GCAAGGCCAGTCAGGATGTTATTACTGGTGTAGCCT GGTATCAACAGAAACCAGGGCAATCTCCTAAATTAC TGATTTACTCGGCATCCTACCGGTACACTGGAGTCCC TGATCGCTTCACTGGCAGTGGATCTGGGACGGATTTC ACTTTCACCATCAGCAATGTGCAGGCTGAAGACCTG GCAGTTTATTACTGTCAGCAACATTATAGTACTCCTC TCACTTTCGGTGCTGGGACCAAGCTGGAGCTGAAA |
| Luc90 Light chain variable region | SEQ ID NO: 19 | DIVMTQSQKSMSTSVGDRVSITCKASQDVITGVAWYQ QKPGQSPKLLIYSASYRYTGVPDRFTGSGSGTDFTFTIS NVQAEDLAVYYCQQHYSTPLTFGAGTKLELK |
| Luc63 heavy chain variable region | SEQ ID NO: 20 | EVKLLESGGGLVQPGGSLKLSCAASGFDFSRYWMSWV RQAPGKGLEWIGEINPDSSTINYTPSLKDKFIISRDNAKN TLYLQMSKVRSEDTALYYCARPDGNYWYFDVWGAGT TVTVSS |
| Luc63 light chain variable region | SEQ ID NO: 21 | DIVMTQSHKFMSTSVGDRVSITCKASQDVGIAVAWYQ QKPGQSPKLLIYWASTRHTGVPDRFTGSGSGTDFTLTIS NVQSEDLADYFCQQYSSYPYTFGGGTKLEIK |
| Luc34 heavy chain variable region | SEQ ID NO: 22 | QVQLQQSGAELARPGASVKLSCKASGYTFTSYWMQW VKQRPGQGLEWIGAIYPGDGDTRYTQKFKGKATLTAD KSSSTAYMQLSSLASEDSAVYYCARGKVYYGSNPFAY WGQGTLVTVSA |
| Luc34 light chain variable region | SEQ ID NO: 23 | DIQMTQSSSYLSVSLGGRVTITCKASDHINNWLAWYQQ KPGNAPRLLISGATSLETGVPSRFSGSGSGKDYTLSITSL QTEDVATYYCQQYWSTPWTFGGGTKLEIK |
| LucX1 heavy chain variable region | SEQ ID NO: 24 | QVQLQQSGPELVKPGASVKISCKASGYAFSS WMNWV KQRPGQGLEWIGRIYPGDGDTKYNGKFKGKATLTADK SSSTAYMQLSSLTSVDSAVYFCARSTMIATGAMDYWG QGTSVTVSS |
| LucX1 light chain variable region | SEQ ID NO: 25 | ETTVTQSPASLSMAIGEKVTIRCITSTDIDDDMNWYQQ KPGEPPKLLISEGNTLRPGVPSRFSSSGYGTDFVFTIENM LSEDVADYYCLQSDNLPLTFGGGTKLEIK |
| LucX2 heavy chain variable region | SEQ ID NO: 26 | QVQLQQSGPELVKPGASVKISCKASGYAFSSSWMNWV KQRPGQGLEWIGRIYPGDGDTKYNGKFKGKATLTADK SSSTAYMQLSSLTSVDSAVYFCARSTMIATGAMDYWG QGTSVTVS |

TABLE 1-continued

Exemplary sequences for the different CAR CS1 components

| Functional domains | SEQ ID # | Amino Acid Sequence/ Nucleic Acid Sequence |
|---|---|---|
| LucX2 light chain variable region | SEQ ID NO: 27 | DIVMTQSHKFMSTSVGDRVSITCKASQDVSTAVAWYQ QKPGQSPKLLIYSASYRYTGVPDRFTGSGSGTDFTFTISS VQAEDLAVYYCQQHYSTPPYTFGGGTKLEIK |

Therefore, in some embodiments, the disclosed CS1-specific CAR comprises the amino acid sequence SEQ ID NO:1 (shown below), or a variant thereof having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to SEQ ID NO:28.

CS1-CD28-CD3Z construct:

(SEQ ID NO: 28)
MGWSSIILFLVATATGVHSQVQLQQPGAELVRPGASVKLSCKASGYSFTT

YWMNWVKQRPGQGLEWIGMIHPSDSETRLNQKFKDKATLTVDKSSSTAYM

QLSSPTSEDSAVYYCARSTMIATRAMDYWGQGTSVTVSGGGGSGGGGSGG

GGSDIVMTQSQKSMSTSVGDRVSITCKASQDVITGVAWYQQKPGQSPKLL

IYSASYRYTGVPDRFTGSGSGTDFTFTISNVQAEDLAVYYCQQHYSTPLT

FGAGTKLELKLEPKSCDKTHTCPPCPDPKFWVLVVVGGVLACYSLLVTVA

FIIFWVRSKRSRLLHSDYMNMTPRRPGPTRKHYQPYAPPRDFAAYRSRVK

FSRSADAPAYQQGQNQLYNELNLGRREEYDVLDKRRGRDPEMGGKPRRKN

PQEGLYNELQKDKMAEAYSEIGMKGERRRGKGHDGLYQGLSTATKDTYDA

LHMQALPPR.

Nucleic Acids and Vectors

Also disclosed are polynucleotides and polynucleotide vectors encoding the disclosed CS1-specific CARs that allow expression of the CS1-specific CARs in the disclosed immune effector cells.

For example, in some embodiments, the disclosed CS1-specific CAR are encoded by the nucleic acid sequence SEQ ID NO:28 (shown below), or a variant thereof having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to SEQ ID NO:29.

PCDH-CS1-scFv-myc tag-CD28-CD3zeta (PCDH-CS1-CAR) construct:

(SEQ ID NO: 29)
ATGGGATGGAGCTCTATCATCCTCTTCTTGGTAGCAACAGCTACAGGTG

TCCACTCCCAGGTCCAACTGCAGCAGCCTGGGGCTGAGCTGGTGAGGCC

TGGAGCTTCAGTGAAGCTGTCCTGCAAGGCTTCGGGGTACTCCTTCACC

ACCTACTGGATGAACTGGGTGAAGCAGAGGCCTGGACAAGGCCTTGAGT

GGATTGGCATGATTCATCCTTCCGATAGTGAAACTAGGTTAAATCAGAA

GTTCAAGGACAAGGCCACATTGACTGTAGACAAATCCTCCAGCACAGCC

TACATGCAACTCAGCAGCCCGACATCTGAGGACTCTGCGGTCTATTACT

GTGCAAGATCTACTATGATTGCGACGAGGGCTATGGACTACTGGGGTCA

AGGAACCTCAGTCACCGTCTCCGGCGGTGGCGGTTCTGGTGGCGGTGGC

TCCGGCGGTGGCGGTTCTGACATTGTGATGACCCAGTCTCAGAAATCCA

TGTCCACATCAGTAGGAGACAGGGTCAGCATCACCTGCAAGGCCAGTCA

GGATGTTATTACTGGTGTAGCCTGGTATCAACAGAAACCAGGGCAATCT

CCTAAATTACTGATTTACTCGGCATCCTACCGGTACACTGGAGTCCCTG

ATCGCTTCACTGGCAGTGGATCTGGGACGGATTTCACTTTCACCATCAG

CAATGTGCAGGCTGAAGACCTGGCAGTTTATTACTGTCAGCAACATTAT

AGTACTCCTCTCACTTTCGGTGCTGGGACCAAGCTGGAGCTGAAACTCG

AGCCCAAATCTTGTGACAAAACTCACACATGCCCACCGTGCCCGGATCC

CAAATTTTGGGTGCTGGTGGTGGTTGGTGGAGTCCTGGCTTGCTATAGC

TTGCTAGTAACAGTGGCCTTTATTATTTTCTGGGTGAGGAGTAAGAGGA

GCAGGCTCCTGCACAGTGACTACATGAACATGACTCCCCGCCGCCCGG

GCCCACCCGCAAGCATTACCAGCCCTATGCCCCACCACGCGACTTCGCA

GCCTATCGCTCCAGAGTGAAGTTCAGCAGGAGCGCAGACGCCCCCGCGT

ACCAGCAGGGCCAGAACCAGCTCTATAACGAGCTCAATCTAGGACGAAG

AGAGGAGTACGATGTTTTGGACAAGAGACGTGGCCGGGACCCTGAGATG

GGGGGAAAGCCGAGAAGGAAGAACCCTCAGGAAGGCCTGTACAATGAAC

TGCAGAAAGATAAGATGGCGGAGGCCTACAGTGAGATTGGGATGAAAGG

CGAGCGCCGGAGGGGCAAGGGGCACGATGGCCTTTACCAGGGTCTCAGT

ACAGCCACCAAGGACACCTACGACGCCCTTCACATGCAGGCCCTGCCCC

CTCGCTAA.

Nucleic acid sequences encoding the disclosed CARs, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding CARs is typically achieved by operably linking a nucleic acid encoding the CAR polypeptide to a promoter, and incorporating the construct into an expression vector. Typical cloning vectors contain transcription and translation terminators, initiation sequences, and promoters useful for regulation of the expression of the desired nucleic acid sequence.

The disclosed nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. In some embodiments, the polynucleotide vectors are lentiviral or retroviral vectors.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, MND (myeloproliferative sarcoma virus) promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoter can alternatively be an inducible promoter. Examples of inducible promoters include, but are not limited to a metallothionine promoter, a glucocorticoid promoter, a progesterone promoter, and a tetracycline promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian, e.g., human cells.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc, (Birmingham, Ala.).

Immune Effector Cells

Also disclosed are immune effector cells that are engineered to express the disclosed CARs. These cells are preferably obtained from the subject to be treated (i.e. are autologous). However, in some embodiments, immune effector cell lines or donor effector cells (allogeneic) are used. Immune effector cells can be obtained from a number of sources, including peripheral blood mononuclear cells, bone marrow, lymph node tissue, cord blood, thymus tissue, tissue from a site of infection, ascites, pleural effusion, spleen tissue, and tumors. Immune effector cells can be obtained from blood collected from a subject using any number of techniques known to the skilled artisan, such as Ficoll™ separation. For example, cells from the circulating blood of an individual may be obtained by apheresis. In some embodiments, immune effector cells are isolated from peripheral blood lymphocytes by lysing the red blood cells and depleting the monocytes, for example, by centrifugation through a PERCOLL™ gradient or by counterflow centrifugal elutriation. A specific subpopulation of immune effector cells can be further isolated by positive or negative selection techniques. For example, immune effector cells can be isolated using a combination of antibodies directed to surface markers unique to the positively selected cells, e.g., by incubation with antibody-conjugated beads for a time period sufficient for positive selection of the desired immune effector cells. Alternatively, enrichment of immune effector cells population can be accomplished by negative selection using a combination of antibodies directed to surface markers unique to the negatively selected cells.

In some embodiments, the immune effector cells comprise any leukocyte involved in defending the body against infectious disease and foreign materials. For example, the immune effector cells can comprise lymphocytes, monocytes, macrophages, dentritic cells, mast cells, neutrophils, basophils, eosinophils, or any combinations thereof. For example, the immune effector cells can comprise T lymphocytes.

T cells or T lymphocytes can be distinguished from other lymphocytes, such as B cells and natural killer cells (NK cells), by the presence of a T-cell receptor (TCR) on the cell surface. They are called T cells because they mature in the thymus (although some also mature in the tonsils). There are several subsets of T cells, each with a distinct function.

T helper cells ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, $T_H9$, or $T_{FH}$, which secrete different cytokines to facilitate a different type of immune response.

Cytotoxic T cells ($T_C$ cells, or CTLs) destroy virally infected cells and tumor cells, and are also implicated in transplant rejection. These cells are also known as CD8+ T cells since they express the CD8 glycoprotein at their surface. These cells recognize their targets by binding to antigen associated with MHC class I molecules, which are present on the surface of all nucleated cells. Through IL-10, adenosine and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory cells may be either CD4+ or CD8+. Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of CD4+ $T_{reg}$ cells have been described—naturally occurring $T_{reg}$ cells and adaptive $T_{reg}$ cells.

Natural killer T (NKT) cells (not to be confused with natural killer (NK) cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d.

In some embodiments, the T cells comprise a mixture of CD4+ cells. In other embodiments, the T cells are enriched for one or more subsets based on cell surface expression. For example, in some cases, the T comprise are cytotoxic CD8+ T lymphocytes. In some embodiments, the T cells comprise γδ T cells, which possess a distinct T-cell receptor (TCR) having one γ chain and one δ chain instead of α and β chains.

Natural-killer (NK) cells are CD56+CD3− large granular lymphocytes that can kill virally infected and transformed cells, and constitute a critical cellular subset of the innate immune system (Godfrey J, et al. Leuk Lymphoma 2012 53:1666-1676). Unlike cytotoxic CD8+ T lymphocytes, NK cells launch cytotoxicity against tumor cells without the requirement for prior sensitization, and can also eradicate MHC-I-negative cells (Narni-Mancinelli E, et al. Int Immunol 2011 23:427-431). NK cells are safer effector cells, as they may avoid the potentially lethal complications of cytokine storms (Morgan R A, et al. Mol Ther 2010 18:843-851), tumor lysis syndrome (Porter D L, et al. N Engl J Med 2011 365:725-733), and on-target, off-tumor effects. Although NK cells have a well-known role as killers of cancer cells, and NK cell impairment has been extensively documented as crucial for progression of MM (Godfrey J, et al. Leuk Lymphoma 2012 53:1666-1676; Fauriat C, et al. Leukemia 2006 20:732-733), the means by which one might enhance NK cell-mediated anti-MM activity has been largely unexplored prior to the disclosed CARs.

Therapeutic Methods

Immune effector cells expressing the disclosed CARs can elicit an anti-tumor immune response against MM cells. The anti-tumor immune response elicited by the disclosed CAR-modified immune effector cells may be an active or a passive immune response. In addition, the CAR-mediated immune response may be part of an adoptive immunotherapy approach in which CAR-modified immune effector cells induce an immune response specific to CS1.

Adoptive transfer of immune effector cells expressing chimeric antigen receptors is a promising anti-cancer therapeutic. Following the collection of a patient's immune effector cells, the cells may be genetically engineered to express the disclosed CS1-specific CARs, then infused back into the patient.

The disclosed CAR-modified immune effector cells may be administered either alone, or as a pharmaceutical composition in combination with diluents and/or with other components such as IL-2, IL-15, or other cytokines or cell populations. Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions for use in the disclosed methods are in some embodiments formulated for intravenous administration. Pharmaceutical compositions may be administered in any manner appropriate treat MM. The quantity and frequency of administration will be determined by such factors as the condition of the patient, and the severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, such as $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently re-draw blood (or have an apheresis performed), activate T cells therefrom according to the disclosed methods, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Using this multiple blood draw/multiple reinfusion protocol may serve to select out certain populations of T cells.

The administration of the disclosed compositions may be carried out in any convenient manner, including by injection, transfusion, or implantation. The compositions described herein may be administered to a patient subcutaneously, intradermally, intratumorally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a tumor, lymph node, or site of infection.

In certain embodiments, the disclosed CAR-modified immune effector cells are administered to a patient in conjunction with (e.g., before, simultaneously or following) any number of relevant treatment modalities, including but not limited to thalidomide, dexamethasone, bortezomib, and lenalidomide. In further embodiments, the CAR-modified immune effector cells may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-modified immune effector cells are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

Definitions

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "protein domain" refers to a portion of a protein, portions of a protein, or an entire protein showing structural integrity; this determination may be based on amino acid composition of a portion of a protein, portions of a protein, or the entire protein.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

A number of embodiments of the invention have been described. Nevertheless, it will be understood that various modifications may be made without departing from the spirit and scope of the invention. Accordingly, other embodiments are within the scope of the following claims.

EXAMPLES

Example 1

Genetic Modification of T Cells Redirected Towards CS1 Enhances Eradication of Myeloma Cells In the present study, T cells were manipulated to express a CS1-specific CAR incorporating CD28-CD3ζ signaling moieties, demonstrating that CS1-specific CAR T cells mediated enhanced cytokine release and cytotoxicity in response to CS1-expressing myeloma cells, which occurred in a CS1-dependent manner. Moreover, in orthotopic MM xenograft mouse models, CS1-redirected T cells efficiently eradicated human myeloma cells and significantly prolonged mouse survival. Together, these data suggest that adoptive therapy with T cells armed with a CS1-specific CAR represents a promising strategy against relapsed MM.

Materials and Methods

Cell Culture

Human multiple myeloma cell lines IM9, NCI-H929, MM.1S and RPMI-8226 were obtained from the American Type Culture Collection (ATCC), and maintained in RPMI 1640 medium (Invitrogen) supplemented with 10% fetal bovine serum (FBS) (Invitrogen). 293T and phoenix packaging cells were cultivated in DMEM medium (Invitrogen) with 10% FBS. Human peripheral blood mononuclear cells (PBMCs) from healthy donors and multiple myeloma patients were isolated by Ficoll-Paque Plus (GE Healthcare Bio-Sciences, Pittsburgh, Pa.) density gradient centrifugation, and monocytes were depleted by plastic adherence. Primary $CD138^+$ myeloma cells were positively selected from bone marrow aspirates of patients using human anti-CD138 MicroBeads and magnet-assisted cell sorting (MACS, Miltenyi Biotech), according to the manufacturer's instructions. Informed consent was obtained from myeloma patients according to a protocol approved by The Ohio State University Institutional Review Board.

Mice

Six- to 8-week-old male NOD-scid IL-2Rgamma null (NSG) mice were obtained from The Jackson Laboratory. Mice were monitored frequently for MM disease progression, and sacrificed when they became moribund with the symptoms of hind limb paralysis, lethargy, or obvious weight loss. All animal work was approved by The Ohio State University Animal Care and Use Committee.

Generation of the CS1-Specific CAR Retroviral Construct

The anti-CS1 scFv was derived from the hybridoma cell line Luc90. The coding domain sequences for variable regions of heavy ($V_H$) and light ($V_L$) chains were amplified separately and recombined using a linker by overlapping PCR reaction. The $V_H$-linker-$V_L$ fragment was incorporated in frame with the CD28-CD3ζ portion. The entire anti-CS1-scFv-CD28-CD3ζ fragment was then ligated into a retroviral vector designated Pinco (Yu J, et al. Immunity 2006 24:575-90; Becknell B, et al. J Immunol Methods 2005 296:115-23) to generate a Pinco-CS1-CAR construct.

Retroviral Transduction of T Lymphocytes

Retroviral supernatants were collected from phoenix packaging cells transiently transfected with the Pinco- or Pinco-CS1-CAR construct for 48 h, as described previously (Becknell B, et al. J Immunol Methods. 2005 296(1-2):115-123; Yu J, et al. Immunity. 2006 24(5):575-590). PBMCs were cultured in RPMI 1640 medium with 10% FBS and stimulated with Human T-Activator CD3/CD28 Dynabeads (Invitrogen) and 150 IU/mL human recombinant interleukin-2 (IL-2, Hoffman-La Roche Inc.) for 2 days. Then cells were resuspended in infectious supernatants and applied into RETRONECTIN (Clontech Laboratories)-coated non-tissue culture-treated 6-well plates according to the manufacturer's protocol. The infection process was repeated once on the second day. Then cells were transferred into tissue-culture-treated flasks and maintained in the presence of 150 IU/mL IL-2. Transduced T cells were purified using a FACSARIA II cell sorter (BD Biosciences) based on expression of a GFP marker on the cell surface encoded by the Pinco vector.

Flow Cytometry Analysis

For detection of CS1-CAR expression on the cell surface, transduced T cells were washed with PBS containing 4% bovine serum albumin, and incubated with biotin-labeled goat anti-mouse (Fab)2 polyclonal antibody or normal polyclonal goat immunoglobulin G (IgG) antibody (Jackson ImmunoResearch) as an isotype control. Then cells were stained with allophycocyanin (APC)-conjugated streptavidin (Jackson ImmunoResearch) and anti-CD3 antibody conjugated to V450 (BD Biosciences). To determine the expression of CS1 on the surface of myeloma cells, the cells were stained with phycoerythrin (PE)-conjugated mouse anti-CS1 mAb (eBiosciences) and APC-conjugated mouse anti-CD138 mAb (Miltenyi Biotec). Antibody staining was monitored with a BD LSRII flow cytometer. Data analysis was carried out using FLOWJO software (Tree Star Inc.)

Immunoblotting

Cells were lysed in laemmli buffer. Lysates were separated by SDS-PAGE gel and transferred to nitrocellulose membrane (Millipore). The membrane was probed with mouse anti-human CD3ζ mAb (BD Pharmingen) and then with a horseradish peroxidase-conjugated goat anti-mouse IgG antibody. Antibody binding was revealed by using an enhanced chemiluminescence reagent (GE Healthcare Biosciences).

Generation of RPMI-8226 Cells Stably Expressing CS1

Full length human CS1 coding sequence was PCR-amplified from the IM9 cDNA, and inserted into a lentiviral vector designated PCDH-CMV-MCS-EF1-copGFP (PCDH, System Biosciences), yielding PCDH-CS1. To produce lentivirus, 293T cells were co-transfected with the PCDH-CS1 plasmid or a PCDH empty vector plasmid plus the packaging plasmids pCMV-VSVG and pCMV-dr9 using calcium phosphate transfection reagent (Promega). Then, the lentiviral supernatants were harvested and used to infect RPMI-8226 cells using a previously published protocol (Becknell B, et al. J Immunol Methods. 2005 296(1-2):115-123; Yu J, et al. Immunity. 2006 24(5):575-590).

Cytotoxicity Assay

A standard 4-hour $^{51}$Cr release assay was performed as described previously (Yu J, et al. Blood 2010 115:274-81). Briefly, target cells were labeled with $^{51}$Cr and co-cultured with T cells at various effector/target ratios (E/T) in the wells of 96-well V-bottom plate at 37° C. for 4 hours. Supernatants were harvested and transferred into scintillation vials containing a liquid scintillation cocktail (Fisher Scientific), and the release of $^{51}$Cr was measured on TOPCOUNT counter (Canberra Packard). Target cells incubated in complete medium or 1% SDS were used to determine spontaneous or maximal $^{51}$Cr release. The percentage of specific lysis was calculated using the standard formula: 100×(cpm experimental release−cpm spontaneous release)/(cpm maximal release−cpm spontaneous release).

Cytokine Release Assays

Target cells were co-cultured with an equal number of effector cells in 96-well V-bottom plates at 37° C. for 24 hours. Cell-free supernatants were harvested and assessed for IFN-g and interleukin (IL)-2 secretion by ELISA using corresponding ELISA kits from R&D system according to the manufacturer's protocol.

CD107a Degranulation Assay

CD107a assay was performed as described previously with some modification (He S, et al. Blood 2013 121:4663-71). Briefly, MM target cells (2.5×10$^5$) were co-cultured with an equal number of effector cells in 0.2 mL per well in 96-well V-bottom plates. Control cells are either mock- or CS1-CAR-transduced T cells incubated without target cells. Anti-CD107a or IgG1 isotype antibody conjugated to APC (BD Biosciences) together with 1 mL monensin (BD Biosciences) was added and incubated at 37° C. for 4 hours. Cells were further stained with PE-conjugated CD69 and V450-conjugated CD3 antibodies, and analyzed using a LSRII flow cytometer (BD Biosciences).

Intracellular Staining of Granzyme B and Perforin

Mock- or CS1-CAR-transduced T cells were washed and stained with V450-conjugated anti-human CD3 mAb. Subsequently, cells were fixed and permeabilized using the Cytofix/Cytoperm Kit (BD Biosciences), labeled with APC-conjugated anti-granzyme B (Invitrogen), APC-conjugated anti-perforin antibody (eBiosciences) or a mouse APC-conjugated isotype antibody, and then analyzed on a BD LSRII flow cytometer (BD Biosciences).

In Vivo Treatment of MM-Bearing Mice and Bioluminescence Imaging

MM.1S and IM9 myeloma cells were retrovirally transduced with Pinco-pGL3-luc/GFP virus expressing firefly luciferase, and GFP-positive cells were sorted using the aforementioned method, yielding MM.1S-GL3 and IM9-GL3 cells, respectively. Male NSG mice were intravenously injected with 8×10$^6$ MM.1S-GL3 cells or 5×10$^5$ IM9-GL3 cells in 400 μL of PBS via tail vein on day 0 to establish a xenograft orthotopic MM model. On days 7 and 14 (MM.1S) or 21 (IM-9), the mice were intravenously administered with 10×10$^6$ effector cells, CS1-CAR-transduced T cells or mock-transduced control cells, in 400 mL of PBS via tail vein. Five weeks after inoculation with MM cells, the mice were intraperitoneally infused with D-luciferin (150 mg/kg body weight; Gold Biotechnology), anesthetized with isoflurane, and imaged using the In Vivo Imaging System (IVIS) with Living Image software (PerkinElmer).

Statistical Analysis

The unpaired Student t test was used to compare two independent groups for continuous endpoints if normally distributed. One-way ANOVA was used when three or more independent groups were compared. For survival data, Kaplan-Meier curves were plotted and compared using a log-rank test. All tests were two-sided. P values were adjusted for multiple comparisons using the Bonferroni method. A P value of less than 0.05 is considered statistically significant.

Results

Generation of Primary T Cells Expressing CS1-Specific CAR

Figure 1B:
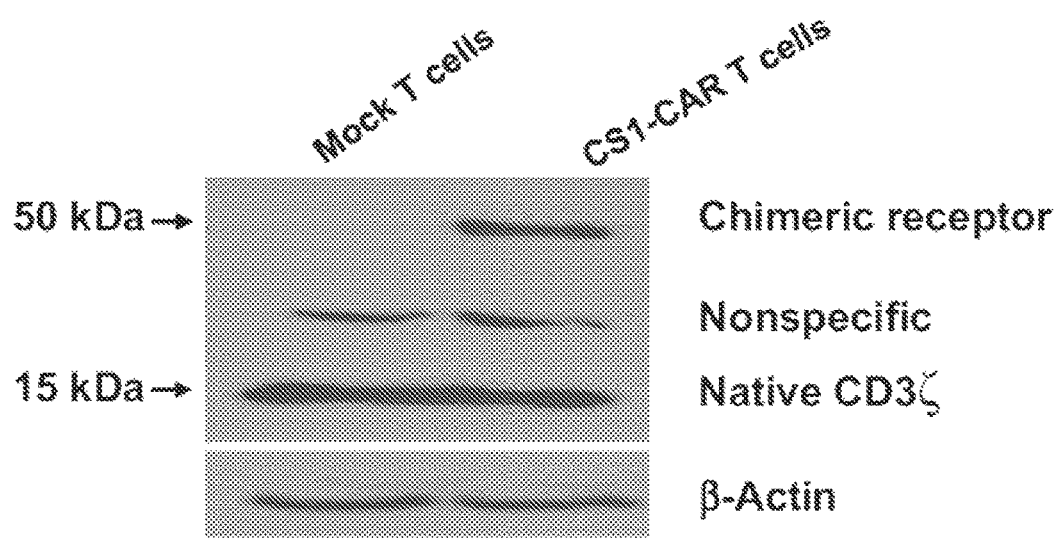
Figure 1C:
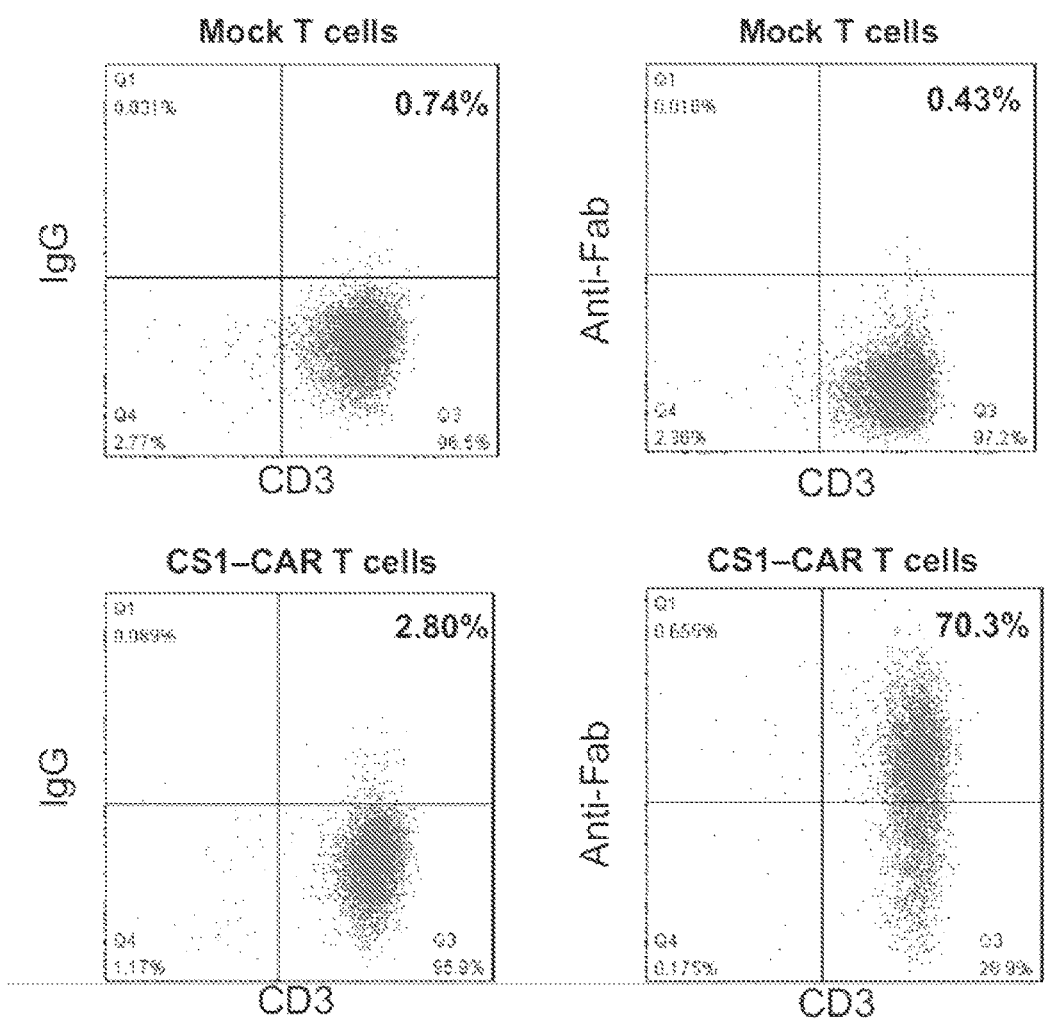

A Pinco retroviral vector encoding a CS1-specific CAR (Pinco-CS1-CAR) was constructed, which consisted of anti-CS1 scFv, the hinge and transmembrane regions of the CD8 molecule, the CD28 costimulatory signaling moiety, and the cytoplasmic component of CD3ζ molecule (FIG. 1A). Anti-CD3/CD28 antibody-activated primary T cells from a healthy donor were transduced with retroviral particles encoding CS1-CAR or empty vector (mock) and sorted for expression of GFP, which was encoded by the retroviral construct. To determine whether CS1-CAR was successfully transferred, the sorted cells were lysed and subjected to immunoblotting with an anti-CD3ζ mAb. As shown in FIG. 1B, in contrast with the mock-transduced T cells, which only expressed endogenous CD3ζ protein, CS1-CAR-transduced T cells expressed the chimeric CS1-scFv-CD28-CD3ζ fusion protein at the predicted size in addition to native CD3ζ. Expression of CS1-CAR on the cell surface was demonstrated by staining transduced T cells with a goat anti-mouse Fab antibody that recognized the scFv portion of anti-CS1, which detected expression of the scFV on 70.3% of CS1-CAR-transduced T cells, whereas expression remained almost undetectable on mock-transduced T cells (FIG. 1C).

Recognition of CS1+ Myeloma Cell Lines by CS1-Specific CAR T Cells

Figure 2A:
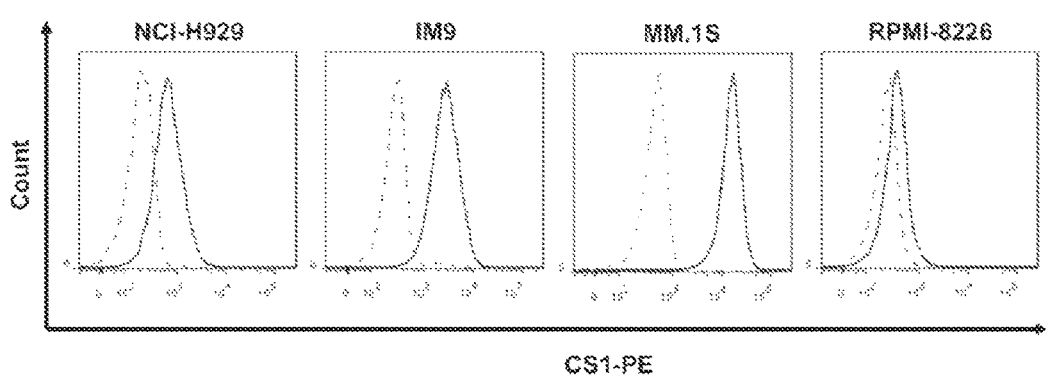
FIGS. 2A to 2C show CS1-redirected T cells secrete more IFN-γ and IL-2 than mock T cells in response to CS1-expressing myeloma cell lines.
Figure 2B:
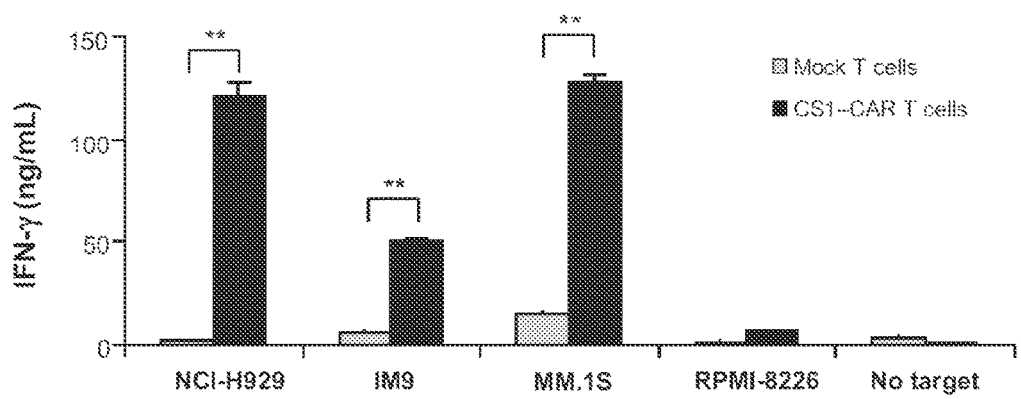
Figure 2C:
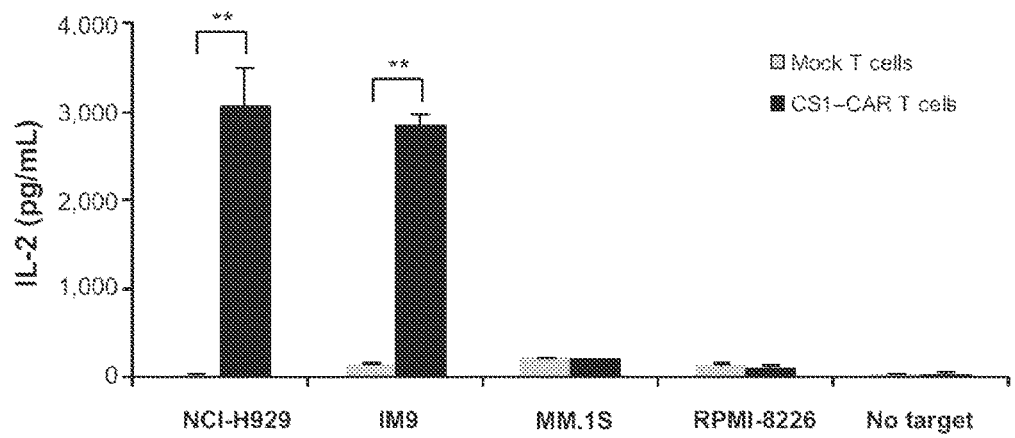
Figure 7A:
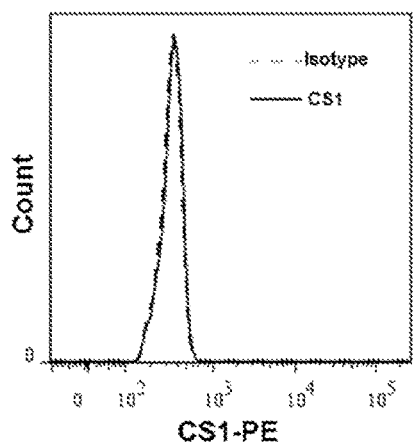
FIGS. 7A to 7E show 293T transformed cells expressing CS1 were susceptible to recognition and lysis by CS1-CAR T cells.
Figure 8A:
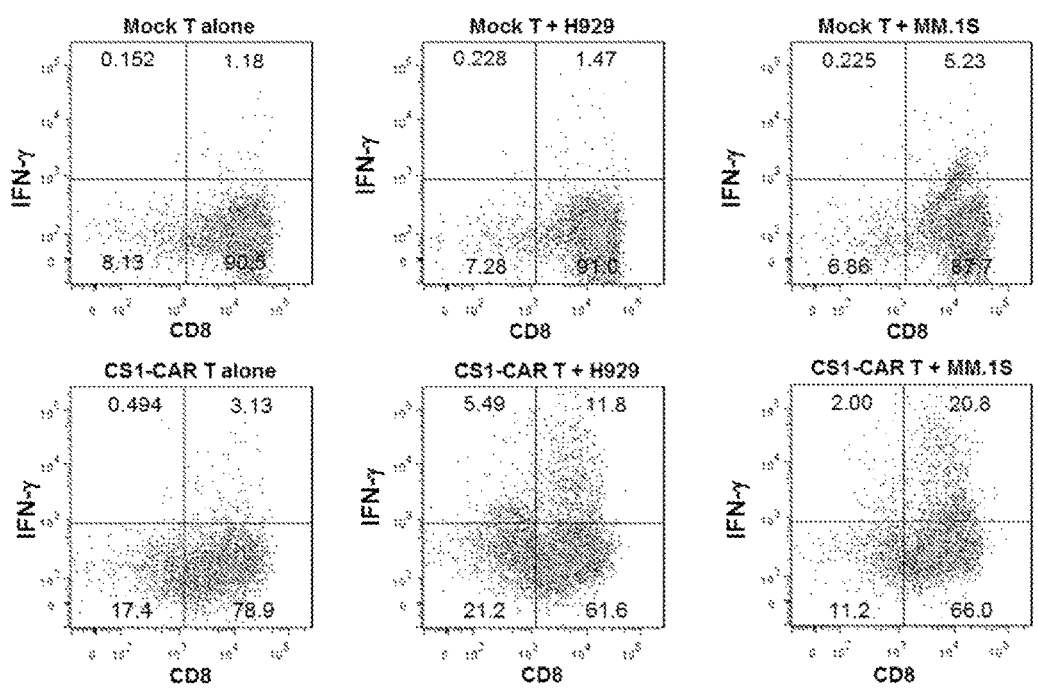
FIGS. 8A and 8B show that both CD4$^+$ and CD8$^+$ CS1-CART cells were activated in response to myeloma cells.

Surface expression of CS1 was evaluated in four commonly used myeloma cell lines NCI-H929, IM9, MM.1S, and RPMI-8226 by flow cytometry, which revealed that CS1 protein was variably expressed in these cell lines with much higher expression in NCI-H929, IM9, and MM.1S cells than RPMI-8226 cells with minimal CS1 expression (FIG. 2A). As a negative control, the transformed human kidney cell line, 293T, did not express CS1 on its surface (FIG. 7A). To determine the capacity of CS1-CART cells for recognition of myeloma cells that endogenously expressed CS1, IFN-γ, and IL-2 secretion was measured via ELISA in supernatants from mock-transduced T cells or CS1-CAR-transduced T cells in the presence or absence of each myeloma cell line. Mock-transduced T cells and CS1-CAR-transduced T cells each alone produced negligible levels of IFN-γ and IL-2 (FIGS. 2B and C); however, after exposure to NCI-H929 and IM9 cells expressing high levels of CS1, significantly greater amounts of IFN-γ and IL-2 proteins were secreted by CS1-CAR T cells but not by mock T cells. In response to MM.1S cells with high levels of CS1 expression, CS1-CAR-transduced T cells also produced a higher amount of IFN-γ than mock-transduced T cells (FIG. 2B) whereas, for unknown reasons, CS1-CAR-transduced T cells could not be triggered by this cell line to secrete higher levels of IL-2 than mock-transduced T cells (FIG. 2C). In addition, compared with corresponding mock-transduced subsets of T cells, both CD4+ (CD8) and CD8+ CS1-CAR T cells displayed increased IFN-g secretion in response to NCI-H929 or MM.1S cells (FIG. 8A). For RPMI-8226 cells with very low levels of CS1 expression, both mock-transduced T cells and CS1-CAR-transduced T cells produced low levels of IFN-g and IL-2 that were comparable with background (FIGS. 2B and C). These findings suggest that, compared with mock-transduced T cells, CS1-CAR-transduced T cells can more specifically recognize MM cells with high levels of endogenous CS1 expression, and become more activated after the recognition of these MM cells.

In Vitro Cytolytic Potency Against Myeloma Cells Triggered by CS1-Specific CAR

Figure 3A:
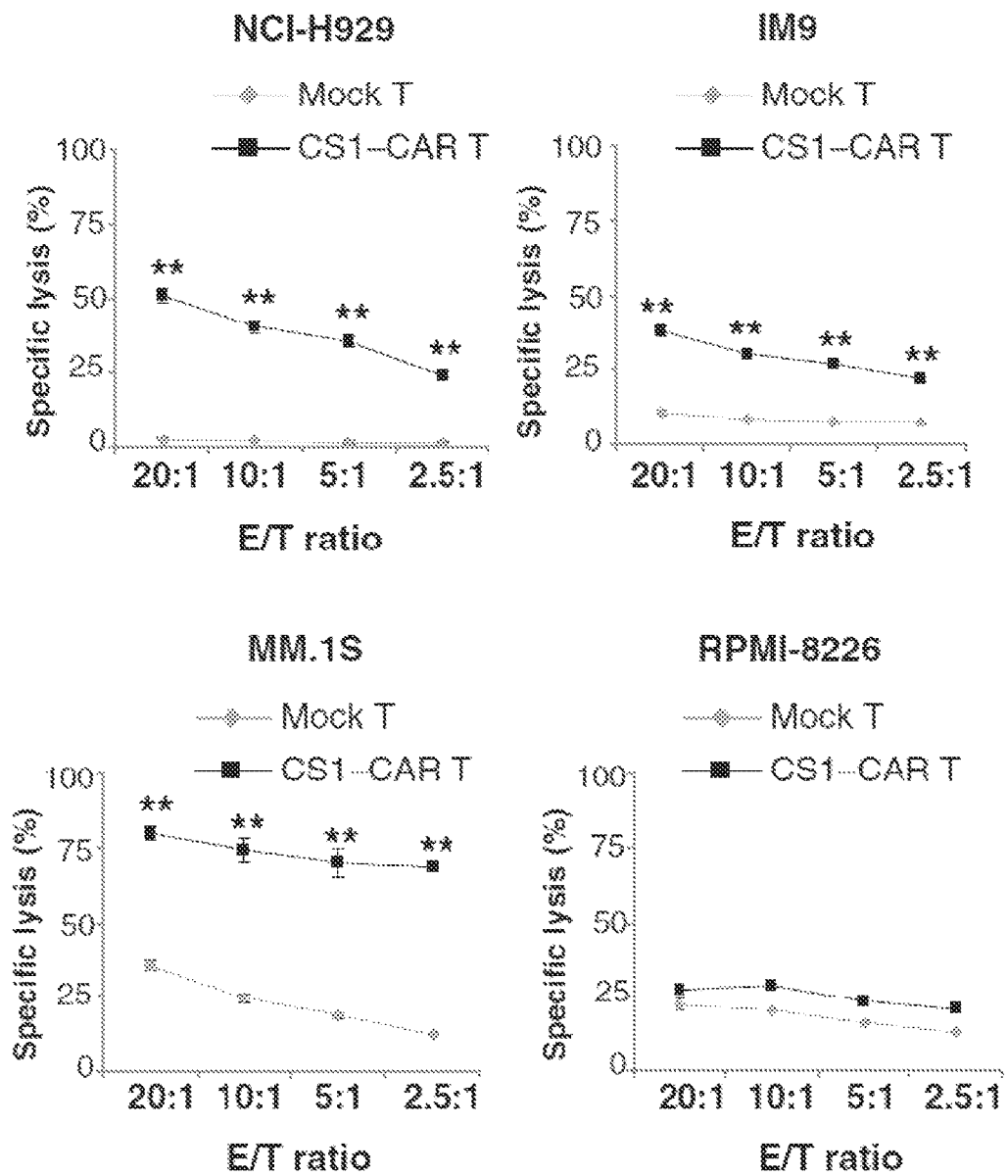

To determine whether enhanced recognition of CS1+ myeloma cells by CS1-CAR T cells could lead to more efficient tumor cell lysis, a standard 4-hour chromium-51 release assay was performed. NCI-H929, IM9, and MM.1S cells, which express high levels of CS1, were resistant to mock-transduced T-cell-mediated killing, even at E/T ratios as high as 20:1; however, these cells were efficiently lysed by CS1-CART cells at all E:T ratios tested (FIG. 3A, left three). However, compared with mock-transduced T cells, the cytolytic activity of RPMI-8226 cells expressing low levels of CS1 could only be slightly augmented upon co-incubation with CS1-CAR-transduced T cells (FIG. 3A, right one). Degranulation and activation of T cells was further characterized by assessing expression of CD107a and CD69 in mock-transduced T cells and CS1-CAR-transduced T cells following incubation with or without NCI-H929 myeloma cells which, as mentioned above, triggered a strong response in CS1-CAR T cells with respect to cytokine release and cytolytic activity. Consistent with the aforementioned data about cytokine release and cytolytic activity, degranulation and activation occurred to a greater extent in CS1-CAR T cells than in mock T cells in response to NCI-H929 cells, as evidenced by upregulation of surface coexpression of mobilized CD107a and the activation marker, CD69 (FIG. 3B).

Figure 8B:
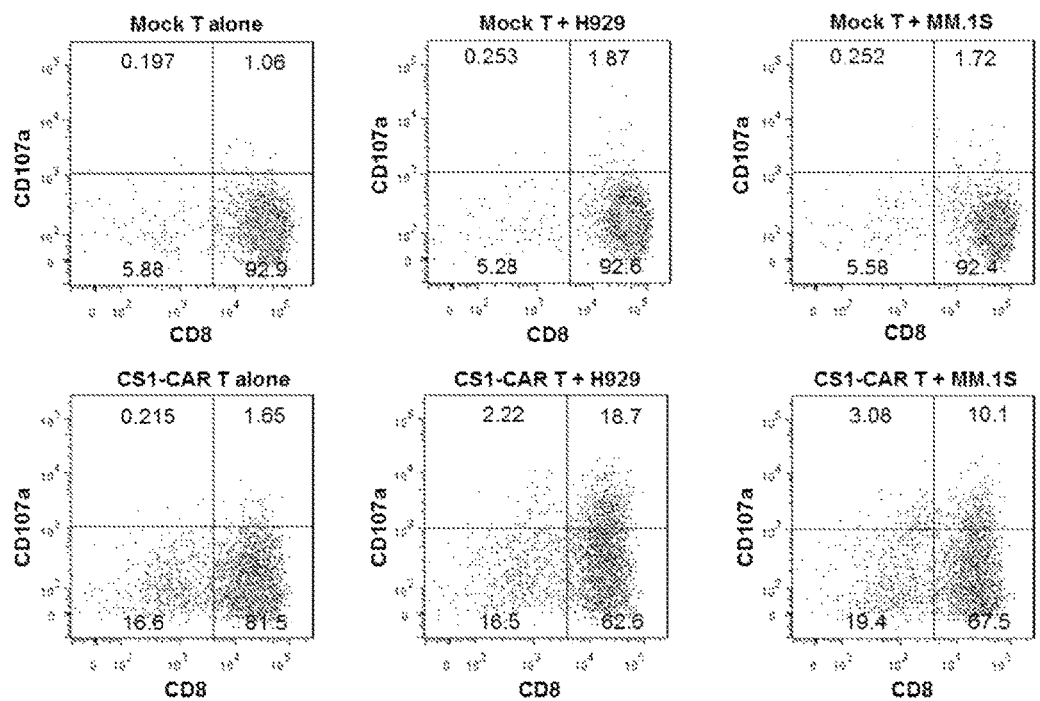

Moreover, compared with corresponding mock-transduced subsets of T cells, both CD4+ (CD8) and CD8+ CS1-CAR T cells exhibited increased levels of degranulation when stimulated by NCI-H929 or MM.1S cells (FIG. 8B). In addition, using an intracellular staining approach, compared with mock-transduced T cells, CS1-CAR-transduced T cells expressed significantly higher levels of granzyme B, but not perforin, even in the absence of target cells (FIGS. 3C and D), suggesting that granzyme B may be predominantly involved in mediating the cytolytic activity of CS1-redirected T cells. This finding is in line with a previous report showing T cells grafted with a carcinoembryonic antigen-specific CAR incorporating a combined CD28-CD3ζ signaling moiety harbored elevated levels of granzyme B compared with unmodified T cells (Koehler H, et al. Cancer Res 2007 67:2265-73).

Figure 4A:
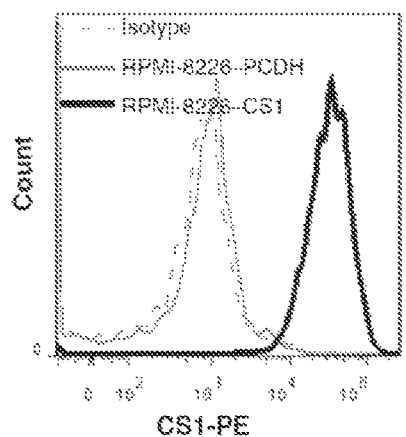
FIGS. 4A to 4D show ectopic overexpression of CS1 in MM cells triggers enhanced cytotoxicity and cytokine secretion after recognition by CS1-CAR T cells.
Figure 4B:
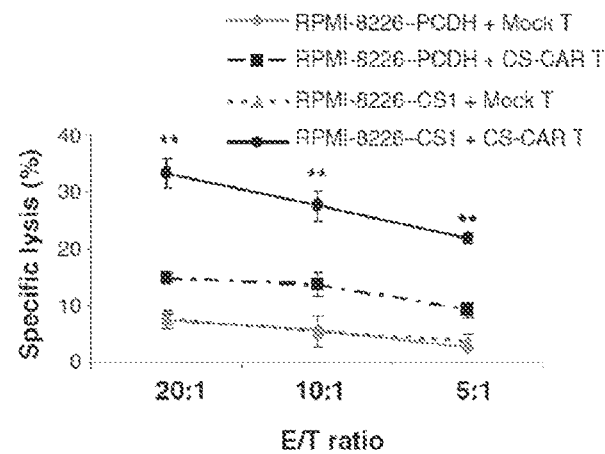
Figure 4C:
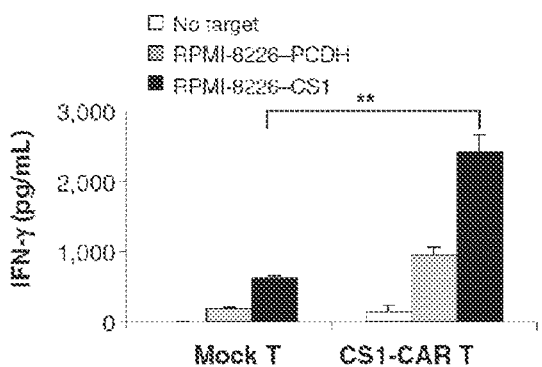
Figure 4D:
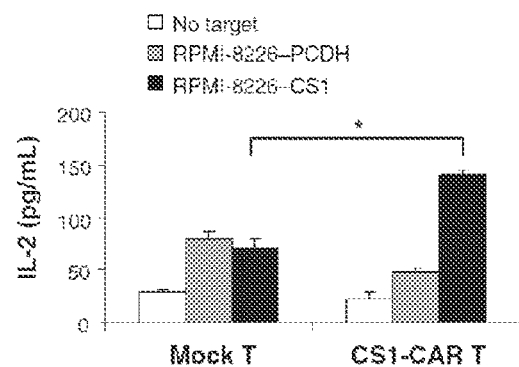
Figure 7B:
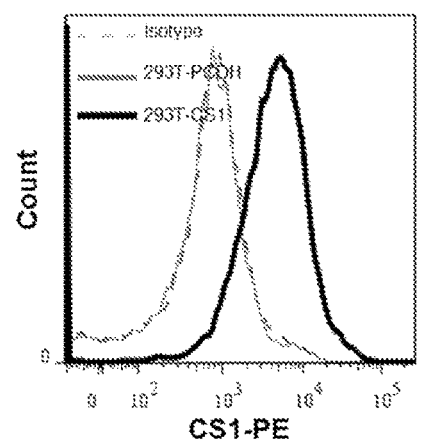
Figure 7C:
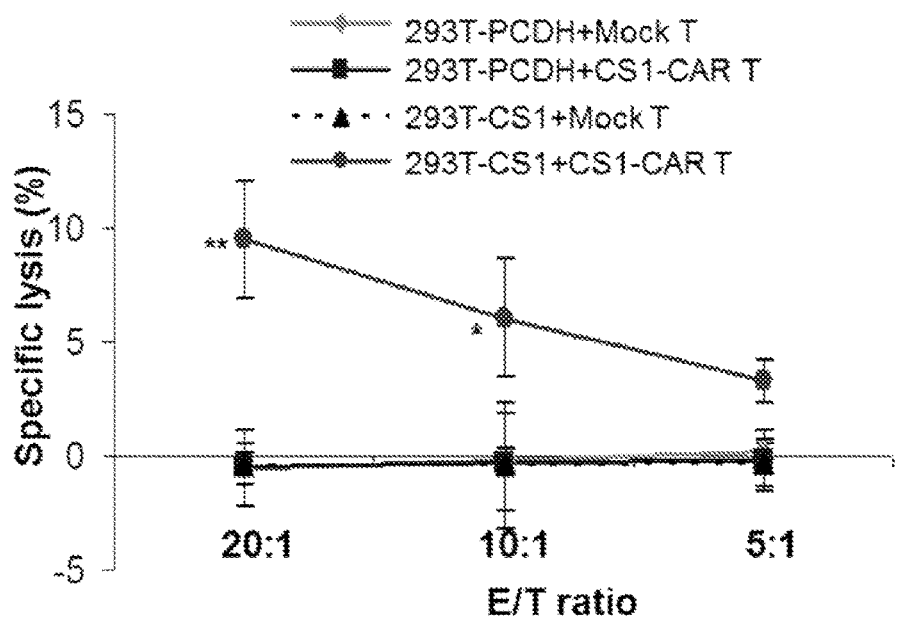
Figure 7D:
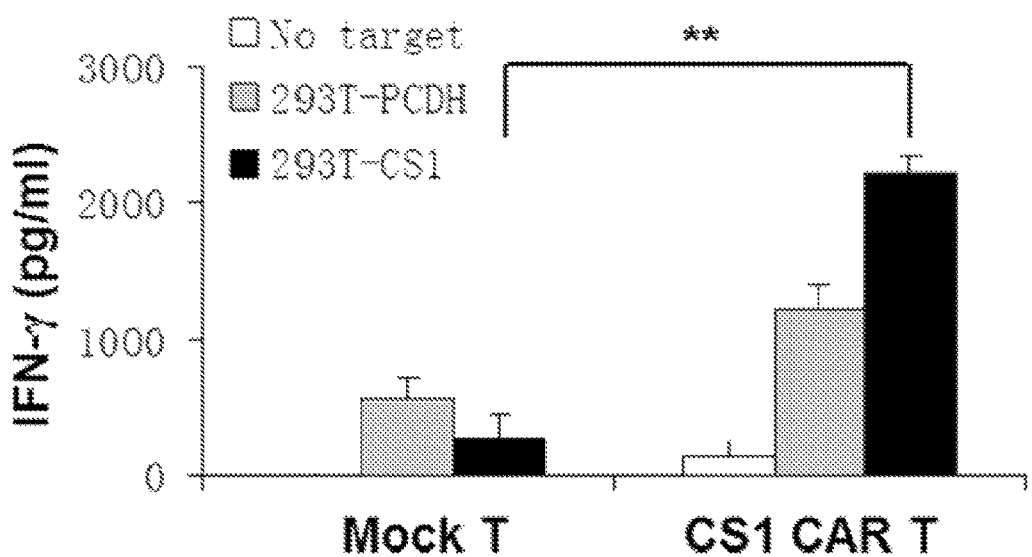
Figure 7E:
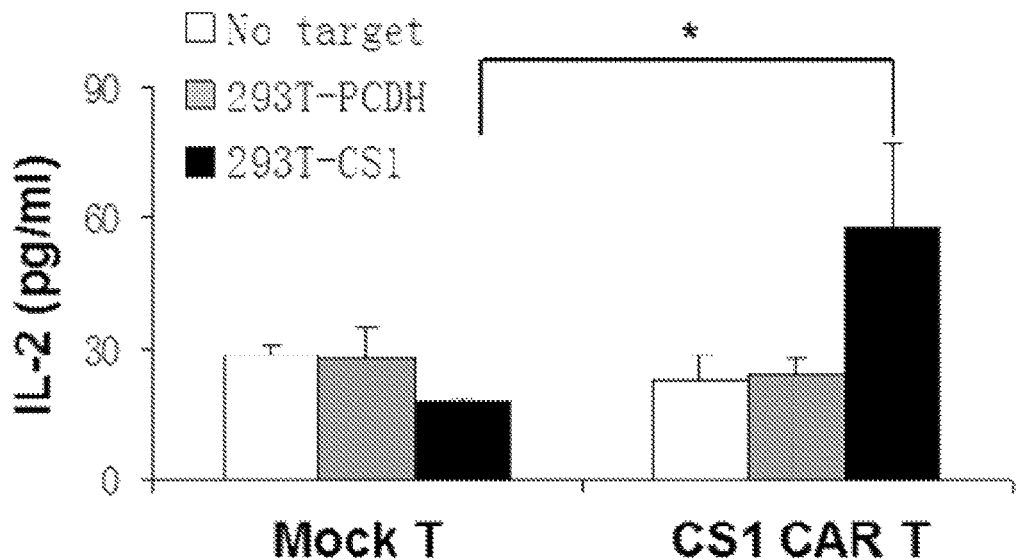

Forced Overexpression of CS1 in Target Cells Enhances Recognition and Killing by CS1-Specific CAR T Cells The considerably stronger response in CS1-CAR T cells in terms of cytokine release and cytotoxicity when stimulated by myeloma cells expressing high levels of CS1 prompted investigation of whether ectopic expression of CS1 in myeloma cells with endogenously low levels of CS1 expression could elicit an increase in cytokine release and cytolysis. To this end, RPMI-8226 myeloma cells with low levels of endogenous CS1 expression were transduced with lentiviruses encoding human CS1 or PCDH empty vector as a mock-transduced control. The transduction efficiency was monitored by detection of GFP protein encoded by the lentiviruses, and the percentage of GFP-positive cells was more than 90% by flow cytometric analysis. Overexpression of CS1 was confirmed by staining the surface of the transduced cells with a PE-conjugated anti-CS1 antibody (FIG. 4A). Chromium-51 release assay indicated that forced CS1 expression resulted in a discernible increase in the susceptibility of RPMI-8226 cells to lysis by CS1-CAR-transduced T cells as opposed to mock-transduced T cells (FIG. 4B). Then, IFN-γ and IL-2 production was assessed via ELISA, showing that, compared with mock-transduced T cells, CS1-CAR-transduced T cells produced significantly higher amounts of IFN-γ and IL-2 in response to RPMI-8226 cells overexpressing CS1; meanwhile, there was only a moderate increase in IFN-γ secretion and no change in IL-2 secretion when CS1-CAR T cells were co-cultured with empty vector-modified RPMI-8226 cells (FIGS. 4C and D). Likewise, overexpression of CS1 in CS1⁻293 T, a transformed cell line, also triggered enhanced cytokine release and cytolysis by CS1-CAR T cells (FIG. 7B-7D). This was consistent with other reports on CAR T cells targeting other tumor antigens (Sanchez C, et al. Prostate Cancer Prostatic Dis 2013 16:123-31; Chinnasamy D, et al. J Clin Invest 2010 120: 3953-68). These findings corroborated that increased recognition and killing of target cells by CS1-CAR T cells occurred in a CS1-dependent manner.

Figure 5A:
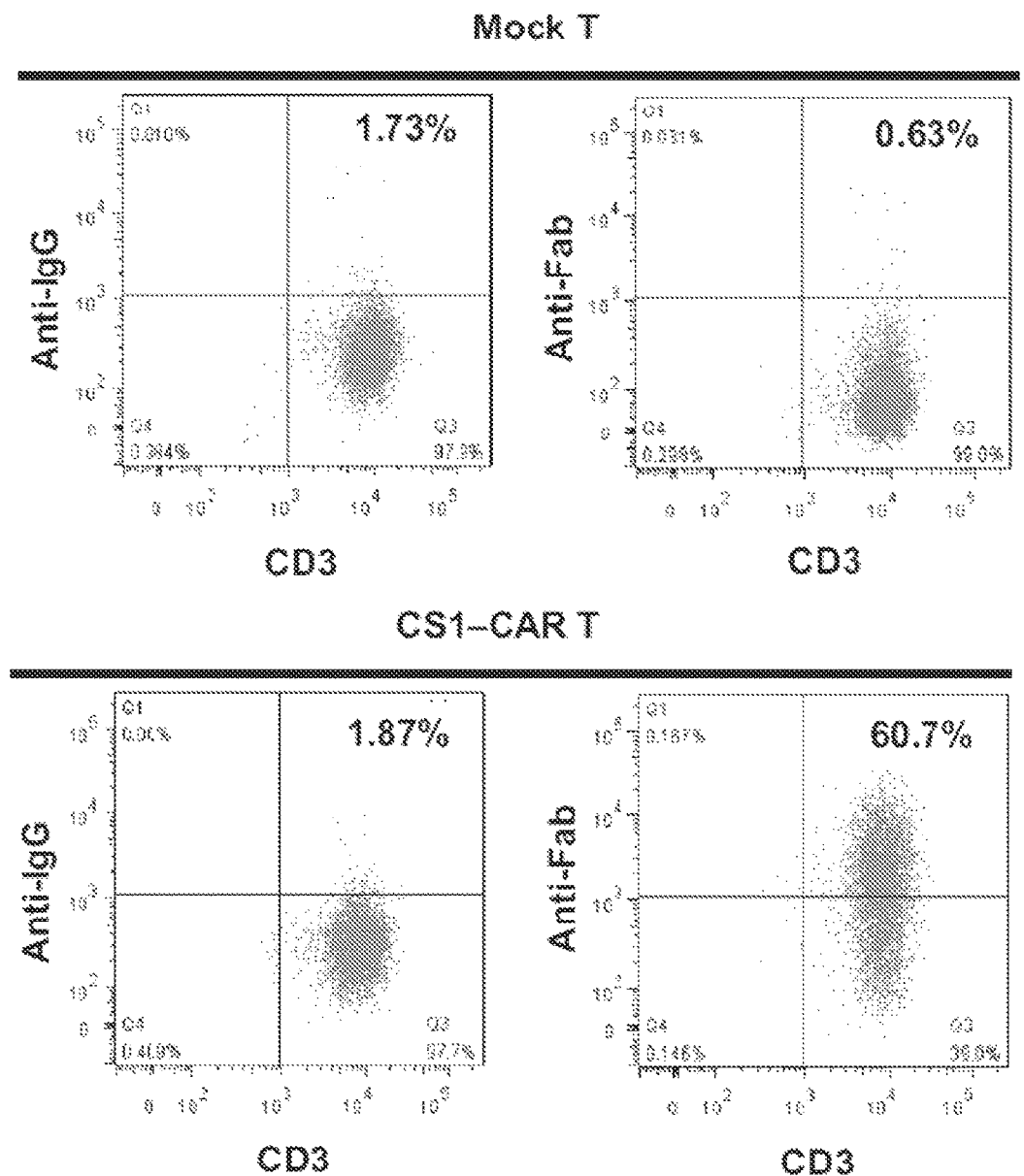
FIGS. 5A to 5D show CS1-CAR T cells specifically recognize and eliminate CS1-expressing human primary myeloma cells ex vivo.
Figure 5B:
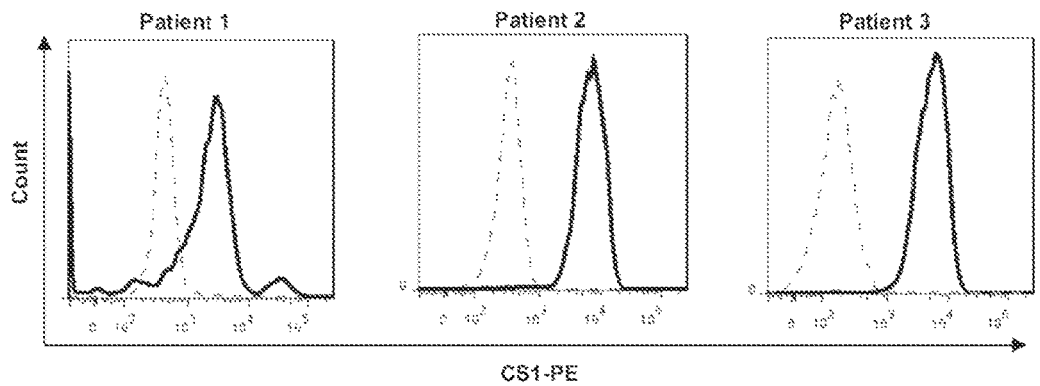
Figure 5C:
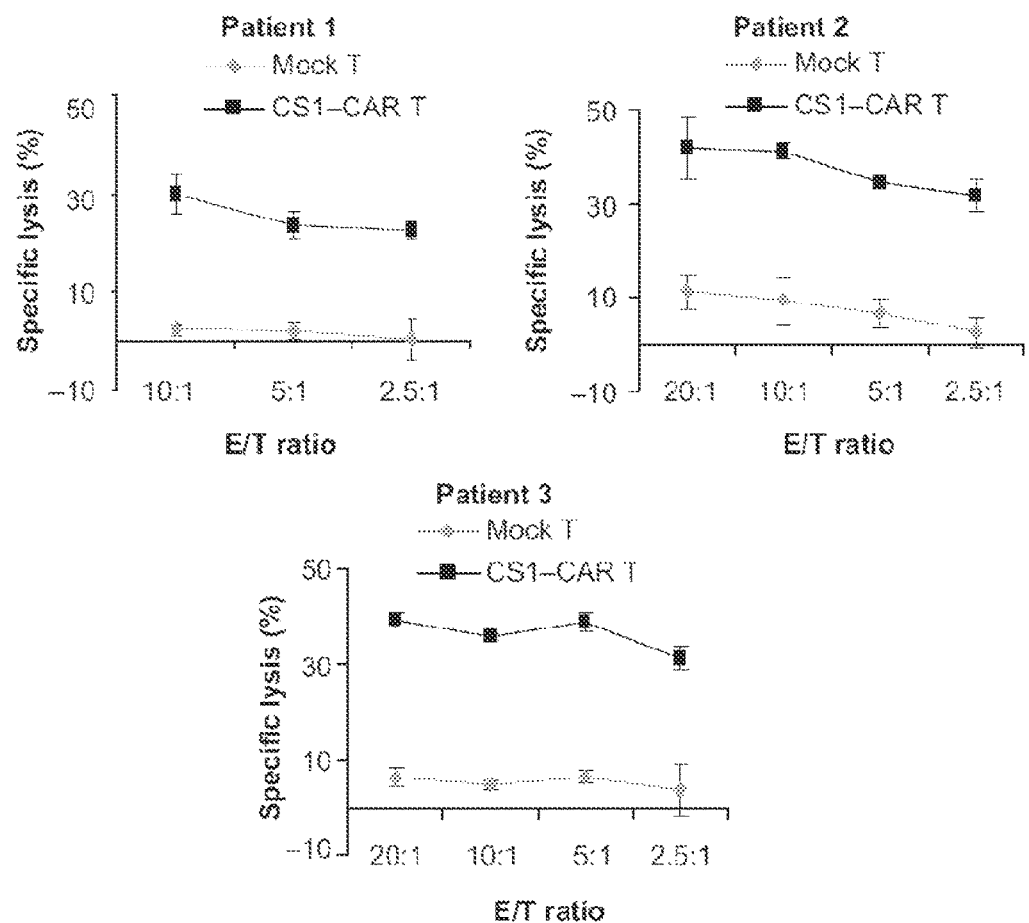
Figure 5D:
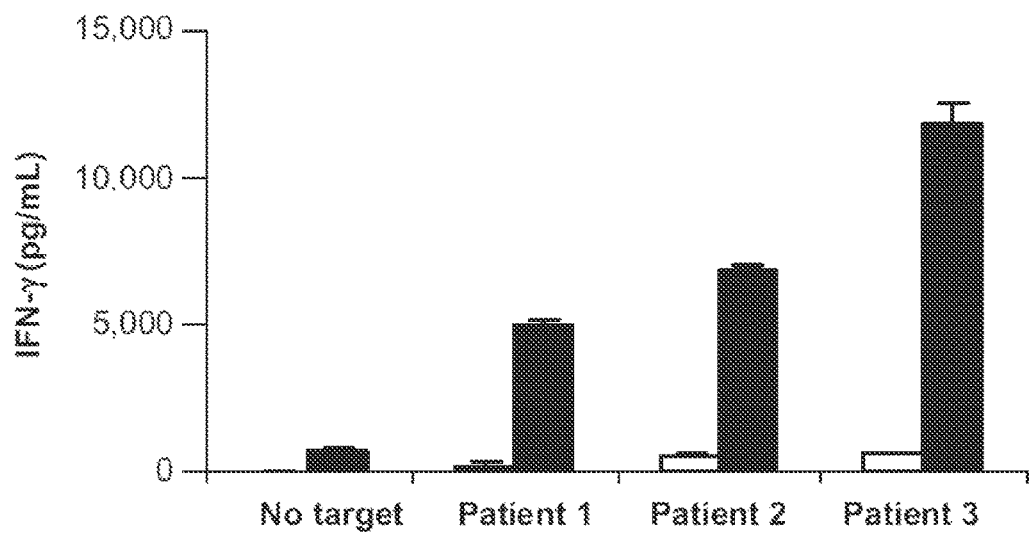

Improved Recognition and Killing of Primary Myeloma Cells by Autologous CS1-Specific CAR T Cells To study the effects of CS1-specific CAR T cells in a more clinically relevant context, it was investigated whether CS1-CAR-transduced autologous T cells could efficiently recognize and kill tumor cells freshly isolated from patients with myeloma. Like T cells from healthy donors, T cells from patients with relapsed myeloma were successfully expanded and manipulated to express CS1-CAR by retroviral infection, as manifested by 60.7% of T cells staining positively with both anti-mouse Fab and anti-human CD3 antibodies determined by flow cytometry (FIG. 5A). Primary CD138+ myeloma cells from patients were isolated using positive magnetic selection, and primary myeloma cells were observed to be uniformly positive for surface expression of CS1 using flow cytometry (FIG. 5B). By chromium-51 release assay, it was observed that myeloma cells from patients were highly resistant to lysis by autologous mock-transduced T cells, but became susceptible to autologous CS1-CAR-transduced T cells even at a low (2.5:1) (E/T) ratio (FIG. 5C). In agreement with these cytotoxicity results, autologous CS1-CAR T cells produced significantly higher amounts of IFN-γ in response to myeloma cells compared with autologous mock-transduced T cells (FIG. 5D). These findings demonstrate that CS1-CAR-equipped T cells can efficiently recognize and eradicate myeloma cells in the autologous setting ex vivo.

Figure 6A:
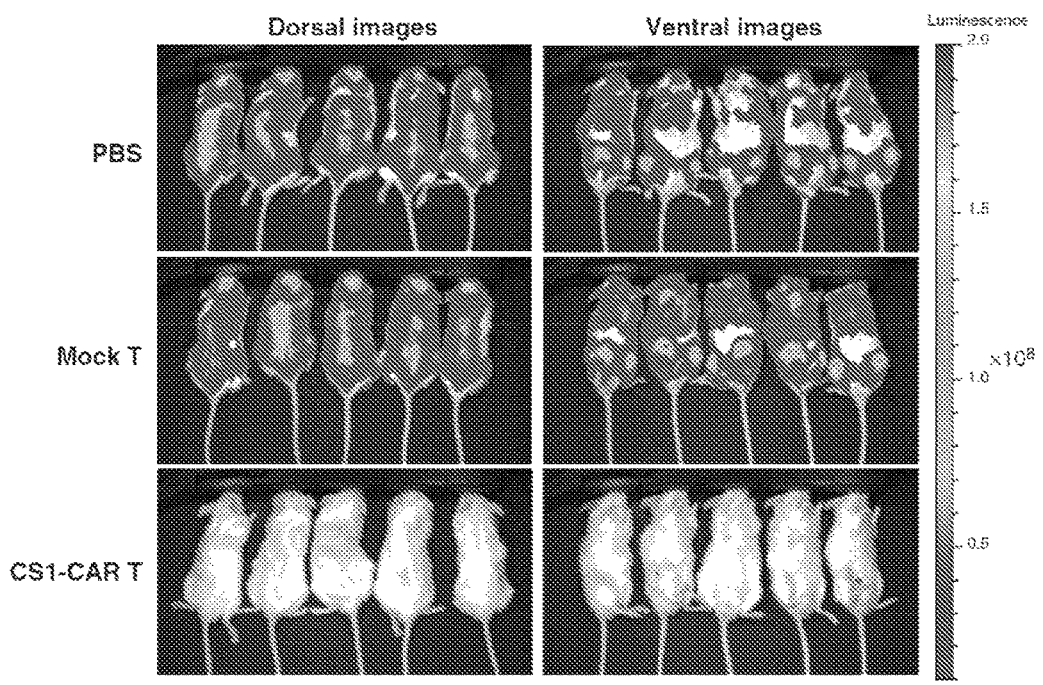
FIGS. 6A and 6B show CS1-redirected T cells inhibit tumor growth and prolong mouse survival in an orthotopic MM.1S xenograft mouse model.
Figure 6B:
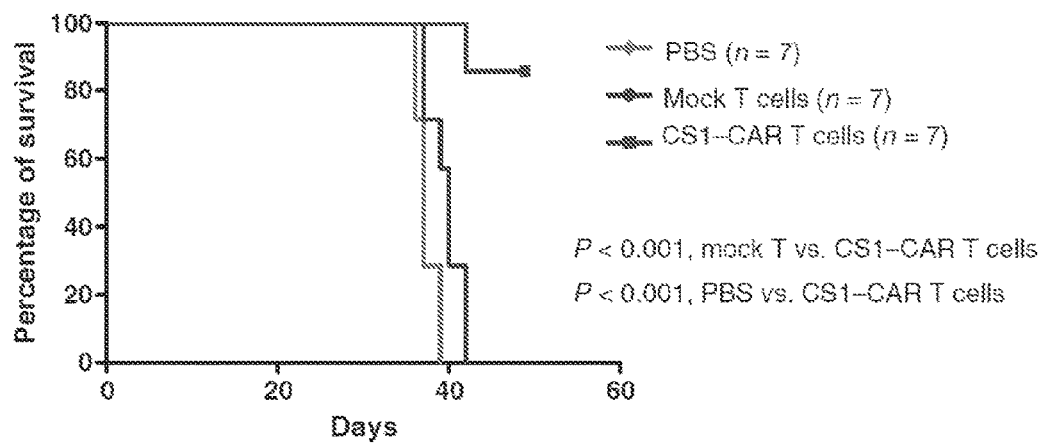

CS1-Directed T Cells Suppress In Vivo Tumor Growth and Prolong Survival of Tumor-Bearing Mice in Orthotopic Xenograft Myeloma Models The therapeutic potential of CS1-CAR T cells was evaluated in an MM.1S-grafted NSG mouse model. Intravenous injection of MM.1S cells has been widely used to establish a mouse xenograft model of MM, because this can lead to the engraftment in bone marrow and bone, as well as consistent establishment of multifocal bone lesions, which closely recapitulates human MM (Mitsiades C S, et al. Cancer Cell 2004 5:221-30; Runnels J M, et al. J Biomed Opt 2011 16:011006). To facilitate monitoring of tumor growth, MM.1S cells were engineered to express both GFP and firefly luciferase by retroviral infection, and GFP+ cells were sorted and intravenously grafted into NSG mice to initiate tumor growth. These mice were then intravenously infused with mock-transduced T cells, CS1-CAR-transduced T cells or PBS. In agreement with the previous reports (Mitsiades C S, et al. Cancer Cell 2004 5:221-30; Runnels J M, et al. J Biomed Opt 2011 16:011006), bioluminescence imaging using IVIS showed that MM.1S-bearing NSG mice in the PBS-treated group developed disseminated tumor lesions in skulls, vertebrae, pelvis, and femurs (FIG. 6A), and the majority of the mice displayed hind leg paralyses 5 weeks after inoculation of tumor cells. Infusion of CS1-CAR T cells remarkably reduced tumor burden as determined by bioluminescence imaging as well as prolonged the overall survival of MM.1S-bearing NSG mice, whereas infusion of mock-infected T cells failed to result in efficient tumor eradication and improved survival of mice (FIGS. 6A and B).

Figure 9A:
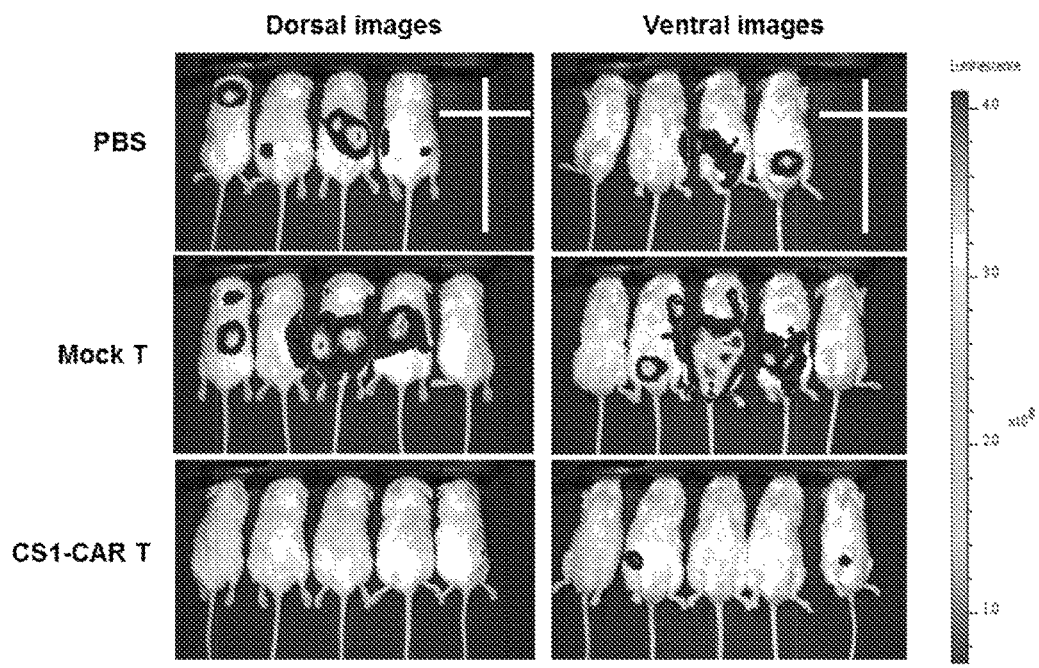
FIGS. 9A and 9B show that CS1-redirected T cells inhibit tumor growth and prolong mouse survival in an orthotopic IM-9 xenograft mouse model.
Figure 9B:
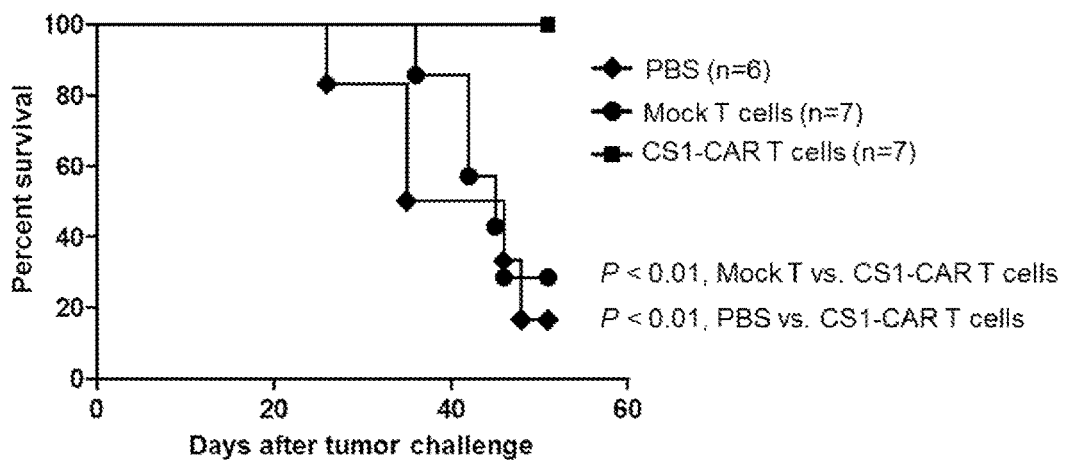
Figure 10A:
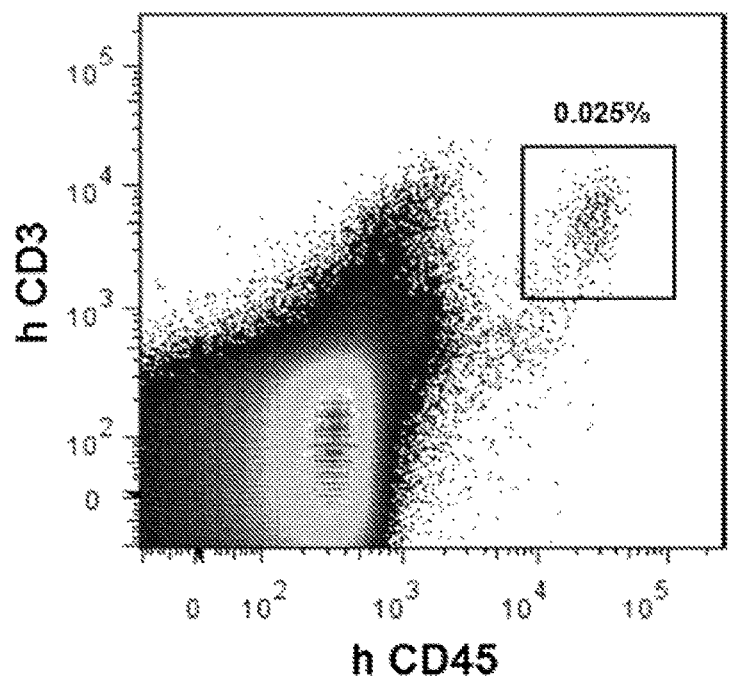
FIGS. 10A to 10C show that CS1-CAR T cells persisted and proliferated in the bone marrow (BM) of MM.1S cell-grafted NSG mice. NSG mice were inoculated with $8\times10^6$ MM.1S cells on day 0, and on day 7 mice were treated with $10\times10^6$ CS1-CAR T cells. On day 20, mice were i.p. injected with 1.5 mg Brdu in DPBS solution. Mice were sacrificed on the following day, and the BM cells were isolated for surface staining with CD45 and CD3 human-specific antibodies and/or anti-Brdu antibodies (BD Biosciences) following the manufacture's protocol.
Figure 10B:
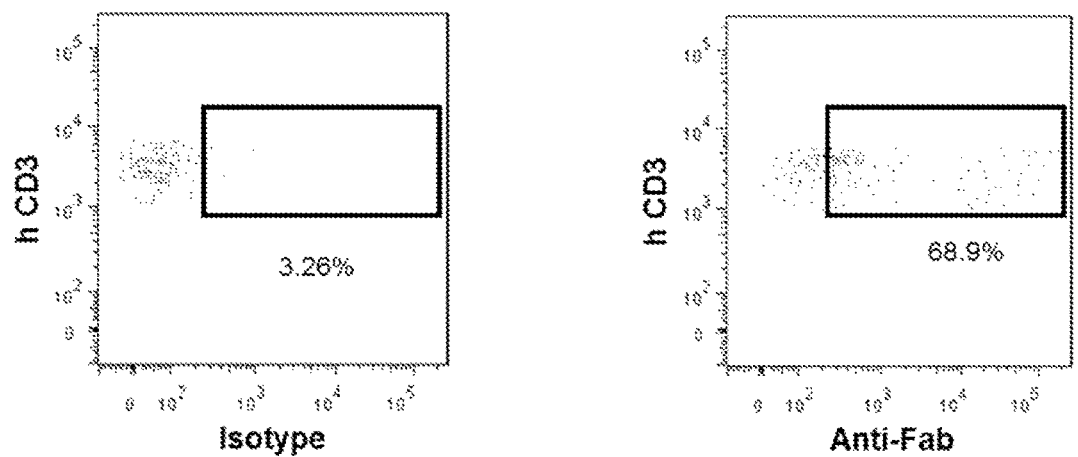
Figure 10C:
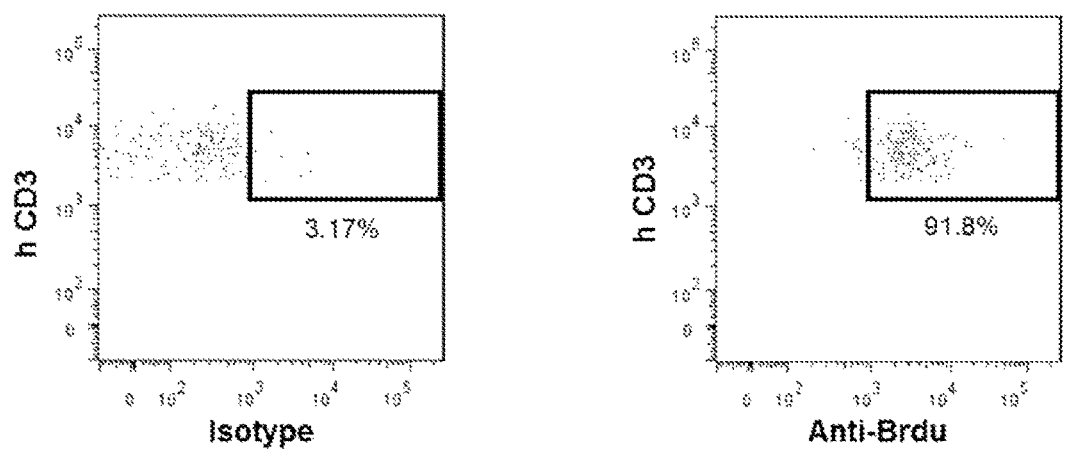
Figure 11C:
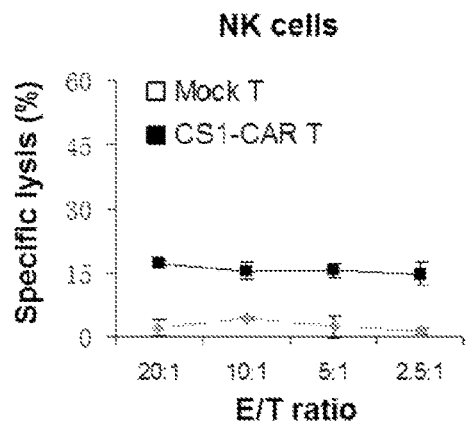
Figure 11C:
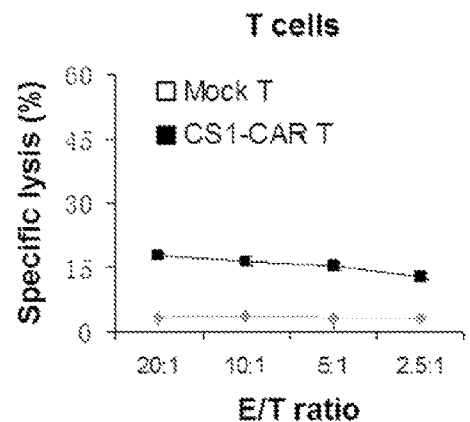
Figure 11C:
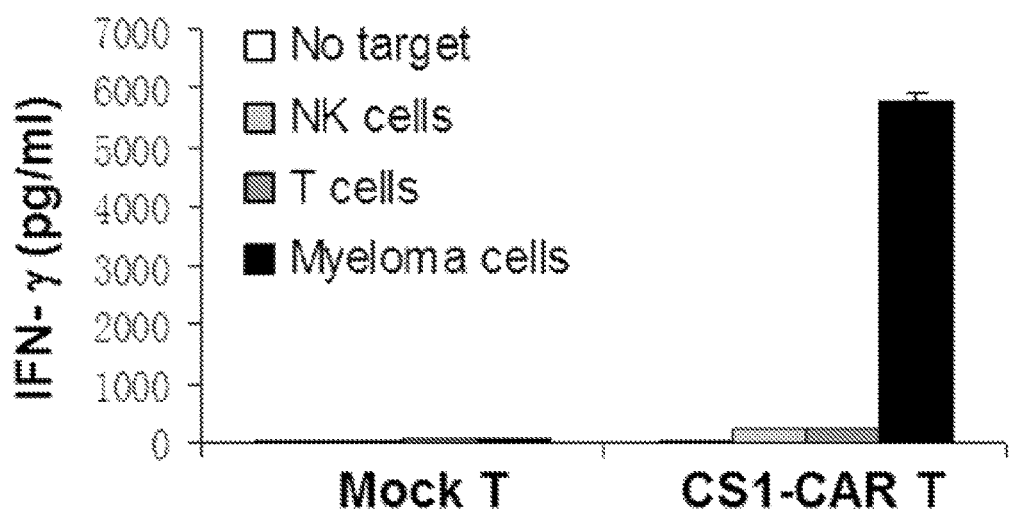
Figure 12:
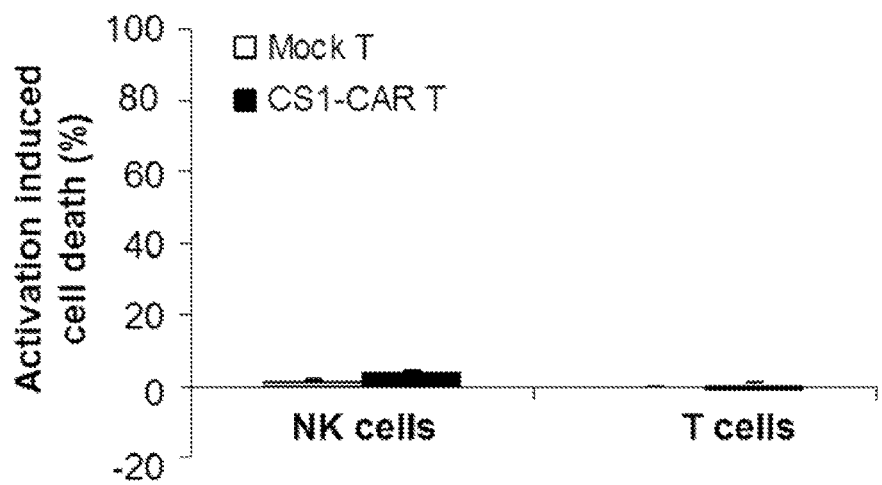
FIG. 12 shows primary NK cells or T cells did not trigger apparent activation induced cell death (AICD) in CS1-CAR T cells. Primary NK cells and T cells were incubated with an equal number of $^{51}$Cr-labelled mock- or CS1-CAR-transduced T cells for 12 h. Specific lysis was then determined using a $^{51}$Cr release assay.

To further validate the in vivo anti-MM capacity of CS1-CAR T cells, the impact of CS1-CAR T cells was evaluated using an IM9-grafted NSG mouse model. Similar data to those shown using MM.1S were observed. Bioluminescence imaging indicated that infusion of CS1-CAR-transduced T cells could efficiently eradicate tumors established in IM9-bearing mice, whereas infusion of mock-transduced T cells failed to reduce tumor burden (FIG. 9A). Forty-four days after the initial treatment, a 100% survival rate was observed for IM9-bearing mice receiving CS1-CAR T-cell infusion, whereas the survival rate was only 28.6% and 16.7% for control mice receiving mock T cells and PBS, respectively (FIG. 9B).

Example 2

CS1-Specific Chimeric Antigen Receptor (CAR)-Engineered Natural Killer Cells Enhance In Vitro and In Vivo Antitumor Activity Against Human Multiple Myeloma In this study, human NK cells were engineered to express a CAR that was CS1 specific, and incorporated a CD28-CD3ζ co-stimulatory signaling domain. The anti-MM function of these cells was evaluated in vitro and in an in vivo orthotopic xenograft mouse model of MM. The results showed that the expression of the CS1-CAR could redirect NK cells to specifically and efficiently eradicate CS1-expressing MM cells, both in vitro and in vivo, and this eradication was CS1 dependent. The data suggest that this CAR strategy is suitable for the development of an effective NK cell-based immunotherapy as a means to treat patients with refractory or relapsed MM. In addition, in contrast to CAR T cells, CAR NK cells allow the use of allogeneic NK cell sources, which are less likely to cause and may even help to suppress graft-versus-host disease (Olson J A, et al. Blood 2010 115:4293-4301), while also potentiating an increase in cytotoxicity due to mismatched killer immunoglobulin-like receptors (KIRs) (Ruggeri L, et al. Science 2002 295:2097-2100).

Materials and Methods

Cell Culture

Human multiple myeloma cell lines L363 (German Collection of Microorganisms and Cell Cultures, Braunschweig, Germany), IM9 [American Type Culture Collection (ATCC), Manassas, Va., USA] and U266 (ATCC) were maintained in RPMI 1640 medium with 10% fetal bovine serum (FBS) (Life Technologies, Grand Island, N.Y., USA). Human IL-2-dependent NK cell lines NK-92 (ATCC) and NKL were maintained in RPMI 1640 medium supplemented with 20% FBS and 150 IU/mL rhIL-2 (Hoffman-LaRoche Inc., Nutley, N.J., USA). 293T (ATCC), and the phoenix packaging cell line was maintained in DMEM medium with 10% FBS. Primary CD138+ MM cells were isolated from bone marrow aspirate of MM patients using the EASYSEP Human Whole Blood and Bone Marrow CD138 Positive Selection Kit (StemCell Technologies, Vancouver, BC, Canada) according to the manufacturer's protocol. All human work was approved by The Ohio State University Institutional Review Board.

Mice

Six- to eight-week-old NOD.Cg-prkdcscid IL2rgtm1Wjl/szJ (NSG) mice were obtained from Jackson Laboratories (Bar Harbor, Me., USA). All animal work was approved by The Ohio State University Animal Care and Use Committee. Mice were monitored frequently for MM disease progression, and killed when they were moribund with the symptoms of hindlimb paralysis, lethargy, and obvious weight loss.

Generation of Anti-CS1 CAR Lentiviral Construct

The CS1-scFv fragment, amplified from the hybridoma cell line Luc90, was fused with a sequence encoding a Myc tag immediately following the CS1-VL-encoding sequence. The fused DNA sequences were incorporated with CD28-CD3ζ that was incised from a retroviral vector. The entire CS1-scFv-myc tag-CD28-CD3ζ fragment was ligated into a lentiviral vector designated as PCDH-CMV-MCS-EF1-copGFP (PCDH, System Biosciences, Mountain View, Calif., USA) to generate a PCDH-CS1-scFv-myc tag-CD28-CD3ζ (PCDH-CS1-CAR) construct.

Lentivirus Production and Transduction of NK Cells

To produce VSVG-pseudotyped lentiviral supernatant, 293T cells cultured in DMEM media (Invitrogen) were co-transfected with PCDH-CS1-scFv-CD28-CD3ζ or the PCDH control vector (to generate virus for mock infection with the empty vector) together with the packaging constructs, pCMV-VSVG and pCMV-dr9, using calcium phosphate transfection reagent (Promega, Madison, Wis., USA). After 24 h, the DMEM media was replaced with RPMI-1640 media containing 20% FBS. 48 h after transfection, conditioned medium containing lentivirus was harvested and filtered through a 0.45 μm filter unit (Millipore, Billerica, Mass., USA) to remove cell debris. Viral infection was performed in 6-well plates using $2 \times 10^6$ NK-92 or NKL cells in a total volume of 2 mL of lentiviral supernatant containing 8 μg/mL polybrene (Sigma-Aldrich, St. Louis, Mo., USA) and 450 IU/mL rhIL-2. Cells were centrifuged at 1,800 rpm at 32° C. for 45 min, then plates were placed in an incubator at 37° C. for 2 h. Infection was then repeated a second time on the same day, and one additional time the following day. After the third transduction, cells were maintained in RPMI 1640 media supplemented with 20% FBS and 150 IU/mL rhIL-2 at 37° C. Transduced NK cells were enriched by two rounds of cell sorting using a FACS Aria II cell sorter (BD Biosciences, San Jose, Calif., USA). Positive cells were selected based on expression of green fluorescence protein (GFP) surface marker, which was encoded in the PCDH vector Generation of a U266 Cell Line Stably Expressing CS1

Human CS1 coding sequences were amplified from cDNA isolated from IM9 cells via PCR, then subcloned into a PCDH lentiviral vector to generate a PCDH-CS1 construct. Lentivirus production and infection of U266 cells were performed using the methods described above. GFP-positive cells were then sorted using an FACS Aria II cell sorter (BD Biosciences, San Jose, Calif., USA).

Immunoblotting Analysis

Cells were washed with PBS and directly lysed in laemmli buffer. Lysates were electrophoretically separated on a 4% to 15% gradient SDS-PAGE gel (Bio-Rad Laboratories, Hercules, Calif., USA) and transferred to a nitrocellulose membrane (EMD Millipore, Billerica, Mass., USA). The membrane was blocked with 5% milk in Tris Buffered Saline (TBS) supplemented with 0.1% Tween 20. Mouse anti-human CD3ζ chain monoclonal antibody (BD Pharmingen, San Diego, Calif., USA) was diluted 1:1,000 with 5% milk in TBS supplemented with 0.1% Tween 20, and this antibody solution was added to react with the membrane overnight. The membrane was then washed three times in TBS supplemented with Tween 20. The HRP-conjugated secondary antibody (GE Healthcare Biosciences, Pittsburgh, Pa., USA) was diluted 1:5,000 with 5% milk in TBS supplemented with 0.1% Tween 20 and added to the membrane to stand for 1 h. The membrane was again washed four times in TBS supplemented with Tween 20, and an enhanced chemiluminescence reagent (ECL; GE Healthcare Biosciences) was added for 1 min. The blot was then exposed to film for various lengths of time to generate a properly exposed image.

Flow Cytometry

To analyze surface expression of CS1-CAR, a single cell suspension of transduced NK cells was incubated for 1 h at 4° C. with an anti-Myc tag mouse mAb 9E10 (Sigma-Aldrich). Cells were washed twice with PBS and then incubated for 30 min at 4° C. with PE-conjugated rat anti-mouse IgG1 secondary antibody (BD Pharmingen). Surface expression of CS1 and CD138 on myeloma cells was examined by FACS analysis using a BD LSRII analyzer after cells were stained with PE-conjugated mouse anti-CS1 mAb (eBiosciences, San Diego, Calif., USA) and APC-conjugated mouse anti-CD138 mAb (BD Pharmingen). Data analysis was carried out using FLOWJO software (Tree Star Inc., Ashland, Oreg., USA).

Cytotoxicity Assay

For detection of NK cell-mediated lysis, MM target cells were labeled for 1.5 h with 100 mCi chromium-51 ($^{51}$Cr), washed four times with regular RPMI media, and adjusted to a concentration of 5,000 cells per well in 100 μl volume of a 96-well V-bottom microtiter plate. FACS-enriched mock- or CS1-CAR-transduced NK cells were added in 100 μl volume into triplicate wells at various effector to target (E:T) ratios. After 4 h of incubation at 37° C., 100 μl of supernatant was harvested from each well, and transferred to scintillation vials containing a liquid scintillation cocktail (Fisher scientific, Pittsburgh, Pa., USA) so that release of $^{51}$Cr could be measured on a TOPCOUNT counter (Canberra Packard, Meriden, Conn., USA). To determine maximal $^{51}$Cr release, target cell suspension was incubated with 100 μl of SDS. Percentage of specific lysis was calculated using the standard formula: 100×(cpm experimental release−cpm spontaneous release)/(cpm maximum release−cpm spontaneous release).

Interferon-γ Release Assay

Myeloma target cells were co-cultured with NK effector cells in 96-well V bottom plates for 24 h. In all, $2.5 \times 10^5$ myeloma cell line cells or $1.0 \times 10^5$ primary myeloma cells were incubated with $2.5 \times 10^5$ or $5.0 \times 10^5$ NK cells, respectively. Cell-free supernatants were assayed for interferon-γ (IFN-γ) secretion by enzyme-linked immunosorbent assay (ELISA) using a kit from R&D Systems (Minneapolis, Minn., USA) according to the manufacturer's protocol. Data depicted in Figures represent mean values of triplicate wells from one of three representative experiments with similar results.

An Orthotopic MM Mouse Model and In Vivo Treatment of MM-Bearing Mice and Bioluminescence Imaging IM9 cells were retrovirally transduced with Pinco-pGL3-luc/GFP virus expressing firefly luciferase as previously described (He S, et al. Blood 2013 121:4663-4671). GFP-positive cells were sorted using an FACS Aria II cell sorter (BD Biosciences), and were designated as 'IM9-Luc' cells. Then, six- to eight-week-old male NSG mice were intravenously (i.v.) injected with $0.5 \times 10^6$ IM9-Luc MM cells in 400 μl of phosphate-buffered saline via tail vein on day 0 to establish a xenograft orthotopic MM model. Beginning on day 7, the mice were i.v. injected with $5 \times 10^6$ effector cells, that is, CS1-CAR NK-92 cells or mock-transduced control cells, in 400 μl of phosphate-buffered saline once every 5 days (five times in total). Four weeks after IM9-Luc inoculation, the mice were intraperitoneally (i.p.) infused with D-luciferin (150 mg/kg body weight; Gold Biotechnology, St. Louis, Mo., USA), anesthetized with isoflurane, and imaged using an In Vivo Imaging System (IVIS-100, Perkin-Elmer, Waltham, Mass., USA) with the Living Image software (Perkin-Elmer).

Immunohistochemical Analysis

Spinal vertebrae were fixed in 10% buffered formalin phosphate and decalcified in saturated EDTA, and then embedded in paraffin. Five-micron thick sections were stained with hematoxylin and eosin (H&E) for histological examination. The sections were immunostained for identification of human MM cells with mouse anti-human CD138 mAb (1:50 dilution; Thermo-Scientific, Waltham, Mass., USA) following standard immunohistochemistry staining procedures. Horseradish peroxidase-conjugated anti-mouse IgG was used as a secondary antibody, followed by a peroxidase enzymatic reaction.

Statistics

Unpaired Student's t test was utilized to compare two independent groups for continuous end points if normally distributed. One-way ANOVA was used when three or more independent groups were compared. For non-normally distributed end points, such as in vivo bioluminescence intensity, a Kruskal-Wallis test was utilized to compare the median of NK-92-CS1-CAR to NK-92-EV and phosphate-buffered saline groups. For survival data, Kaplan-Meier curves were plotted and compared using a log-rank test. All tests are two-sided. P-values were adjusted for multiple comparisons by the Bonferroni method. A P-value of <0.05 is considered as statistically significant.

Results

Generation of NK-92 and NKL NK Cells Expressing CS1-CAR

Figure 13A:
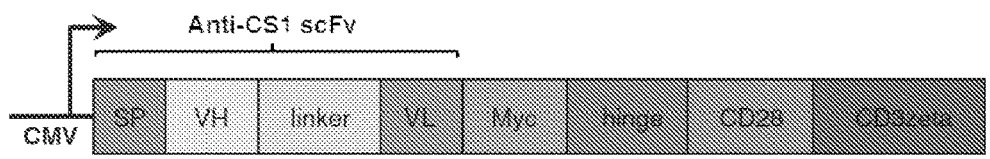
FIGS. 13A to 13C show the generation of a CS1-specific CAR and its expression in CAR-transduced NK cells.
Figure 13B:
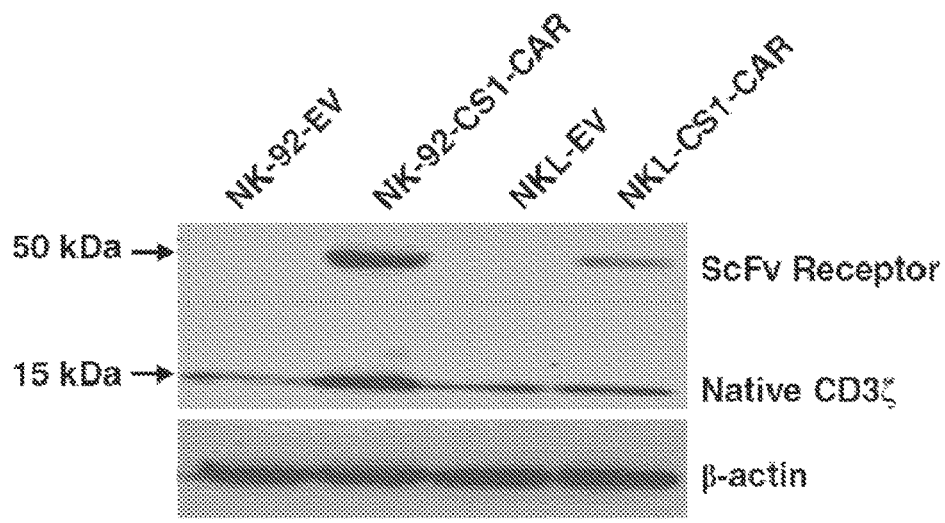
Figure 13C:
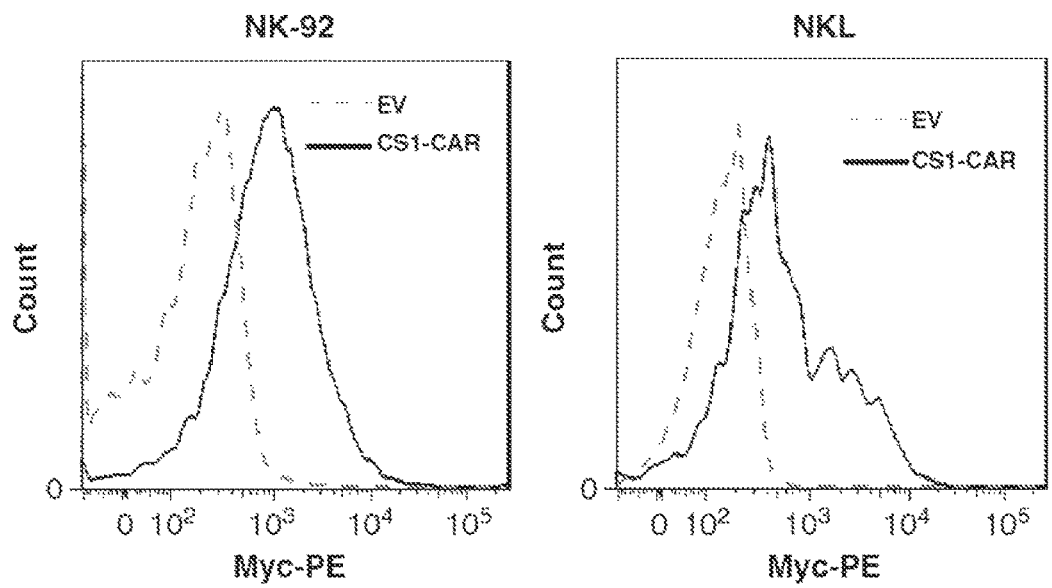

A specific CS1-CAR construct was generated with a PCDH lentiviral vector backbone, sequentially containing a signal peptide (SP), a heavy chain variable region (VH), a linker, a light chain variable region (VL), a Myc tag, a hinge, CD28 and CD3ζ (FIG. 13A). NK-92 and NKL NK cell lines were transduced with the CAR construct and then sorted for expression of GFP, a marker expressed by the vector. Western blotting of the sorted cells demonstrated that CS1-CAR was successfully introduced and expressed, as evidenced by the expression of the chimeric CS1-scFv receptor containing CD3ζ in both NK-92 and NKL cell lines transduced with the CAR construct rather than with the control vector (FIG. 13B). Moreover, a flow cytometric analysis after anti-Myc Ab surface staining indicated that CS1-CAR was expressed on the surface of both NK-92 and NKL cells transduced with the CS1-CAR construct (FIG. 13C).

Figure 14A:
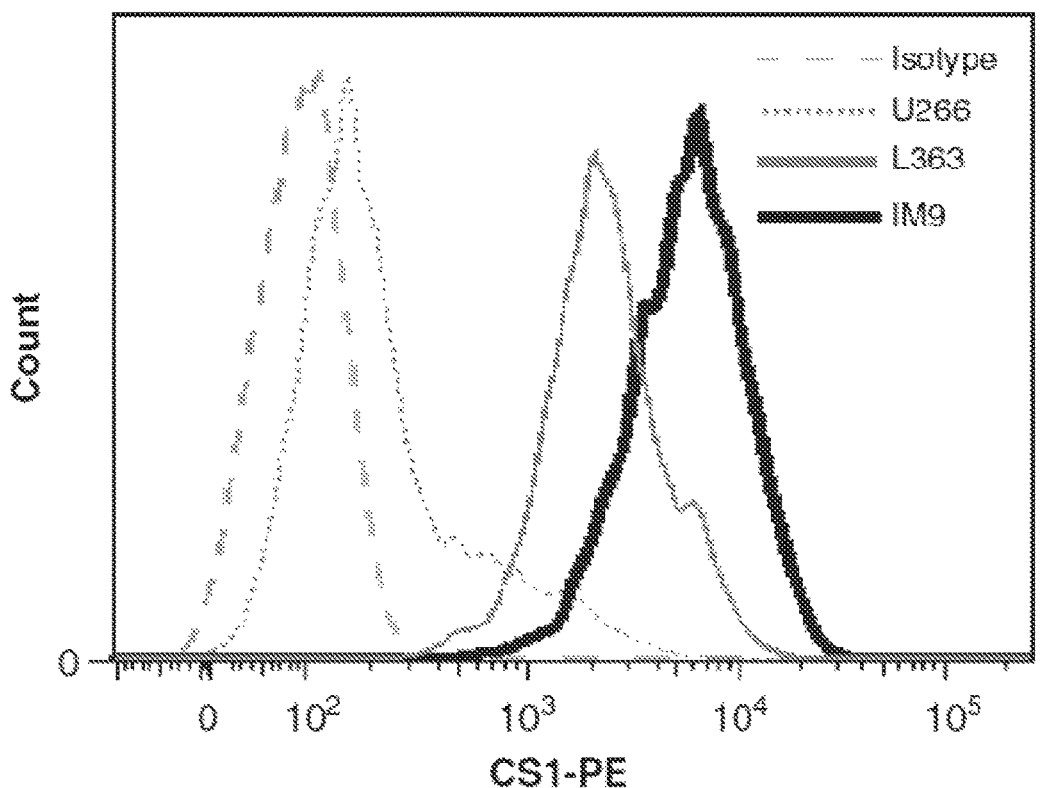
FIGS. 14A to 14D show CS1-CAR NK cells eradicate CS1$^+$ but not CS1$^-$ MM cells.
Figure 14B:
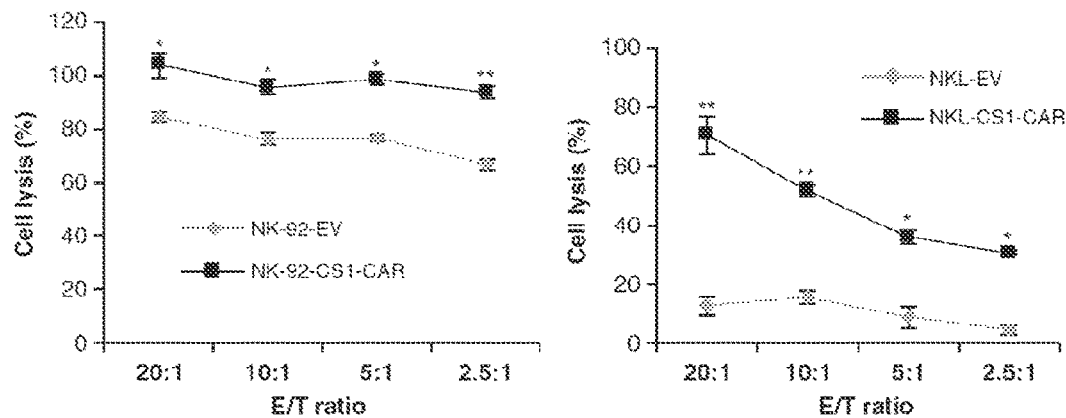
Figure 14C:
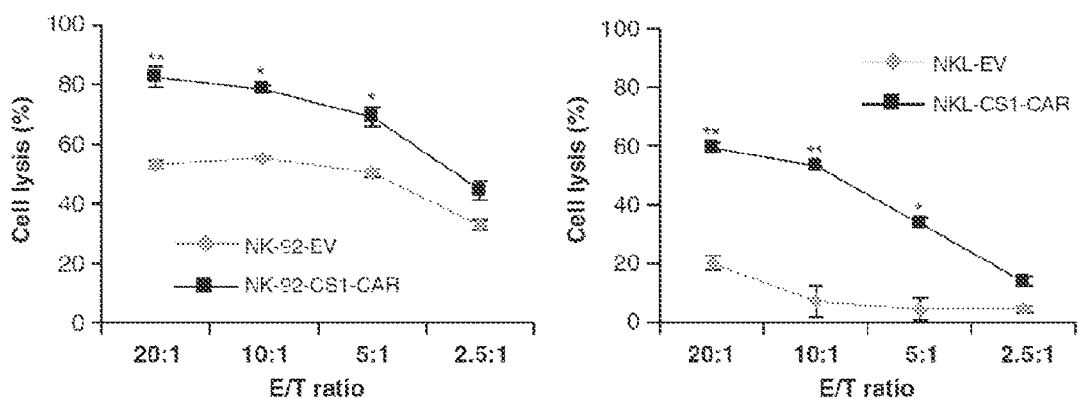
Figure 14D:
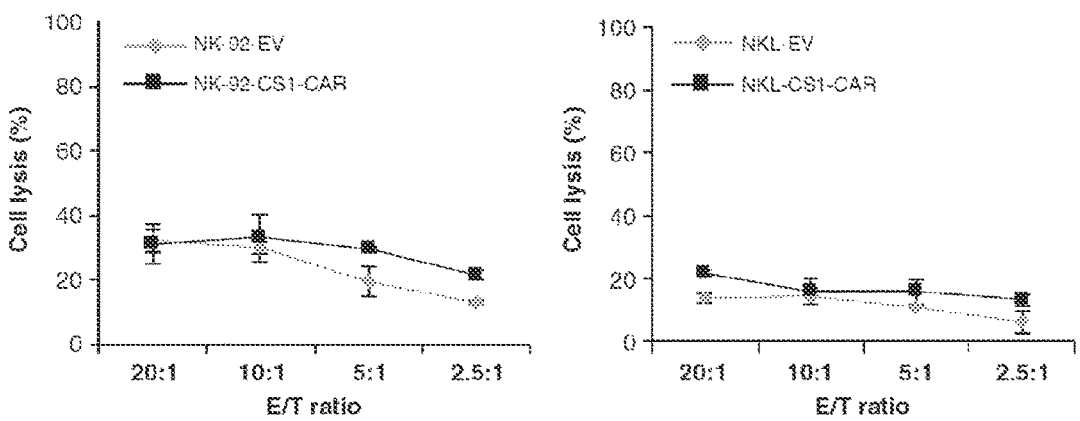
Figure 20:
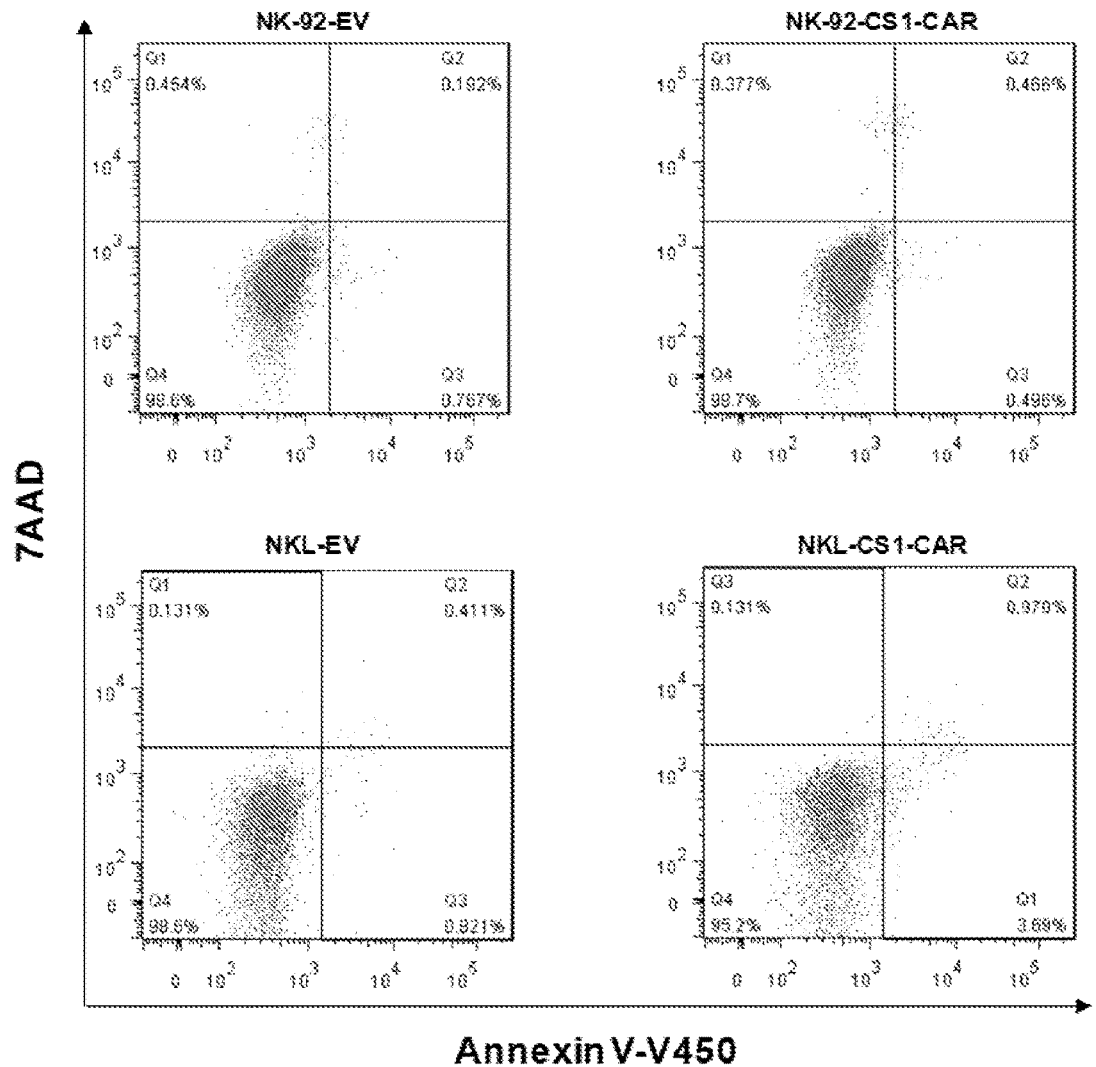
FIG. 20 shows that introduction of CS1 CAR does not lead to substantial apoptosis in NK cell lines. Mock- or CS1-CAR-transduced NK92 or NKL cells were stained with 7AAD and Annexin V-V450, followed by a flow cytometric analysis. NK-92-EV and NKL-EV indicate empty vector (EV) control-transduced NK-92 and NKL cells, respectively. NK-92-CS1-CAR and NKL-CS1-CAR indicate transduction of NK-92 and NKL cells, respectively, with a CS1-CAR construct.

CS1-CAR-Modified NK Cells More Effectively Eradicate CS1$^+$ MM Cells, but not CS1$^-$ Cells, In Vitro in Comparison with Mock-Transduced NK Cells After generating the CS1-CAR NK cells, it was determined whether they selectively kill CS1$^+$ better than CS1$^-$ MM cells. For this purpose, it was first confirmed that IM9 and L363 MM cell lines constitutively expressed CS1 protein on their surface, while expression of CS1 was negligible in U266 MM cells (FIG. 14A). Next, a 4-h chromium-51 release assay indicated that, compared with mock-transduced NK-92 cells, NK-92 cells transduced with CS1-CAR were significantly enhanced in their ability to kill CS1$^+$ IM9 and L363 cells (FIGS. 14B and 14C, left panels). Similar data were observed in experiments repeated using NKL cells transduced with CS1-CAR (FIGS. 14B and 14C, right panels). However, both the CS1-CAR- and mock-transduced NK-92 or NKL cells were similar in their low levels of cytotoxicity against CS1U266 myeloma cells (FIG. 14D). In addition, forced expression of CS1-CAR did not induce obvious apoptosis in NK-92 or NKL cells as determined by analyses of 7AAD/Annexin V-staining using flow cytometry (FIG. 20), suggesting that CS1-CAR expression did not cause cytotoxicity to the NK-92 or NKL cells themselves. Similarly, CS1-CAR expression in purified primary human NK cells augmented their cytotoxicity against CS1$^+$ IM9 myeloma cells.

Figure 15A:
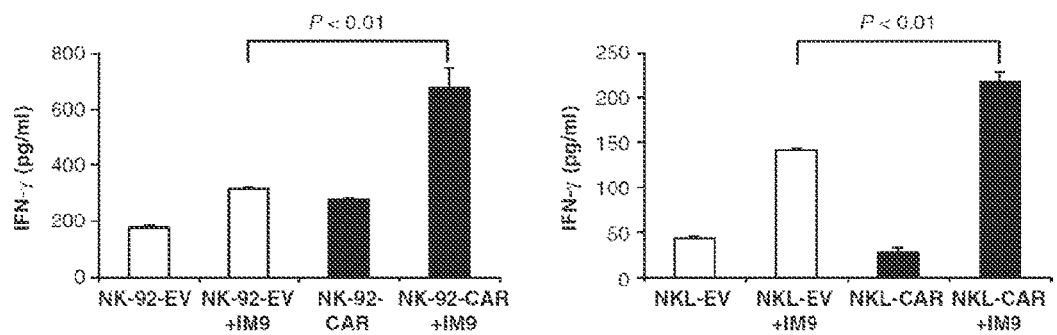
FIGS. 15A to 15C show recognition of CS1$^+$ MM cells induces a stronger response from CS1-CAR NK cells than from control NK cells.
Figure 15B:
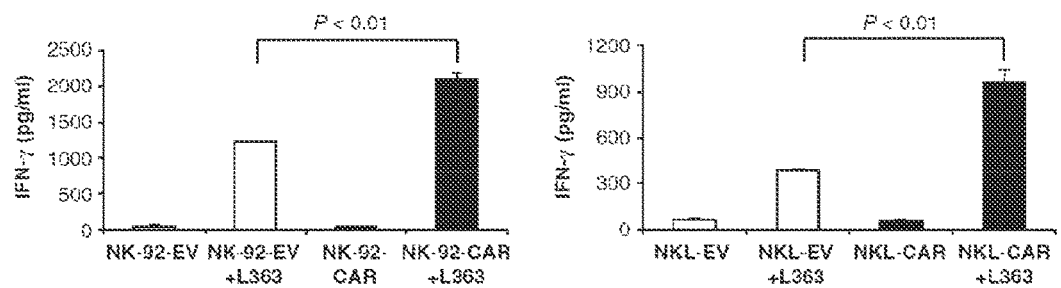
Figure 15C:
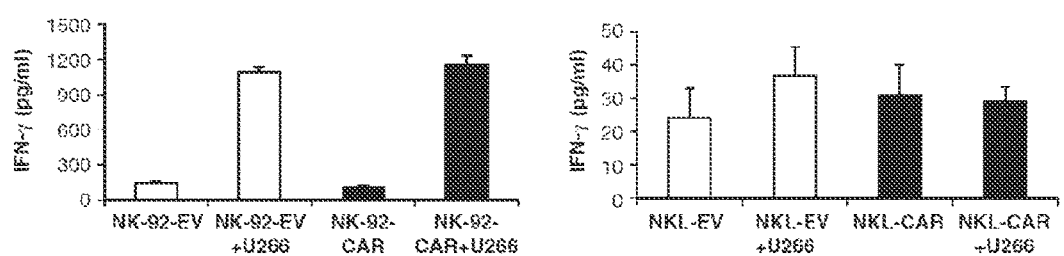

CS1-CAR-Modified NK Cells Secrete More IFN-γ than Mock-Transduced NK Cells do after Exposure to CS1$^+$ MM Cells The signaling domain of the CD28 co-stimulatory molecule, which was included in the CAR construct, may enhance activation after recognition of the CS1 scFv with the CS1 antigen on the surface of MM cells. Therefore, the inclusion of this signaling domain may have the capacity to activate NK cells not only to have higher cytotoxicity, but also to produce more IFN-γ, the latter of which is also important for tumor surveillance and activation of CD8$^+$ T cells and macrophages (Martin-Fontecha A, et al. Nat Immunol 2004 5:1260-1265; Tu S P, et al. Cancer Res 2011 71:4247-4259; Ma J, et al. Cell Mol Life Sci 2003 60:2334-2346). To test this, CS1-CAR-modified or control-engineered effector NK cells were either cultured alone or co-cultured with CS1$^+$ myeloma cells including the IM9 and L363 MM cell lines. After 24 h, the IFN-γ production was measured by ELISA. As shown in FIG. 15, both CS1-CAR-modified and mock-transduced NK-92 or NKL cells spontaneously produced low or negligible levels of IFN-γ when incubated alone. Co-culture with CS1$^-$MM tumor cells (IM9 or L363) induced IFN-γ in both CS1-CAR and mock-transduced NK-92 or NKL cell lines; however, significantly higher levels of IFN-γ were produced by CAR-modified NK-92 or NKL cells than by mock-transduced NK-92 (FIGS. 15A and 15B, left panels) or NKL cells (FIGS. 15A and 15B, right panels). When co-cultured with the CS1$^-$MM cell line, U266, both mock-transduced and CS1-CAR-transduced NK-92 cells but not the transduced NKL cells produced higher levels of IFN-γ than corresponding cells that had not been co-cultured with U266 cells (FIG. 15C). This suggests that a unique interaction between NK cell receptors on NK-92 cells and their ligands on U266 cells may induce CS1-independent IFN-γ production by NK-92 cells. Moreover, CS1-CAR-transduced NK-92 and NKL cells failed to produce more IFN-γ than corresponding mock-transduced NK-92 and NKL cells when they were co-cultured with U266 cells (FIG. 15C). These results are in agreement with the aforementioned cytotoxicity data, and together indicate that modification with CS1-CAR can dramatically enhance NK cell effector functions, in terms of both cytotoxicity and IFN-γ production, in response to CS1$^+$ but not to CS1$^-$ myeloma cells.

Figure 16C:
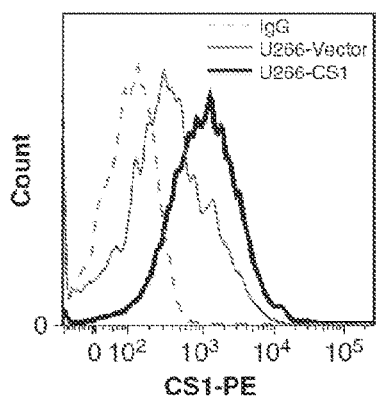
Figure 16C:
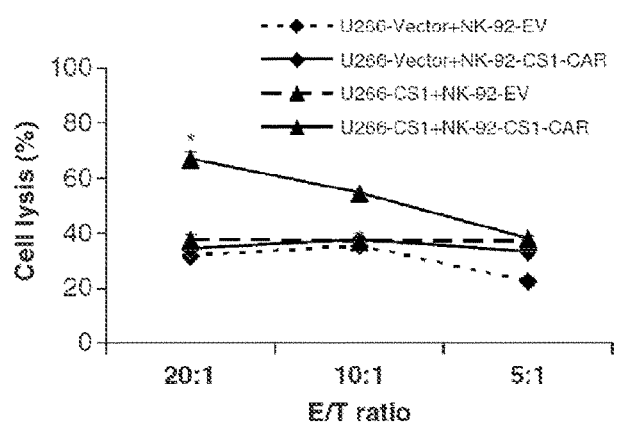
Figure 16C:
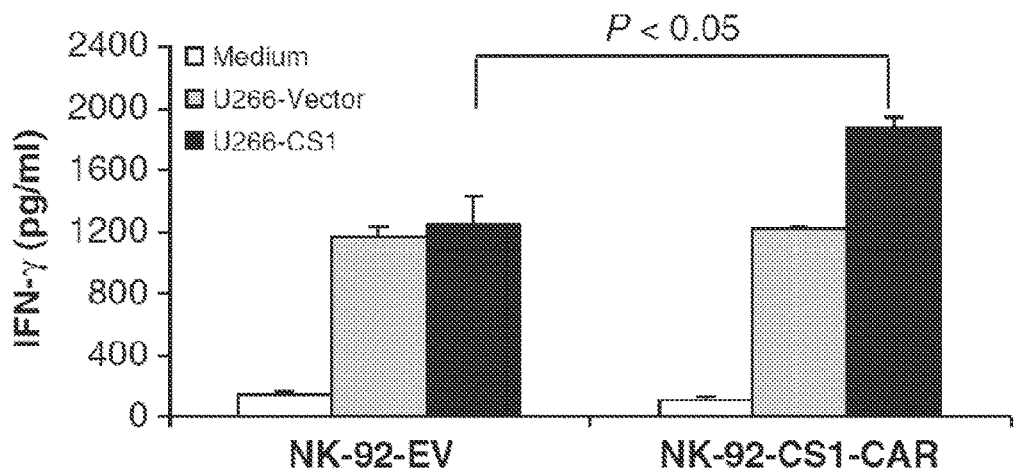

Enforced CS1 Expression in U266 Cells Enhances Cytotoxicity and IFN-γ Production of NK-92-CS1-CAR Cells It was next explored whether this enhanced activity of CS1-CAR NK cells relies on CS1 antigen expression on MM cells. The aforementioned observation—that the introduction of CS1-CAR conferred NK-92 cells with increased cytotoxic activity and enhanced IFN-g production in response to CS1$^+$ myeloma cells, but not to CS1$^-$ U266 myeloma cells—prompted investigation of whether CS1 overexpression in U266 cells is sufficient to change the sensitivity of U266 cells to NK-92-CS1-CAR cells. For this purpose, CS1 was ectopically expressed in U266 cells by lentiviral infection. Flow cytometric analysis confirmed that CS1 protein was successfully expressed on the surface of the U266-CS1 cells (FIG. 16A). Chromium-51 release assay indicated that, when compared with mock-transduced NK-92 cells, there was a significant increase in the cytotoxic activity of CS1-CAR-transduced NK-92 cells toward U266 cells overexpressing CS1 (FIG. 16B). Likewise, compared with parallel co-cultures containing mocktransduced NK-92 cells, NK-92-CS1-CAR cells co-cultured with U266 cells overexpressing CS1 secreted significantly higher levels of IFN-g (FIG. 16C). However, consistent with data in FIGS. 14D and 15C, there was no difference in cytotoxicity and IFN-γ secretion between NK-92-CS1-CAR cells and mock-transduced NK-92 cells when they were incubated with U266 cells transduced with an empty vector control (FIGS. 16B and 16C). These results suggested that the increased recognition and killing of myeloma cells by NK-92-CS1-CAR cells occurs in a CS1-dependent manner.

Phenotypic Characterization of NK-92-CS1-CAR Cells

Figure 17A:
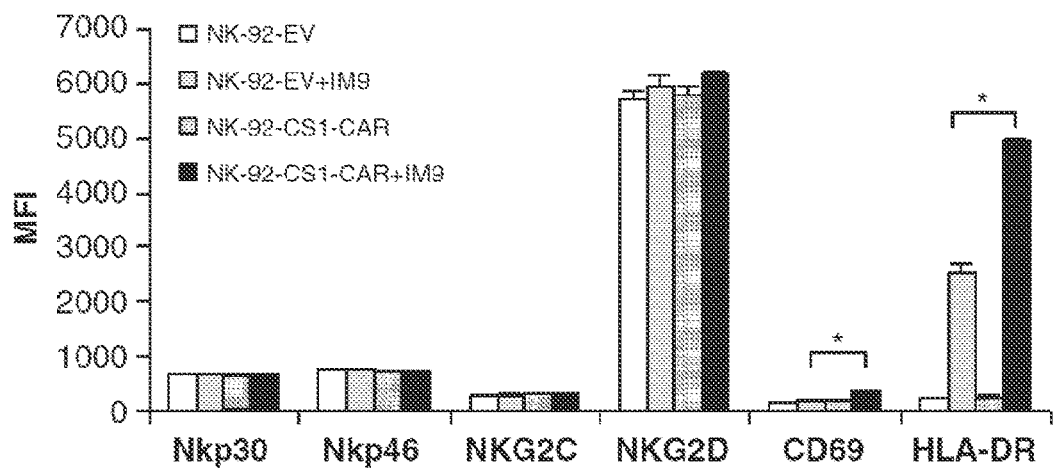
FIGS. 17A to 17C show phenotypic characterization of CS1-CAR modified NK cells.
Figure 17B:
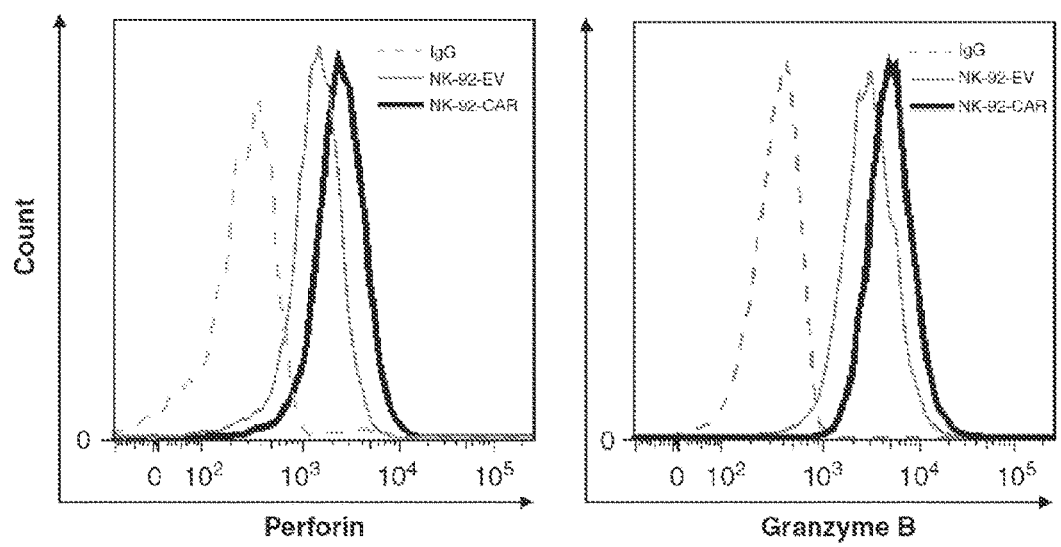
Figure 17C:
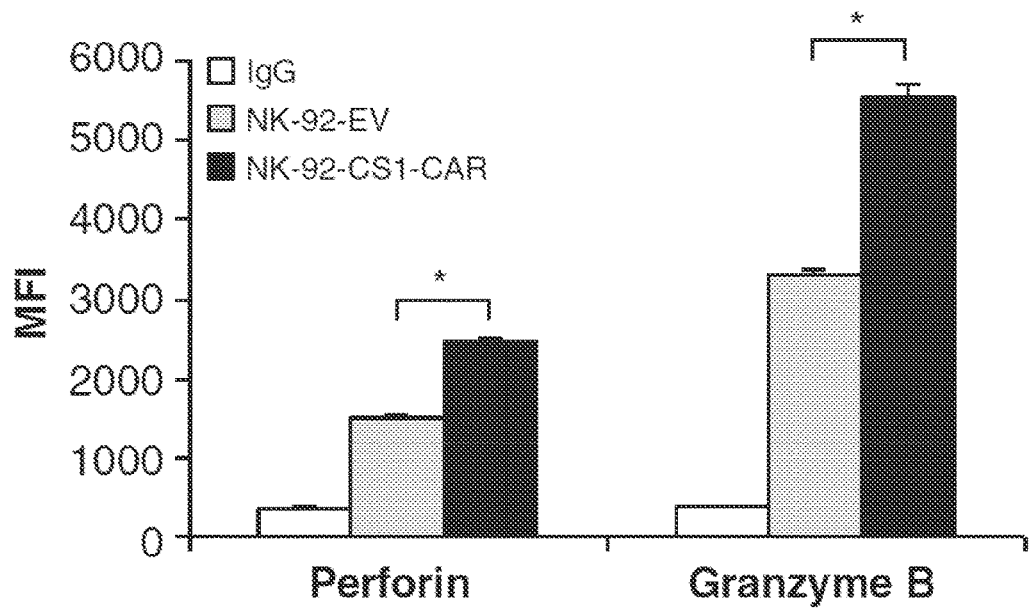

It was next investigated whether the expression of a CS1-specific CAR could change the NK cell phenotype. Flow cytometry was used to compare expression of antigens on the surface of CS1-CAR-transduced and mock-transduced NK-92 cells, following culture in the presence or absence of IM9 myeloma cells. As shown in FIG. 17A, there was no difference between CS1-CAR- and mock-transduced NK-92 cells, whether cultured in the presence or absence of IM9 cells, in the expression of NK cell receptors including NKp30, NKp46, NKG2C and NKG2D. Expression of the NK cell activation markers, CD6928 and HLA-DR (Phillips J H, et al. J Exp Med 1984 159:993-1008; Spits H, et al. Immunity 2007 26:11-16) was also assessed. Recognition of IM9 cells did not elicit CD69 expression on mock-transduced NK-92 cells, yet induced a moderate, but significant, increase in CD69 expression on the surface of CS1-CAR-transduced NK-92 cells (FIG. 17A). Interestingly, co-incubation with IM9 cells caused a dramatic increase in the expression of HLA-DR in both CS1-CAR-transduced and mock-transduced NK-92 cells. In the absence of IM9 target cells, there was no obvious difference in HLA-DR expression between CS1-CAR-transduced and mock-transduced NK-92 cells; however, upon stimulation with IM9 cells, the expression of HLA-DR became significantly higher in NK-92-CS1-CAR cells than in mock-transduced NK-92 cells. Thus, the increase in the activation markers, especially HLA-DR, expressed on NK-92-CS1-CAR cells may have occurred in connection with the enhanced cytotoxicity and IFN-γ production by these cells when they are exposed to CS1$^+$MM cells. Using intracellular staining, when compared with mock-transduced NK cells, NK-92-CS1-CAR cells had significantly higher levels of perforin and granzyme B expression, even in the absence of MM tumor cells (FIGS. 17B and 17C). This is consistent with a previous report regarding the elevated expression of granzyme B in CAR T cells (Koehler H, et al. Cancer Res 2007 67:2265-2273), and also consistent with the fact that perforin and granzyme B expression are generally correlated with cytotoxic activity of NK cells (Krzewski K, et al. Front Immunol 2012 3:335).

Figure 18A:
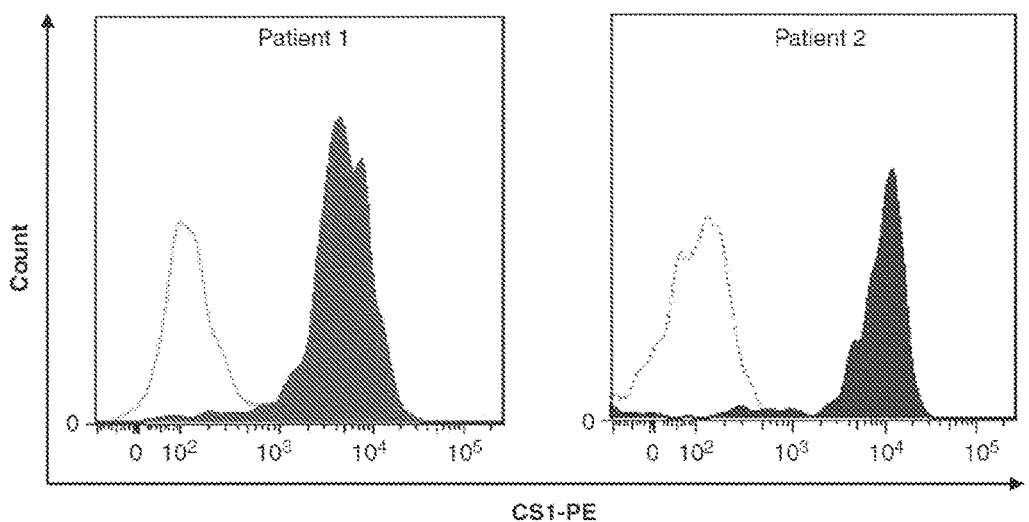
FIGS. 18A to 18C show CS1-CAR-transduced NK-92 cells enhance killing of primary human myeloma cells.
Figure 18B:
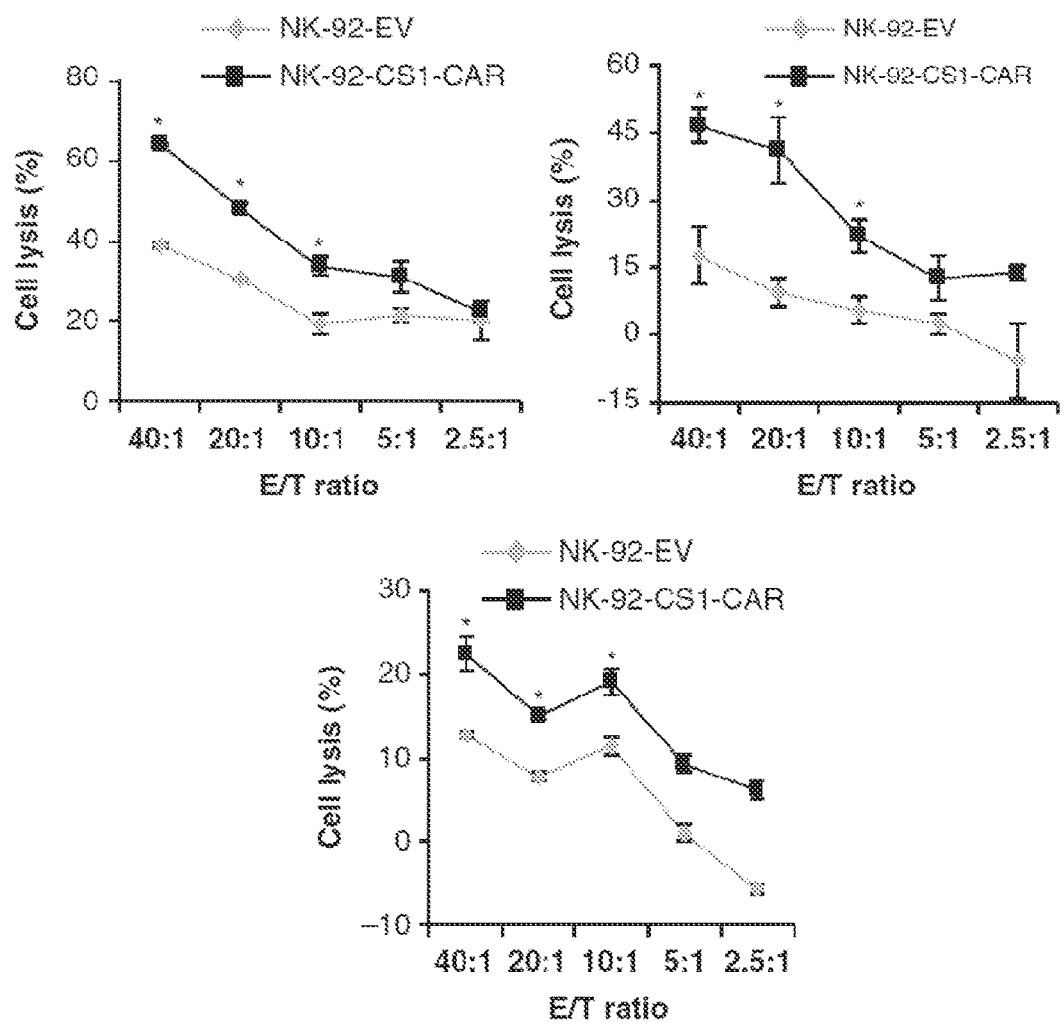
Figure 18C:
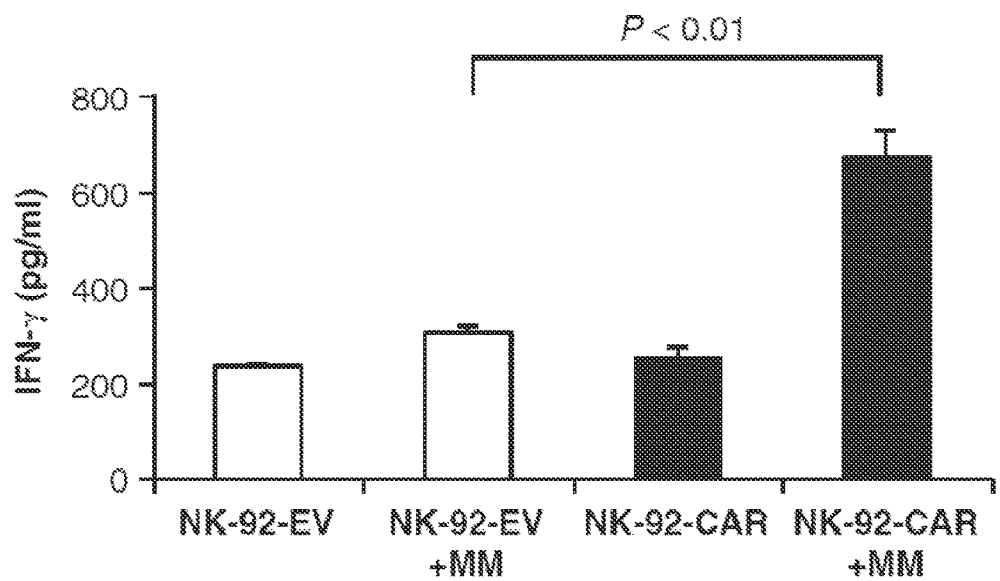

CS1-CAR-Transduced NK-92 Cells More Effectively Recognize and Kill NK-Resistant Primary MM Cells Ex Vivo To make the findings more clinically relevant, it was investigated whether CS1-CAR-modified NK-92 cells also harbored enhanced cytolytic activity and IFN-γ production when recognizing primary MM cells ex vivo. Flow cytometry was used to assess surface expression of CS1 on primary CD138$^+$ magnetic bead-selected MM cells from MM patients (FIG. 18A). In accordance with the previous report, showing that CS1 protein was highly expressed on CD138 magnetic bead-purified MM patient cells (Hsi E D, et al. Clin Cancer Res 2008 14:2775-2784; Tai Y T, et al. Blood 2008 112:1329-1337), CS1 protein was indeed uniformly expressed on the surface of primary MM cells (FIG. 18A). By chromium-51 release assay, primary myeloma cells freshly isolated from MM patients were shown to be highly resistant to NK-92 cell-mediated lysis even at E:T ratios as high as 40:1 and 20:1; however, this resistance could be partially overcome by NK-92 cell expression of CS1-CAR, which resulted in a dramatic increase in eradication of primary myeloma cells (FIG. 18B). In line with the cytotoxicity result, after 24 h co-culture with primary myeloma cells, CS1-CAR-transduced NK-92 cells also secreted significantly higher levels of IFN-γ than mock-transduced NK-92 cells (FIG. 18C).

Figure 19A:
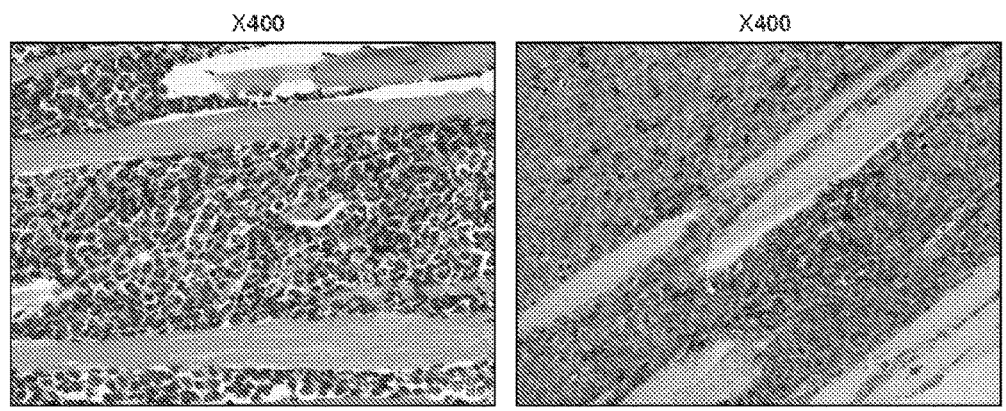
FIGS. 19A to 19D show CS1-CAR NK cells suppress in vivo growth of orthotopic human MM cells and prolong the survival of MM-bearing mice.
Figure 19B:
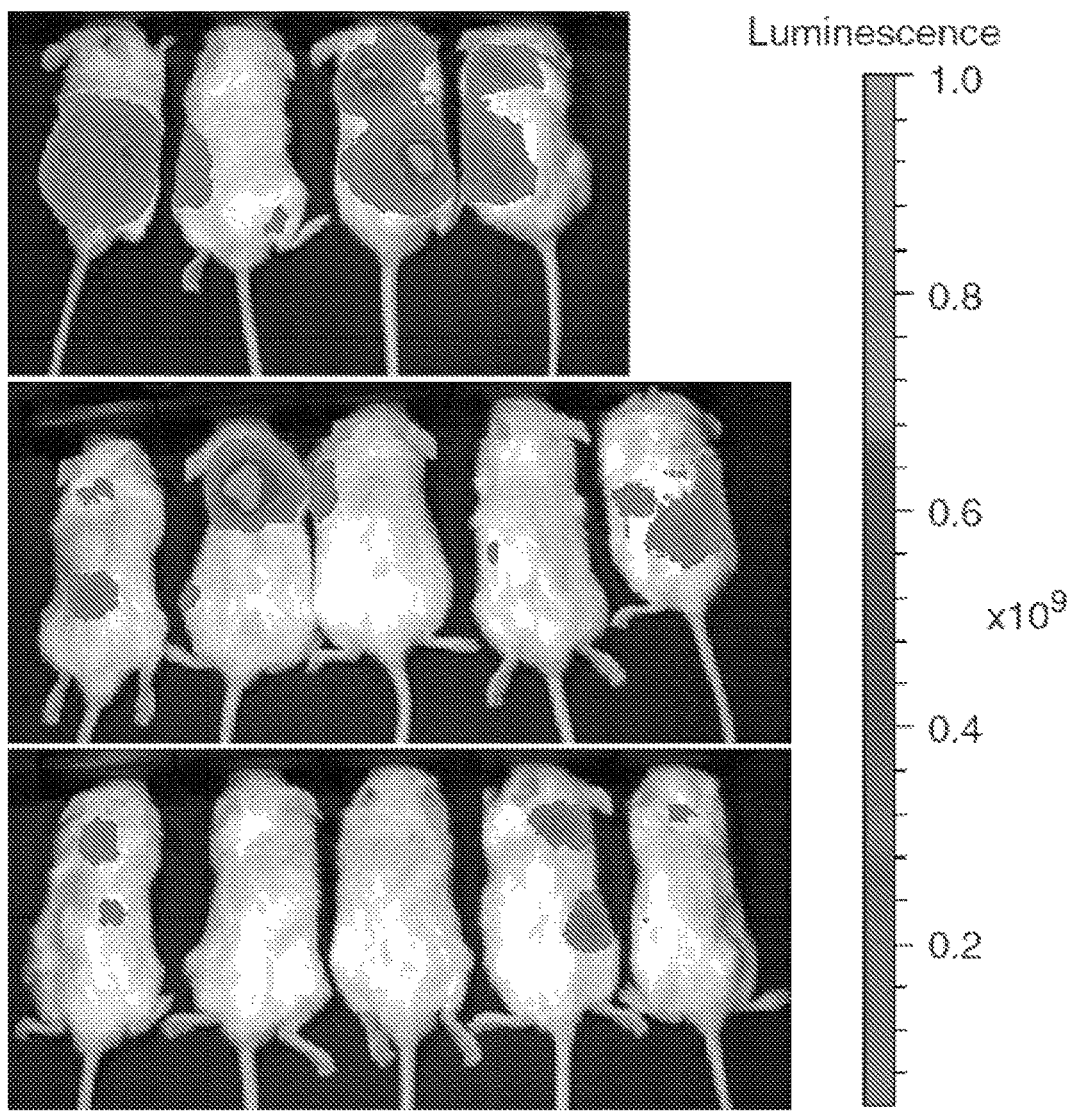
Figure 19C:
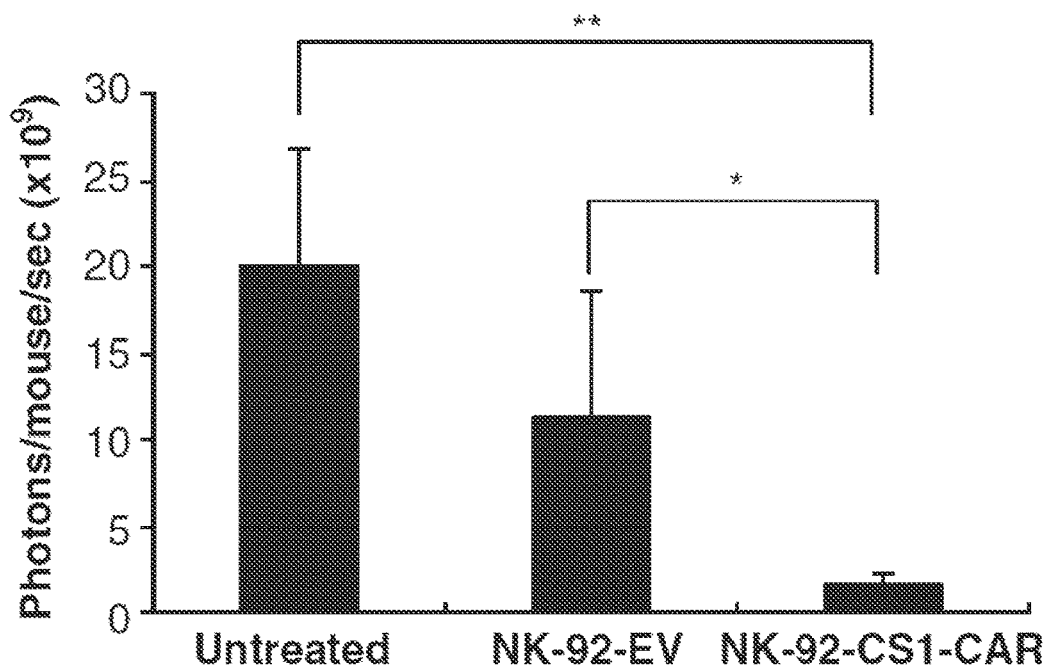
Figure 19D:
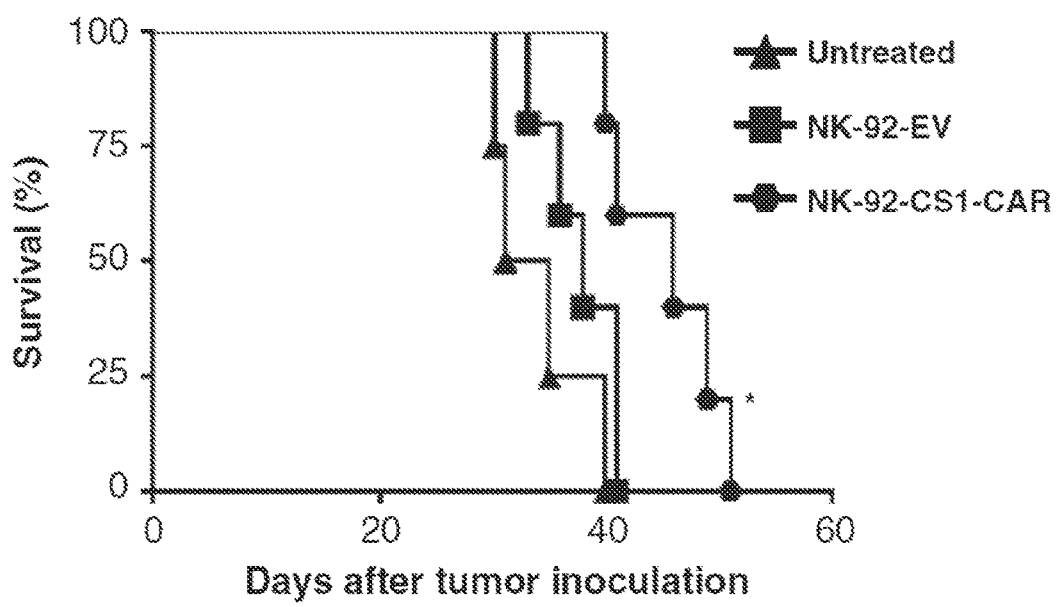

CS1-CAR-Transduced NK-92 Cells Inhibit MM Tumor Growth and Prolong Survival of Tumor-Bearing Mice in an Orthotopic Xenograft MM Model To further address the potential therapeutic application of NK-92-CS1-CAR cells, their antitumor activity was examined in IM9-xenografted NSG mice. An IM9 cell line expressing firefly luciferase (IM9-Luc) was generated by retrovirally transducing IM9 cells with virus expressing firefly luciferase, then performing GFP-based cell sorting. The expression of full-length firefly luciferase mRNA was confirmed by RT-PCR. Like typical myeloma cells, IM9-Luc cells expressed CD138 protein on their surface. In agreement with a previous report (Francisco J A, et al. Cancer Res 2000 60:3225-3231), IM9-Luc-bearing NSG mice displayed disseminated disease, manifested by hindlimb paralysis and motor ataxia. Histological examination of spinal vertebrae in a mouse displaying hindlimb paralysis showed the presence of numerous tumor cells and osteolytic lesions in bone tissue (FIG. 19A, left). Immunohistochemical staining with human-specific anti-CD138 antibody further confirmed the presence of tumor cells (FIG. 19A, right). Bioluminescence imaging was used to monitor the IM9-Luc tumor growth. As shown in FIGS. 19B and 19C, and in agreement with the in vitro cytotoxicity data, comparing the mice who later received injections with mock-transduced control cells, IM9-Luc tumors were significantly suppressed in mice who instead later were administered NK-92-CS1-CAR cells. Moreover, treatment with NK-92-CS1-CAR cells significantly prolonged the survival of mice bearing IM9-Luc tumors as compared with treatment with the mock-transduced NK-92 control cells (FIG. 19D). Of note, when NK-92-CS1-CAR cells or mock-transduced NK-92 cells were similarly administered, but without i.v. injection of IM9-Luc cells, mice did not develop disseminated disease or die.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A chimeric antigen receptor (CAR) polypeptide, comprising a CS1 antigen binding domain, a transmembrane domain, an intracellular signaling domain, and a co-stimulatory signaling region, wherein the CS1 antigen binding domain consists of one single-chain variable fragment (scFv) of an antibody that specifically binds CS1.

2. The polypeptide of claim 1, wherein the costimulatory signaling region comprises the cytoplasmic domain of a costimulatory molecule selected from the group consisting of CD28 and 4-1BB.

3. The polypeptide of claim 1, wherein the CAR polypeptide is defined by the formula:

SP-CS1-HG-TM-CSR-ISD;

wherein "SP" represents a signal peptide,
wherein "CS1" represents a CS1 antigen binding domain,
wherein "HG" represents an optional hinge domain,
wherein "TM" represents a transmembrane domain,
wherein "CSR" represents a co-stimulatory signaling region,
wherein "ISD" represents an intracellular signaling domain, and
wherein "-" represents a bivalent linker.

4. The polypeptide of claim 1, wherein the intracellular signaling domain comprises a CD3 zeta (CD3ζ) signaling domain.

5. An isolated nucleic acid sequence encoding the recombinant polypeptide of claim 1.

6. A vector comprising the isolated nucleic acid sequence of claim 5.

7. An isolated cell comprising the vector of claim 6.

8. The isolated cell of claim 7, wherein the cell is selected from the group consisting of a T cell, a Natural Killer (NK) cell, and a cytotoxic T lymphocyte (CTL).

9. The isolated cell of claim 8, wherein the cell exhibits an anti-tumor immunity when the antigen binding domain of the CAR binds to CS1.

10. The polypeptide of claim 1, wherein the costimulatory molecule is CD28.

11. The polypeptide of claim 1, wherein the costimulatory molecule is 4-1BB.

* * * * *